United States Patent [19]

Jiang et al.

[11] Patent Number: 6,165,800
[45] Date of Patent: Dec. 26, 2000

[54] CHEMILUMINESCENT ENERGY TRANSFER CONJUGATES AND THEIR USES AS LABELS IN BINDING ASSAYS

[75] Inventors: Qingping Jiang, Northboro, Mass.; Jun Xi, Ithaca, N.Y.; Anand Natrajan, Manchester, N.H.; David Sharpe, Foxboro, Mass.; Marcus Baumann, Basel, Switzerland; Rolf Hilfiker, Allschwil, Switzerland; Erika Schmidt, Basel, Switzerland; Paul Senn, Bennwil, Switzerland; Fritz Thommen, Liestal, Switzerland; Adrian Waldner, Allschwil, Switzerland; Alex Alder, Arisdorf, Switzerland; Say-Jong Law, Westwood, Mass.

[73] Assignee: Bayer Corporation, East Walpole, Mass.

[21] Appl. No.: 09/086,003

[22] Filed: May 27, 1998

Related U.S. Application Data

[60] Provisional application No. 60/048,159, May 30, 1997.
[51] Int. Cl.[7] ...................... G01N 33/533; G01N 33/553; C07D 227/00
[52] U.S. Cl. .......................... 436/546; 436/526; 436/544; 436/800; 436/816; 436/817; 546/37
[58] Field of Search ............................... 530/391.3, 391.5; 436/546, 544, 800, 526, 816, 817; 546/37

[56] References Cited

U.S. PATENT DOCUMENTS

| | | | |
|---|---|---|---|
| 4,745,181 | 5/1988 | Law et al. | 530/387 |
| 4,918,192 | 4/1990 | Law et al. | 546/104 |
| 4,927,769 | 5/1990 | Chang et al. | 436/518 |
| 5,013,827 | 5/1991 | Schaap | 536/17.3 |
| 5,068,339 | 11/1991 | Schaap et al. | 548/110 |
| 5,110,932 | 5/1992 | Law et al. | 546/102 |
| 5,227,489 | 7/1993 | Law et al. | 546/23 |
| 5,241,070 | 8/1993 | Law et al. | 546/107 |
| 5,254,477 | 10/1993 | Walt | 436/172 |
| 5,326,692 | 7/1994 | Brinkley et al. | 435/6 |
| 5,332,662 | 7/1994 | Ullman | 435/28 |
| 5,395,752 | 3/1995 | Law et al. | 436/6 |
| 5,438,146 | 8/1995 | Schaap et al. | 548/110 |
| 5,445,936 | 8/1995 | Piran et al. | 435/6 |
| 5,449,556 | 9/1995 | Law et al. | 428/402.2 |
| 5,468,646 | 11/1995 | Mattingly et al. | 436/501 |
| 5,538,901 | 7/1996 | Law et al. | 436/501 |

FOREIGN PATENT DOCUMENTS

| | | |
|---|---|---|
| 0070686 A2 | 1/1983 | European Pat. Off. . |
| 0 229 943 A2 | 7/1987 | European Pat. Off. . |
| 0322926 A2 | 7/1989 | European Pat. Off. . |
| 0324202 A1 | 7/1989 | European Pat. Off. . |
| 0609885 A1 | 8/1994 | European Pat. Off. . |
| 88/00695 | 1/1988 | WIPO . |
| 90/07511 | 7/1990 | WIPO . |
| 96/41174 | 12/1996 | WIPO . |

OTHER PUBLICATIONS

M. Grayeski et al, Langmuir, vol. 13, pp. 2675–2680, 1997.

Hadjianestis et al., "Luminol chemiluminescence in micellar media II: Energy transfer to fluorescein," *J. Photochem. Photobiol. A:Chem* 69:337–343 (1993).

Kawaguichi et al., "Stabilized Phenyl Acridinium Esters For Chemiluminescent Immunoassay—Bioluminescence and Chemiluminescence, Proceedings of 9th International Symposium 1996" Edited by Hastings, Kricka and Stanley, John Wiley & Sons, 481–484 (1997).

Larena et al., "Solvent Effects in the Reaction of Lucigenin with Basic Hydrogen Peroxide: Chemiluminescence Spectra in Mixed Polar Solvents," *Monatshefte fur Chemie* 122:697–704 (1991).

Mantaka–Marketou et al., "Some Aspects of the Lucigenin Light Reaction," *Journal of Photochemistry and Photobiology, A: Chemistry* 48:337–340 (1989).

Papadopoulos et al., "Chemiluminescence of N,N' –dialkyl–9,9'–biacridinium nitrates in aqueous and non–aqueous systems," *J. Photochem. Photobiol. A: Chem.* 75:91–96 (1993).

Patel et al., "Homogenous Immunoassay Based on Chemiluminescent Energy Transfer," *Clin. Chem.* 29/9:1604–1608 (1983).

(List continued on next page.)

*Primary Examiner*—Mary E. Ceperley
*Attorney, Agent, or Firm*—Weingarten, Schurgin, Gagnebin & Hayes LLP

[57] ABSTRACT

A new class of chemiluminescent acridinium or benzacridinium compounds is disclosed by virtue of forming an intramolecular energy transfer conjugate (ETC) between the acridinium or benzacridinium compound and a luminophore. A method of extending the emission wavelengths of acridinium or benzacridinium esters in order to further reduce or eliminate the emission spectral overlap between the parent polysubstituted aryl Acridinium Esters (DMAE) and Benzacridinium Esters (LEAE) is disclosed. The ETC's retain the unique desired properties of acridinium or benzacridinium compounds including complete light emission in very short period of time, monophasic emission spectrum, simplicity of triggering mechanism, ability of labeling the biological molecules of interest to form a tracer, and good stability. Additionally, the range of the emission spectrum of an acridinium or benzacridinium compound can now be shifted at will and at longer leap through the choice of a luminophore as the integral part of an ETC molecule. Disclosed are chemiluminescent labeled conjugates comprising an acridinium or benzacridinium moiety covalently attached to a luminophore via a spacer, said moiety further conjugated to a biological molecule of interest, wherein said spacer is of an appropriate length to allow the excited species generated from said moiety to transfer energy efficiently to said luminophore, resulting in the emission of light in the spectral region of said luminophore. Also disclosed are binding assays using said conjugates, test kits comprising said conjugates and methods of preparing the conjugates.

59 Claims, 28 Drawing Sheets

OTHER PUBLICATIONS

Rauhut et al., "Chemiluminescence from Reactions of Electronegativity Substituted Aryl Oxalates with Hydrogen Peroxide and Fluorescent Compounds," *Journal of American Chemical Society* 89:6515–6522 (1967).

Ribi et al., "Energy Transfer Involving Derivatives of Luminol," *Tetrahedron* 28:481–492 (1972).

Roberts et al., "Energy Transfer in Chemiluminescence. III. Intramolecular Triplet–Singlet Transfer in Derivatives of 2,3–Dihydropthalazine–1,4–dione," *Journal of the American Chemical Society* 92:4861–4867 (1970).

Roswell et al., "Energy Transfer in Chemiluminescence. II," *Journal of the American Chemical Society* 92:4855–4860 (1970).

Stryer, Lubert, "Fluorescence Energy Transfer As A Spectroscopic Ruler," *Ann. Rev. Biochem.* 47:819–846 (1978).

White et al., "Intramolecular Energy Transfer in Chemiluminescence," *Journal of The American Chemical Society* 89:3944–3945 (1967).

White et al., "Intramolecular Energy Transfer in Chemiluminescence," Mol. Lumin. Int. Conf., Ed: E. Lim, Publisher: W. A. Benjamin Inc., N.Y. 479–492 (1969).

Wilson et al., "The Chemiluminescence from *cis*–Diethoxy–1,2–dioxetane. An Unexpected Effect of Oxygen," *Journal of the American Chemical Society* 93:4126–4136 (1971).

FIG. 7 Structure of NSP-DMAE-HD-3-CMO-Cortisol Tracer

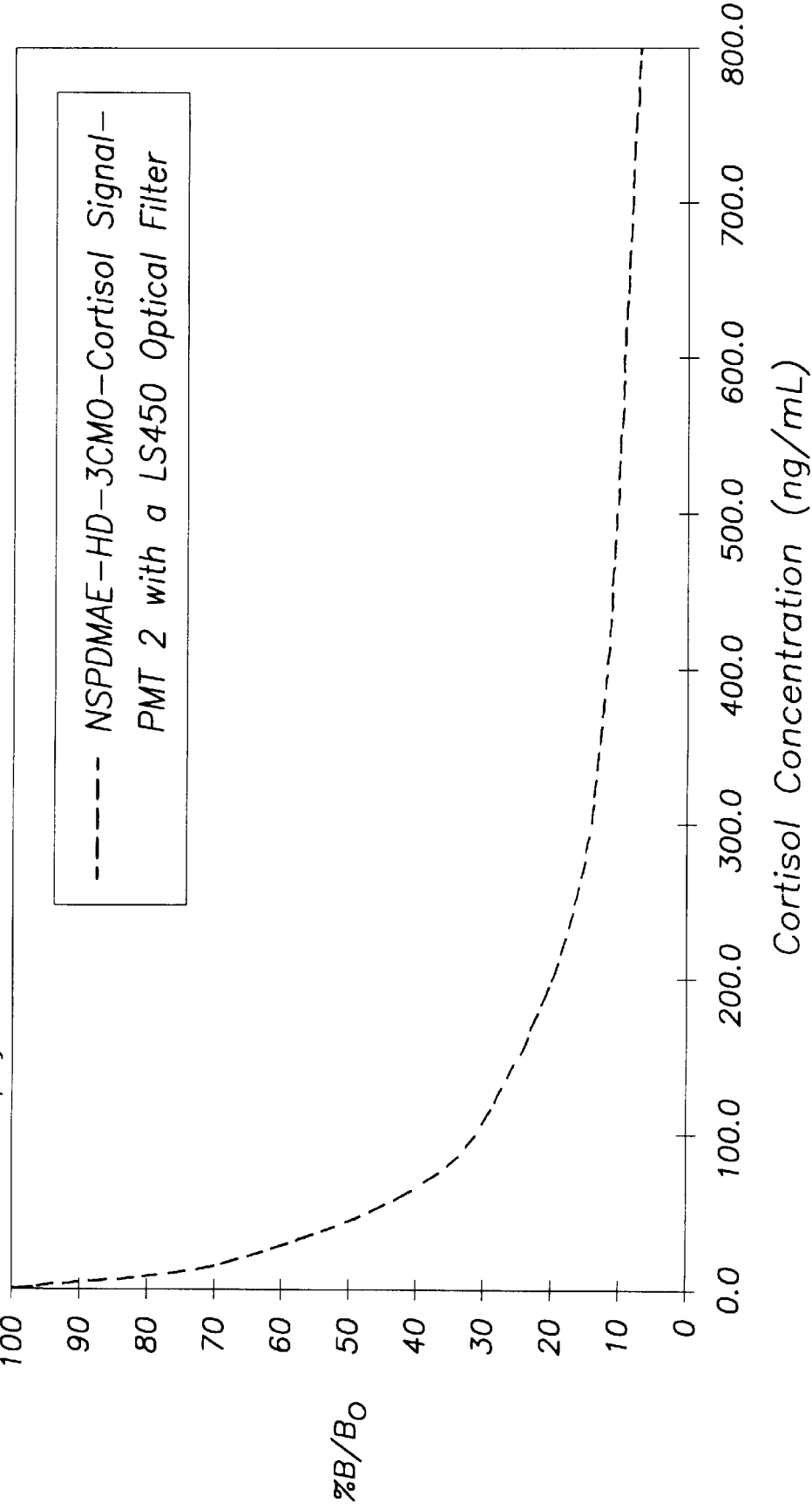
FIG. 11 Cortisol Standard Curve Determined from an Assay Mixture of Theophylline and Cortisol Standards
--- NSPDMAE-HD-3CMO-Cortisol Signal-PMT 2 with a LS450 Optical Filter

CHEMILUMINESCENT ENERGY TRANSFER CONJUGATES AND THEIR USES AS LABELS IN BINDING ASSAYS

This Appln claims the benfit of U.S. Provisional Application No. 60/048,159 filed May 30, 1997.

BACKGROUND OF THE INVENTION

This invention relates to novel energy transfer conjugates (ETC's) or labeling agents comprising a chemiluminescent acridinium or benzacridinium derivative covalently attached with a luminophore. This invention also relates to a class of ETC's with ranges of emission wavelength which are distinctively different from or minimally overlapped with those of the chemiluminescent acridinium or benzacridinium derivatives. This invention further relates to the novel application of ETC as a chemiluminescent label in the determination of analytes in a sample, such as diagnostic tests.

Since the development of the polysubstituted aryl acridinium ester (DMAE in U.S. Pat. No. 4,745,181) and its derivatives such as the 3-Methoxy-substituted DMAE, benz[b]acridinium ester (LEAE in U.S. Pat. No. 5,395,752), and 2-Methoxybenz[b]acridinium ester with emission wavelength maxima which are 6 nm shorter or, 96 nm and 122 nm longer than that of the parent DMAE (emission maximum of 428 nm), we continue our research to identify novel acridinium compounds and their synthesis, particularly those that extend the emission wavelength of acridinium compounds including specifically DMAE and generally its well known analogs, e.g., the relatively stable acridinium esters with mono-ortho substituted phenoxy moiety (EP 0609885A1; M. Kawaguichi et al., "Stabilized Phenyl Acridinium Esters For Chemiluminescent Immunoassay—Bioluminescence and Chemiluminescence, Proceedings of 9th International Symposium 1996", Edited by Hastings, Kricka and Stanley, John Wiley & Sons, 1997, pp. 480–484), and the acridinium sulfonylamides (U.S. Pat. No. 5,468,646). The ultimate purpose of the research is to a) improve or eliminate the minimal emission spectral overlap between DMAE and LEAE, b) discover another chemiluminescent label for biomolecules which has emission wavelength longer than that of LEAE and is minimally overlapped with the latter, c) increase the quantum yield of DMAE. Any efforts directed toward these goals must proceed under the pre-requisite that the new chemiluminescent labels will emit light under the same triggering conditions. Accomplishment of the objective (a) would eliminate the need of applying the cross-talk correction routine in the dual-analyte binding assays that employ the dual labels of DMAE and LEAE. With the achievement of objective (b), a third chemiluminescent label would be available for the development of a triple-analyte binding assays. Objective (c) represents one of the possible approaches which is based on the rationale that longer emission chemiluminescent compounds will have lower energy state, hence the probability of populating the chemically-converted, excited state species will be improved to allow better over-all quantum yield.

For the design of acridinium derivatives capable of emitting light at any desired spectral ranges, the present invention adopted the well-known general concept of energy transfer. Unlike the many reported instances of intermolecular energy transfer that involves two separate donor and acceptor molecules, where the donor can be a chemiluminescent compound or a luminophore, and the acceptor is always a luminophore, we have our novel design of linking the acridinium compound and the acceptor luminophore together into one molecule in order to achieve more efficient intramolecular energy transfer. In doing so, we can effectively channel the chemical energy generated in the acridinium moiety to the selected luminophore moiety, so that the latter can be excited and emit light at its characteristic and expected wavelength range. With regard to the design goals of operating uniquely within the system of chemiluminescent acridinium compounds and the requirements for high sensitivity (femtomolar, fM) in aqueous media, fast-production (in a few seconds) of light, monophasic emission (meaning only one emission maximum), and longer emission maxima, some distinct differences exist between inter- and intramolecular energy transfer phenomena and should be mentioned as the following:

M. M. Rauhut et.al. [J. Amer. Chem. Soc., 89, 6515 (1967)] first reported intermolecular energy transfer as observed in the chemiluminescence generated from the reactions of electronegatively substituted aryl oxalates with hydrogen peroxide and fluorescent compounds. Since in general, the effectiveness of energy transfer diminishes at the rate of the sixth power of the distance between the donor and acceptor, [in other words the donor and acceptor molecules should be within the distance of <10 nm to give 20–100% efficiency of transfer; see Clin. Chem., 29 (9), 1604 (1983) and Ann. Rev. Biochem., 47, 819 (1978)], millimolar (mM, $10^{12}$ folds higher than the requirement) concentration of the acceptor is required. Furthermore there are several other drawbacks in the chemiluminescent peroxalate system which makes it unsuitable for use in biological assays. These drawbacks include long duration (>one minute) for the total light emission, decreased stability of the oxalate in aqueous media, and the need of an organic solvent to solubilize the fluorophore.

Similarly J. Hadjianestis [J. Photochem. Photobiol., A: Chem, 69, 337 (1992)] reported less than quantitative (79%) energy transfer between chemiluminescent luminol and fluorescein. To achieve the maximal result, both donor and acceptor are required to reach only at micromolar (uM, $10^9$ folds higher than the requirement) concentration, due to the concentrating effect of a surfactant, CTAC. However, the biphasic profile of the emission spectra generated from this luminol/fluorescein system extending broadly from 350–600 nm renders it unsuitable for a highly sensitive, multi-analyte binding assay.

Other observations of intermolecular energy transfer that have been reported include cis-diethoxy-1,2-dioxetane to perylene [T. Wilson, et.al., J. Amer. Chem. Soc., 93 (17) 4126 (1971)], N-methylacridone to lucigenin [A. E. Mantaka-Marketou, et.al., J. Photochem. Photobiol., A: Chem., 48, 337 (1989); A. Larena, et.al., Monatshefte Chemie, 122, 697 (1991); K. Papadopoulos, et.al., J. Photochem. Photobiol., A: Chem., 75, 91 (1993)]. Aside from the need of high concentrations (uM to mM) of the acceptor, the articles focused on the elucidation of energy transfer and mechanistic studies in the chemiluminescence of dioxetane and lucigenin systems. No application of the energy transfer phenomenon to high sensitivity binding assays was suggested.

The application of intermolecular energy transfer phenomena to immunoassays was first reported by A. Patel, et.al. [Clin. Chem., 29 (9), 1604 (1983)]. A homogenous type immunoassay was developed by utilizing the specific binding property of a hapten conjugated with chemiluminescent isoluminol derivative (ABEI) and an antibody labeled with fluorescein. Since each reagent was added to the assay mix at nanomolar (nM) concentrations which are marginal for intermolecular energy transfer to be observed between the isoluminol and fluorescein moieties, only through the mediation of a specific complex formed between the hapten conjugate and the antibody conjugate that the donor/acceptor molecules have the chance to be pulled into close proximity to allow energy transfer to occur. This immunoassay method is unique in this regard. However, this method suffers from principal drawbacks of limited usefulness, low assay sensitivity (>$10^{10}$ analyte molecules/test) inherent in a homogenous assay format and the interference of high background signal originating from the energy donor due to the incomplete energy transfer. Besides, the accuracy of the analyte determination has to depend on the signal ratios taken from the diminishing donor signal and increasing acceptor signal of the assay mix that have significant spectral overlap.

L. E. Morrison, et. al. (EP Patent Application #0070686 A2) teach an enhanced (enzymatic) luminescence immunochemical principle for detecting antigens with multiple binding sites, by employing intermolecular energy transfer from a luminol substrate to an antibody-conjugated fluorophore. This rather complex assay architecture contains also catalase and an antibody-conjugated glucose oxidase as the necessary reagents. The antigen-bound antibody conjugates work together in close proximity to produce specific signal by utilizing the cofactors generated ($H_2O_2$) or present (luminol) nearby and providing with the required energy acceptor. The catalase serves as a scavenger for the portion of $H_2O_2$ which diffuses away from the antigen/antibody complex, thus minimizing the background chemiluminescence produced by luminol in solution, which is too far to be effectively transferred to the fluorophore. No assay examples were provided to prove the concept is functional.

Minister van Welzijn (NL Patent application #8703075A) described 10-carboxyalkyl-acridinium ester derivatives and suggested its conjugation to an antibody or antigen for use in a homogeneous assay, based on the principle of chemiluminescence intermolecular energy transfer as described by Patel. No example of a functional assay was given.

In the field of intramolecular energy transfer, related prior art can be identified and distinguished from the following:

Several related articles were published concerning intramolecular energy transfer conjugates between chemiluminescent luminol or benzluminol to four other fluorophores, i.e. diphenylanthracene, benzcarbazole, acridone, and benzacridone [E. H. White, et.al., J. Amer. Chem. Soc., 89, 3944 (1967); E. H. White et.al., Mol. Lumin. Int. Conf., 479 (1969), Ed.: E. Lim, Publisher: W. A. Benjamin Inc., New York.; D. F. Roswell, et.al., J. Amer. Chem. Soc., 92, 4855 (1970); D. R. Roberts, et.al., J. Amer. Chem. Soc., 92, 4861 (1970); M. A. Ribi, et.al., Tetrahedron, 28, 481 (1972)]. The quantum yields of such conjugates in aqueous media are all significantly lower than the parent luminol ranging from 26%, 4.4%, 8%, and about 13% of luminol quantum yield, respectively. No application of these luminol derivatives in diagnostic tests was suggested.

Schaap et.al. (WO #90/07511) described another intramolecular energy transfer system involving the conjugation of adamantanyl dioxetanes with fluorophores, wherein the dioxetane moiety is substituted with a cleavable group X (e.g. phosphate) and upon the leaving of X, which can be triggered enzymatically or chemically, enhanced chemiluminescence evolves. It was reported that the original light emitting species, methyl 3-hydroxybenzoate (MHB) which splits from the native adamantanyl dioxetane during the chemiluminescence process, is inherently a very poor light emitter in aqueous media. By tethering a fluorophore to MHB the excitation energy of MHB can be transferred to the fluorophore which has much better light emission in aqueous media and results in an absolute quantum yield improvement from 0.017% to about 1–2% in the presence of CTAB surfactant. The uses of this fluorophore-tethered stable dioxetane were not clearly taught nor claimed in the application. Moreover, its usefulness in enzyme-linked immunoassays and enzyme-linked DNA probes as well as direct, chemically triggerable labels for biomolecules was only briefly alluded in the Field of Invention section. As in the earlier related patent application on other stable dioxetanes by Bronstein (WO 88/00695), the fluorophore-tethered stable dioxetane of Schaap will most likely find its use as a substrate for enzyme-linked tracers or probes in binding assays to achieve enhanced chemiluminescence. For this type of use, however, Schaap did not provide any teaching as to how a multianalyte assay system can be devised, and it certainly would not be possible, unless different enzyme-substrate systems that are non mutually interacting have been made available and clearly demonstrated. Furthermore, the suggestion for an alternative use of this fluorophore-tethered stable dioxetane as a direct label for biomolecules also lacks supportive evidence because in the specification and claim of the general structure of fluorophore-tethered dioxetane, one can not find provisions for specific functional group that would make its direct labeling of the biomolecules possible. The suggestion can be meaningful only if such biomolecule conjugate can be prepared and its stability demonstrated. Additionally, although the well known stable dioxetane with cleavable group X is a very useful means for signal amplification when serving as a substrate for enzyme-linked tracer, it suffers the drawback of slow emission of light due to not only the required long lag time (20 min or more) in the enzymatic cleavage of X, but also the slow decay process ($t_{1/2}$ greater than one min) that begins with the cleaving of X and ends up with the light emission.

SUMMARY OF THE INVENTION

A new class of chemiluminescent acridinium or benzacridinium compounds is disclosed by virtue of forming an intramolecular energy transfer conjugate (ETC) between the acridinium or benzacridinium compound and a luminophore. A method of extending the emission wavelengths of acridinium or benzacridinium esters in order to further reduce or eliminate the emission spectral overlap between the parent polysubstituted aryl Acridinium Esters (DMAE) and Benzacridinium Esters (LEAE) is disclosed herein. The ETC's retain the unique desired properties of acridinium or benzacridinium compounds including complete light emission in very short period of time, monophasic emission spectrum, simplicity of triggering mechanism, ability of labeling the biological molecules of interest to form a tracer, and good stability. Additionally, the range of the emission spectrum of an acridinium or benzacridinium compound can now be shifted at will and at longer leap through the choice of a luminophore as the integral part of an ETC molecule.

It has also been determined that all the energy transfer is highly effective regardless of which periposition at the acridinium or benzacridinium nucleus is anchored with the luminophore. By working out the covalent-anchoring of a luminophore into close proximity at any of the peripositions of the acridinium or benzacridinium nucleus, it has been demonstrated that ETC works by first converting its acridinium or benzacridinium moiety into a new species (the excited state of acridone or benzacridone) by the well known peroxide/hydroxide treatment. The excited acridone or benzacridone can then effectively transfer its energy to the luminophore moiety as a means of excitation of the liminophore and cause the luminophore to emit light at its characteristic spectral region.

With the availability of the ETCs, the dual-label binding assays can be rendered equally accurate even in the absence of a cross-talk correction routine, because of the minimal spectral overlap between the two emitting species. Larger shift of emission to an even longer wavelength also means that a triple-label assay is possible due to the demonstration of tri-phasic emission spectrum resulting from the simultaneous flashing of the mixture of present ETC and earlier reported DMAE and LEAE. In the case where remnant light emission of shorter wavelength from the ETC is still observed due to incomplete energy transfer from the excited acridone moiety to the luminophore moiety, the resulting interference to the accuracy of dual-label assay is only one-directional and is correctable by simple subtraction in the shorter wavelength channel of the portion of signal that is contributed by the ETC. The correction can be done by applying the predetermined ratio of emission intensity of the shorter wavelength signal relative to the longer wavelength signal in ETC. Such a correction, however, reduces the dynamic range of the measurable concentration ratio of the two components in dual label assay. It is therefore important that the energy transfer is almost complete. This requirement is met by the compounds described in this instant application.

Accordingly, it is a primary object of the invention to provide acridinium- or benzacridinium-based chemiluminescent ETC's with more flexible and further shift of emission wavelength from blue light to near infra red.

Another object of the invention is to provide methods for synthesis of acridinium- or benzacridinium-based chemiluminescent ETC and intermediate products which may be used to synthesize such chemiluminescent compounds.

A further object of the invention is to provide ETC conjugates formed between ETC directly or indirectly with binding partners or biological molecules, some of which are included by virtue of their function, such as haptens, ligands, receptors, and antibodies, while others are included by virtue of their chemical nature, such as polysaccharides, polypeptides, and nucleic acids.

An additional object of the invention is to provide hydrophilic ETC which carries one or more ionic and/or ionizable groups with or without, additionally, the reactive functional groups useful for forming covalent linkage with other micro- or macromolecules or encapsulation inside liposomes.

A further object of the invention is to provide test assays involving the use of ETC conjugates.

An additional object of the invention is to provide a simultaneous multi chemiluminescent label assay.

Another object of the invention is to provide a method for the simultaneous detection and/or quantitation of at least two substances in a test sample by use of at least two different chemiluminescent compounds or conjugates, one or more of which are associated with ETC's, each having discernible emission spectra.

A further object of the invention is to provide multianalyte assays in which the determination of two or more analytes or substances or combination thereof present in the sample as a mixture, can be carried out simultaneously in the same reaction medium or transfer tube due to the mutually non-interfering or minimally overlapping but correctable light signals produced by the same chemical treatment of two or more different chemiluminescent tracers or compounds, one or more of which are associated with ETC's.

Still another object of the invention is to provide test kits having two or more chemiluminescent reagents, one or more of which contain ETC labels, for simultaneously assaying at least two substances in a test sample.

These and other objects in view, as will be apparent to those skilled in the art, the invention resides in the combination of elements set forth in the specification and covered by the claims appended hereto.

BRIEF DESCRIPTION OF THE DRAWINGS

FIGS. 1A–1L are emission spectra as determined on a Fast Spectral Scanning System of the ETC's corresponding to Rhodamine-2-AM-DMAE-Bz, Rhodamine-2-AM-DMAE-$CO_2H$, Texas Red-2-AM-DMAE-$CO_2H$, CNF-2-AM-DMAE-$CO_2H$, Texas Red-3-AM-DMAE-$CO_2H$, Rhodamine-3-AM-DMAE-β-Alanine, Texas Red-3-AM-DMAE-β-Alanine, Texas Red-ED-NCM-DMPAE, Texas Red-ED-NSP-DMPAE, Rhodamin-2-AM-DMAE-HD-Theophylline, Texas Red-3-APO-DMAE-Bz and Texas Red-3-ABO-DMAE-Bz.

FIG. 1O is the emission spectrum of the mixture of DMAE-Bz and Rhodamine-2-AM-DMAE-Bz.

DESCRIPTION OF PREFERRED EMBODIMENT

Figure 1A:
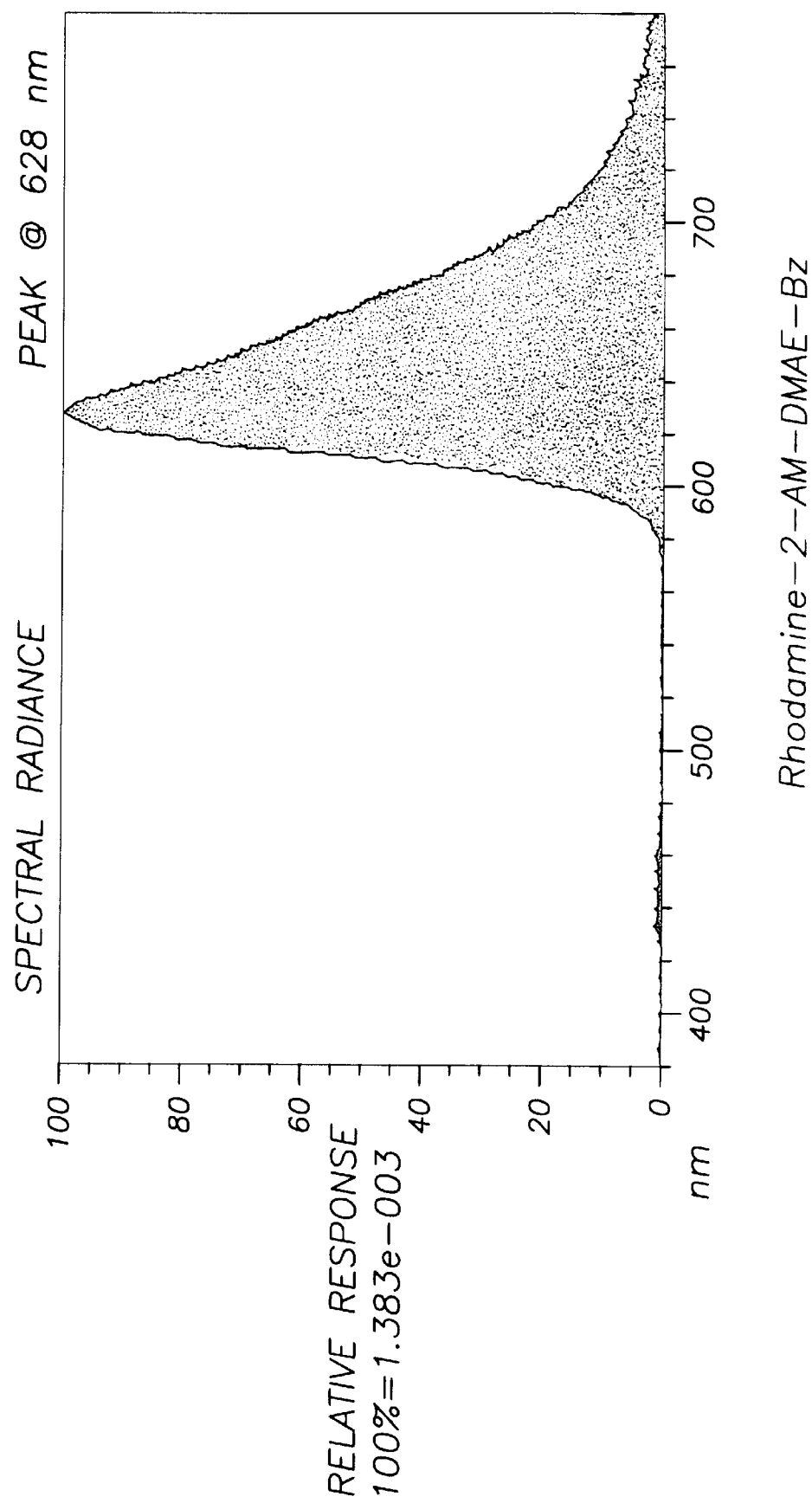
Figure 1B:
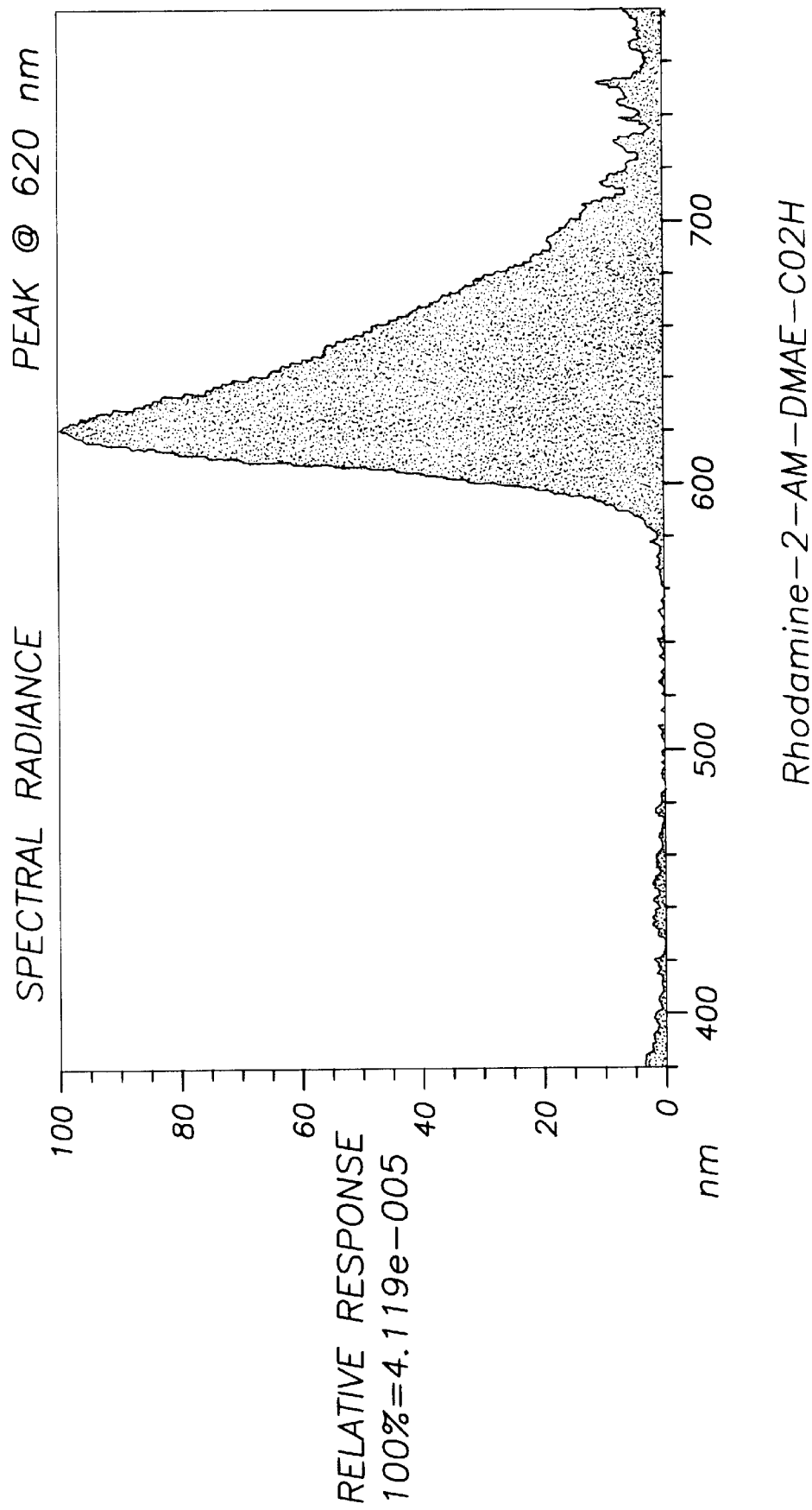
Figure 1C:
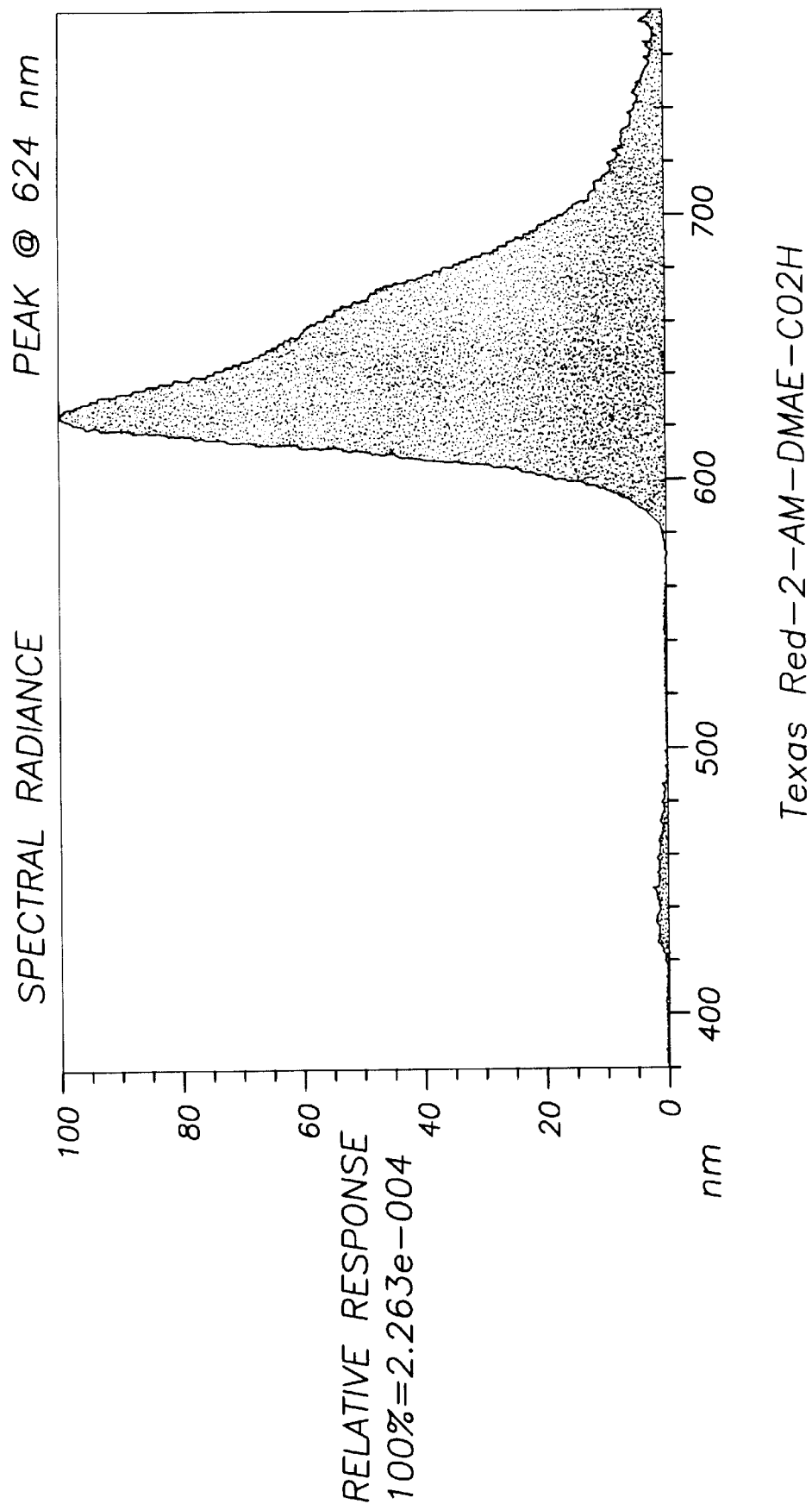
Figure 1D:
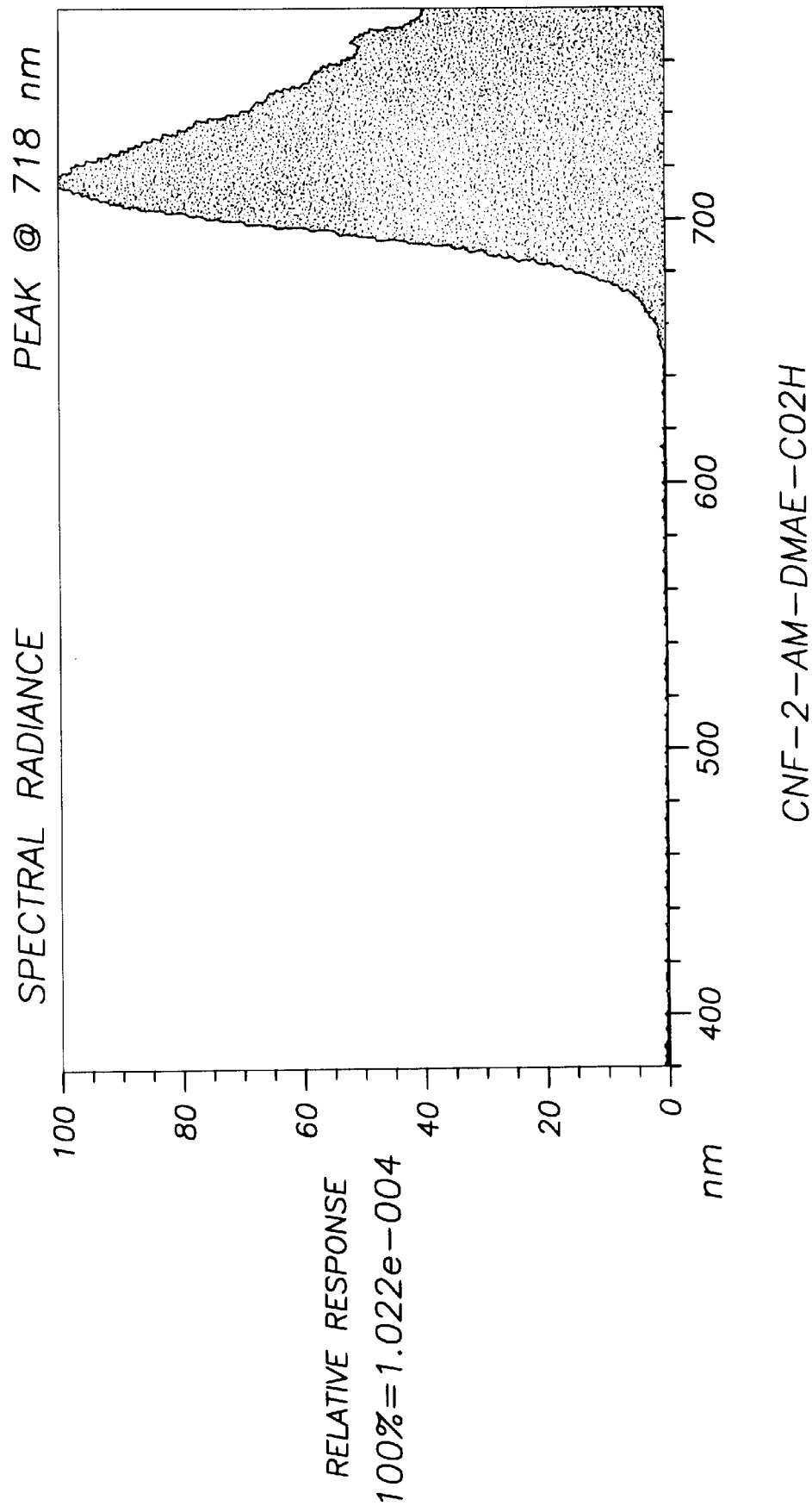
Figure 1E:
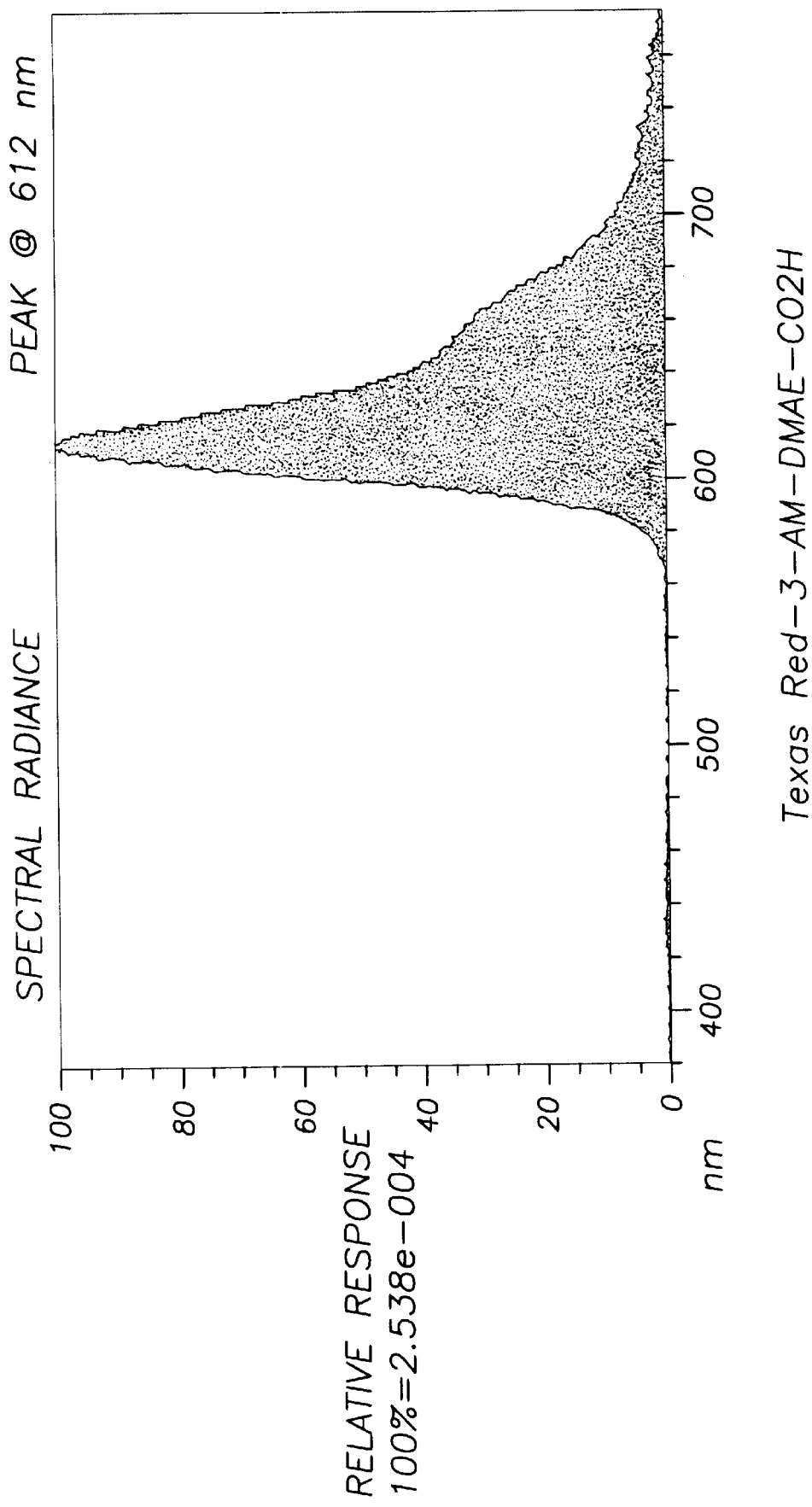
Figure 1F:
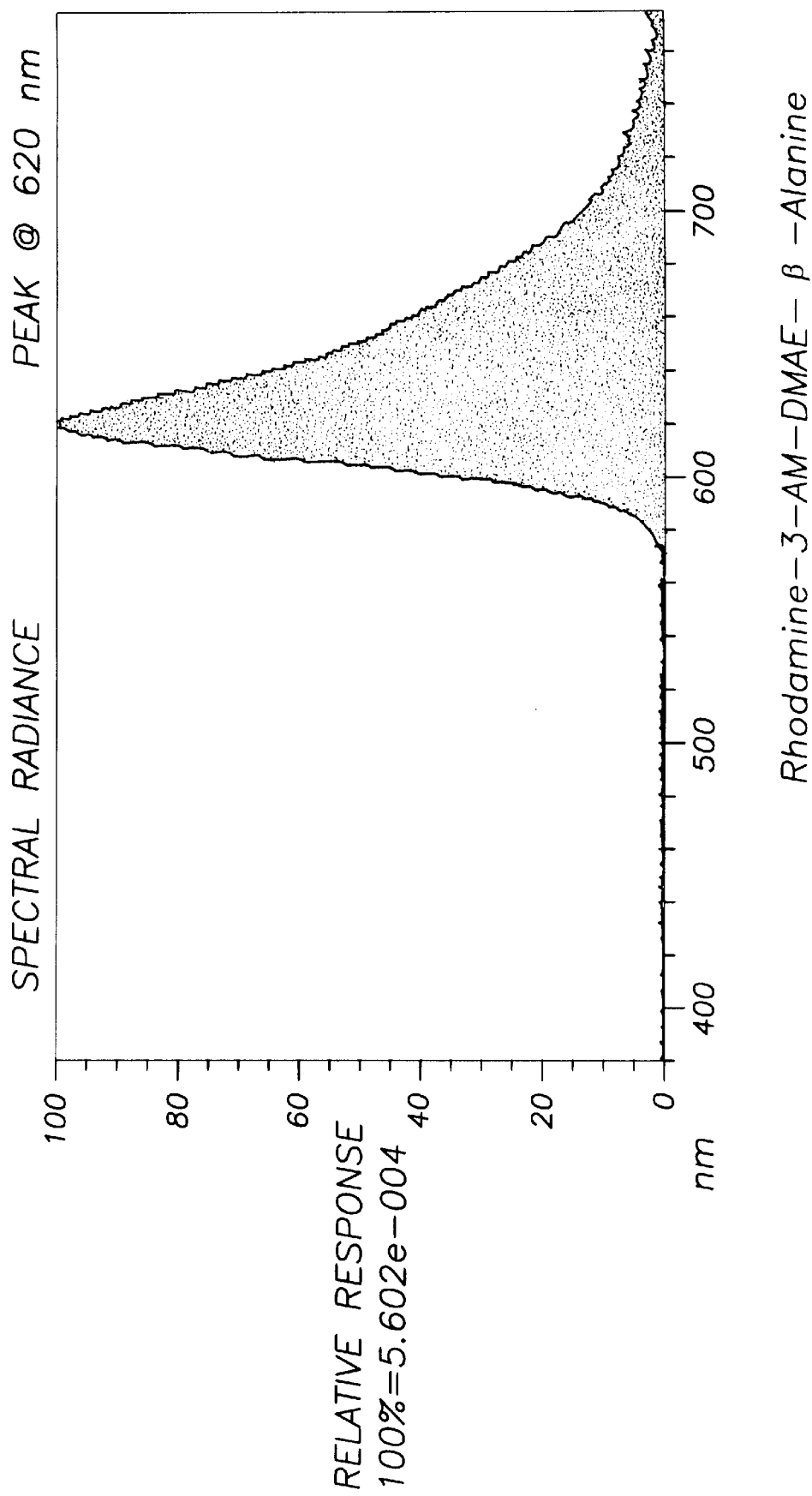
Figure 1G:
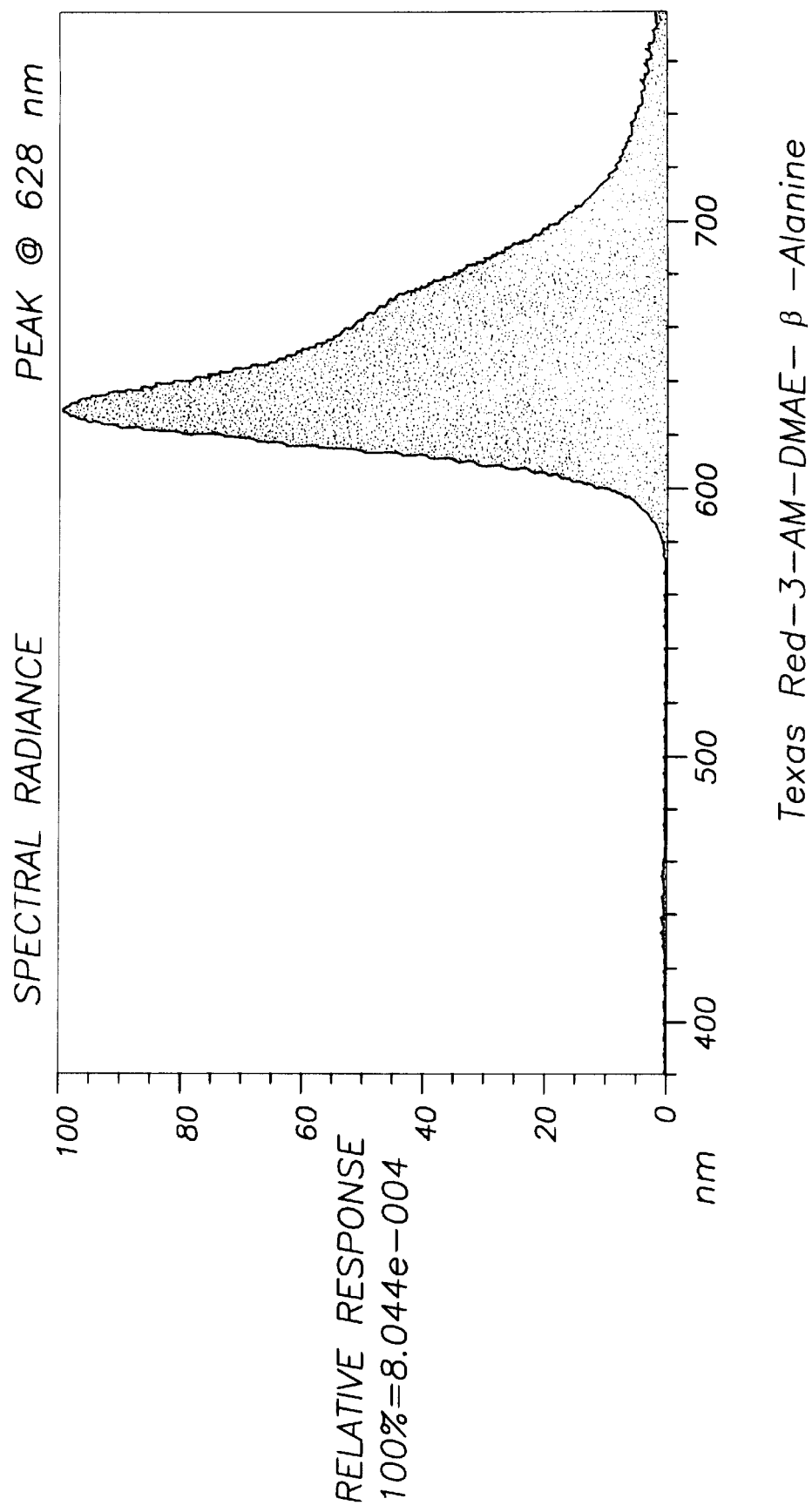
Figure 1H:
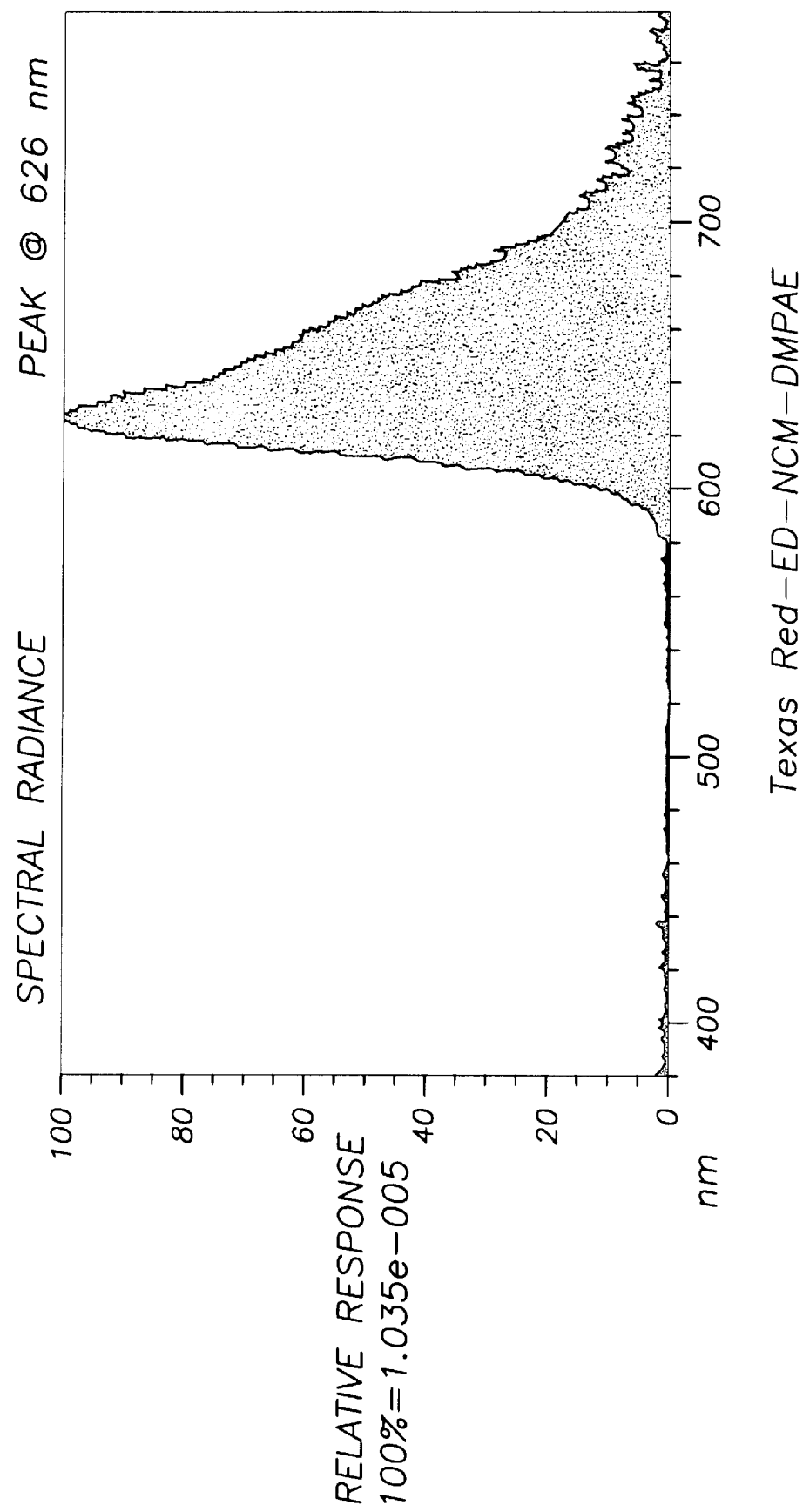

A. Structures and General Assembling of ETC's

The acridinium- or benzacridinium-based ETC's of the present invention comprises acridinium or benzacridinium moiety conjugated with a luminophore via a spacer. (For the clarity of the description, "acridinium or benzacridinium moiety" in the instant application denotes part of Formula I or II, respectively, that does not include the luminophore moiety, e.g., Formula I and II excluding the lumiphore, which would be located in the $R_1$, $R_2$, or $R_3$ position, while "acridinium or benzacridinium nucleus" denotes that part of Formula I or II, that is boxed within the dotted lines.) The luminophore (described more fully below) can be thus anchored at any one of the peri-positions as represented by $R_1$, $R_2$, and $R_3$ substituents of the acridinium or benzacridinium nucleus in the following general structures of ETC's:

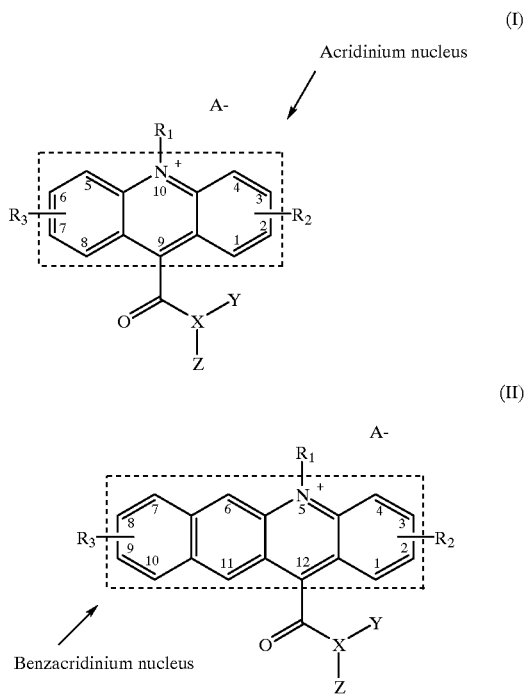

Where, $R_1$, $R_2$, or $R_3$ represents -Sp-Lumi, and Lumi is a luminophore moiety serving as an energy acceptor and Sp represents a spacer or a first side chain comprising linear, branched, or cyclic alkyl, alkenyl, alkynyl, alkoxyl, or aralkyl chain of less than 50 angstroms with up to 20 heteroatoms, preferably less than 30 angstroms with up to 12 heteroatoms, and most preferably less than 10 angstrom with up to 8 heteroatoms. The terms "spacer" and "side chain" will be used interchangeably in this application. The length of the side chain between the lumiphore and the acridinium or benzacridinium nucleus is chosen so that it is an appropriate length to allow the excited form of the resulting acridone or benzacridone to more or less completely transfer energy to said lumiphore, resulting in the emission of light in the spectral range of the lumiphore. Preferably, the spacer contains at least one functional linkage resulting from the coupling of the functionalized side chains of the acridinium or benzacridinium nucleus and the functionalized luminophore. Said functional linkages includes, but not limited to, the following commonly encountered ones: —NHCO— (amide), —CONH— (amide), —NHCOO— (carbamate), —O— (ether), —C=N—O— (oxime ether), —S— (thioether, or sulfide), —S—S— (disulfide), —NHCO—NH— (urea), —NHCSNH— (thiourea), —C=N— (imino)-, —NH— (amino), —N=N— (diazo), —COO— (ester), —C=C— (vinyl, alkenyl, or olefinic), and —SO$_2$NH— (sulfonamide), —C≡C— (alkynyl), —OPO$_3$—, —PO$_3$—, —OSO$_3$—, and —SO$_3$—.

The methods of forming the above functional linkages are well known to those skilled in the art and have been well recorded in Organic Chemistry text books, e.g. Advanced Organic Chemistry: Reactions, Mechanisms, and Structure, Ed. I–IV, by Jerry March.

Lumi represents a Luminophore, which includes, for the purpose of present invention, (1) a phosphorescent moiety, (2) a fluorophore, or (3) the precursor of either (1) or (2) which is non-phosphorescent or non-fluorescent but convertible to a phosphorescent or fluorescent moiety upon chemical or enzymatic treatment. Luminophores suitable for the purpose of the present invention can be the well known and existing commercial products or any future novel luminescent compounds that are capable of producing emission spectra covering from blue to infra red (IR) region. Preferably the luminophores can be or have been functionalized at a position that would not affect its light emission ability, and can survive the transient low and high pH conditions as would be required during the flashing of acridinium or benzacridinium moiety with which the luminophores are coupled with.

When one of the substituents on the acridinium or benzacridinium nucleus, i.e. $R_1$, $R_2$, or $R_3$, is as described above the other two substituents represent the following:

$R_1$, if not substituted with -Sp-Lumi, alternatively, can be an alkyl, alkenyl, alkynyl or aralkyl containing optionally up to 20 heteroatoms;

$R_2$ and $R_3$, if not substituted with —Sp-Lumi, alternatively, are identical or different, single or multiple groups at $C_{1-4}$ and $C_{5-8}$ for formula (I) and at $C_{1-4}$ and $C_{6-11}$ for formula (II), respectively, selected from hydrogen, substituted or unsubstituted aryl (ArR or Ar), halide, amino, hydroxyl, nitro, sulfonate, —R, —CN, —COOH, —SCN, —OR, —SR, —SSR, —C(O)R, —C(O)OR, —C(O)NHR, or —NHC(O)R.

For example, in Scheme I, in Rhodamine-2-AM-DMAE-Bz, $R_2$ is the substituent which contains Sp-Lumi, where Sp and Lumi are shown below, while $R_1$ is methyl and $R_3$ is hydrogen.

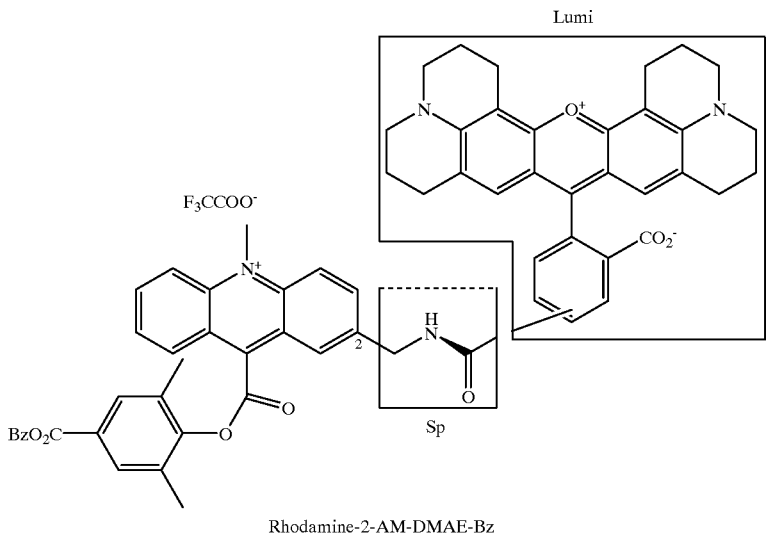

Rhodamine-2-AM-DMAE-Bz

In addition, in Scheme VIII, in Texas Red-ED-NCM-DMPAE, $R_1$ is Sp-Lumi (shown below), while $R_2$ and $R_3$ are hydrogens.

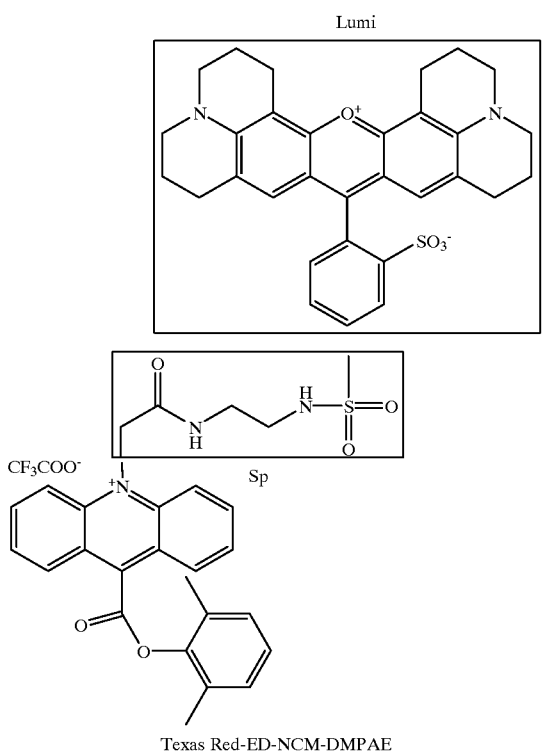

Texas Red-ED-NCM-DMPAE $A^-$ is a counter ion which is introduced to pair with the quarternery nitrogen of the ETC molecules either as a result of quartemnerizing the acridine or benzacridine ring nitrogen by the use of alkylating agents (e.g. Scheme I.) during the synthesis, modification of the $R_1$ side chain (e.g. Schemes II and IX), or subsequent exchange mechanisms that occur during the work-up of reaction mixtures and purification of desired compounds (e.g. Schemes I, II, V, VI, VIII, and IX) in a solution or fluid containing excess amount of other anions. Examples of the counter ions include $CH_3SO_4^-$, $FSO_3^-$, $CF_3SO_3^-$, $C_4F_9SO_4^-$, $CH_3C_6H_4SO_3^-$, halide, $CF_3COO^-$, $CH_3COO^-$, $NO_3^-$, and phosphate.

X is nitrogen, oxygen or sulfur;

When X is oxygen or sulfur, Z is omitted and Y is a polysubstituted aryl moiety of the formula:

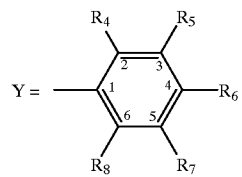

where $R_4$ and $R_8$ are alkyl, alkenyl, alkynyl, alkoxyl (—OR), alkylthiol (—SR), or substituted amino groups that serve to stabilize the —COX— linkage between the acridinium or benzacridinium nucleus and the Y moiety, through steric and/or electronic effect. Additionally, $R_4$ and $R_8$ can be either the same or different; furthermore one of $R_4$ and $R_8$ can be hydrogen without seriously compromising the stability of the —COX— linkage.

$R_5$ and $R_7$ are any of $R_2$ and $R_3$ defined above;

$R_6$=—$R_9$—$R_{10}$, the key substituent containing necessary functional group for conjugating to biological molecule of interest, where $R_9$ is a second side chain, not required but optionally can be branched or straight-chain alkyl, substituted or unsubstituted aryl or aralkyl containing optionally up to 20 heteroatoms, and $R_{10}$ is a leaving group or an electrophilic functional group attached with a leaving group including:

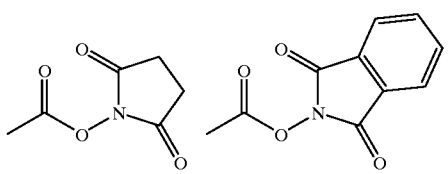

-continued

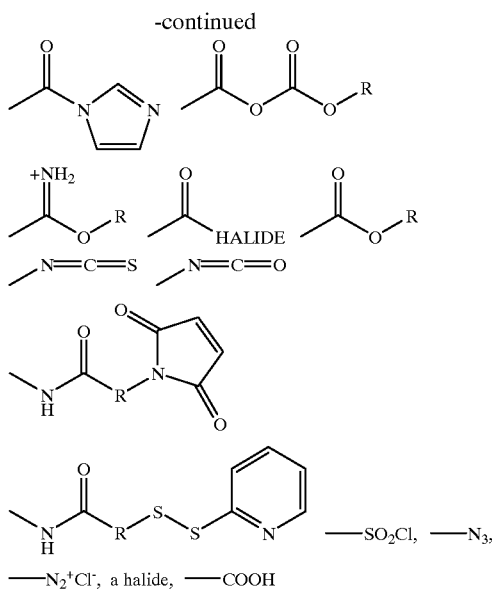

—Q—R—Nu, —Q—R—(I)nNu—, —Q—Nu, —R—Nu, or —Nu, n is a number of at least 1, Nu is a nucleophilic group, Q is a functional linkage, I is an ionic or ionizable group; detailed definitions of Nu, Q, and I can be found in the U.S. Pat. No. 5,241,070, column 3, line 45 to column 3, line 16. The reactions contemplated for Nu was also described in the same patent, column 3, line 48 to column 4, line 18.

$R_5$ and $R_6$, and $R_6$ and $R_7$ are interchangeable; and R is alkyl, alkenyl, alkynyl, aryl or aralkyl containing optionally up to 20 heteroatoms.

When X is nitrogen, Y is (1) a branched or straight-chain alkyl group, containing up to 20 carbon atoms and optionally up to 10 heteroatoms or (2) a substituted or non-substituted aryl or heteroaryl group containing up to 20 carbon atoms; Z is —$SO_2$—Y', Y' is defined the same as Y above (in the case where X is nitrogen). Y and Y' can have either the same or different chemical composition.

Figure 12A:
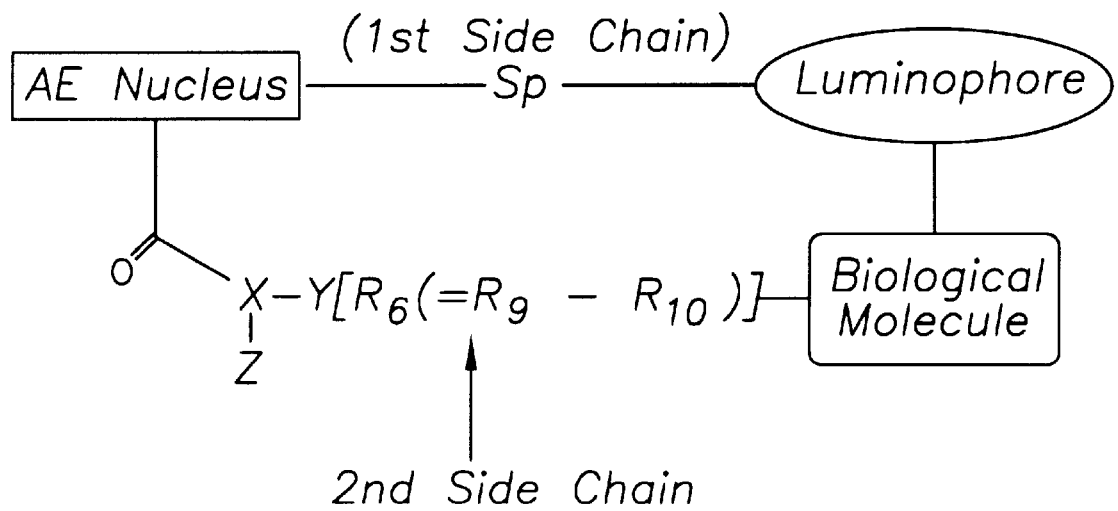
FIG. 12 shows various constructs of the chemiluminescent labeled conjugates.
Figure 12B:
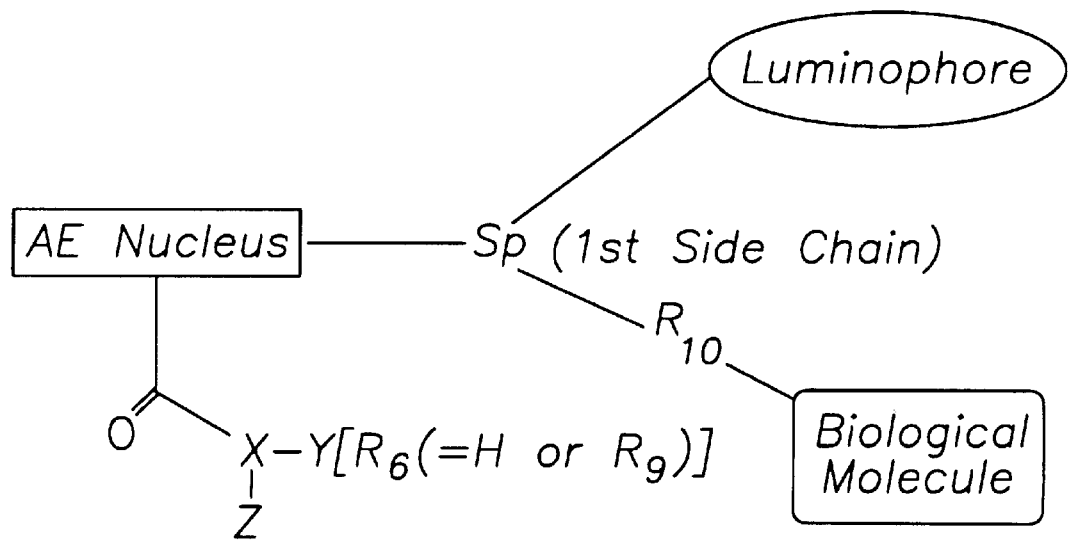

A preferred construct of the chemiluminescent labeled conjugate (which contains the ETC conjugated to a biological molecule) as described above is shown in FIG. 12A. An alternative design of the ETC (as shown in FIG. 12B) is the translocation of the functional group of $R_{10}$ described above. Instead of forming part of $R_6$ at the Y moiety, $R_{10}$, whose purpose is to facilitate covalent attachment for the biological molecule, is now located at the first side chain (-Sp-). One example of such a functionalized spacer is the tri-functional molecule, lysine, in which the α-amino and α-carboxylate groups serve to cross-link the acridinium or benzacridinium nucleus and luminophore, while the ε-amino group of the lysine side chain can be utilized for conjugation. Other permutations (or orientations) of lysine cross-linking and the use of other tri-functional molecules are also possible and should be obvious to those skilled in the art of cross-linking. For the choice of this design, the artisans are cautioned, however, against the possibility of lowered light detection. As it is well known that upon flashing the acridinium ester will give rise to the light emitting acridone and the phenoxy group. Instead of being retained with the phenoxy group as in the previous design, the biological molecules would now stay tethered with the acridone and compete with the luminophore to absorb the light, resulting in the reduction of over-all quantum yield of the ETC. The extent of the inhibitory effect is of course a function of the chromophoric features of the biological molecules and the distances between the acridinium ester and the biological molecule or the luminophore.

Figure 12C:
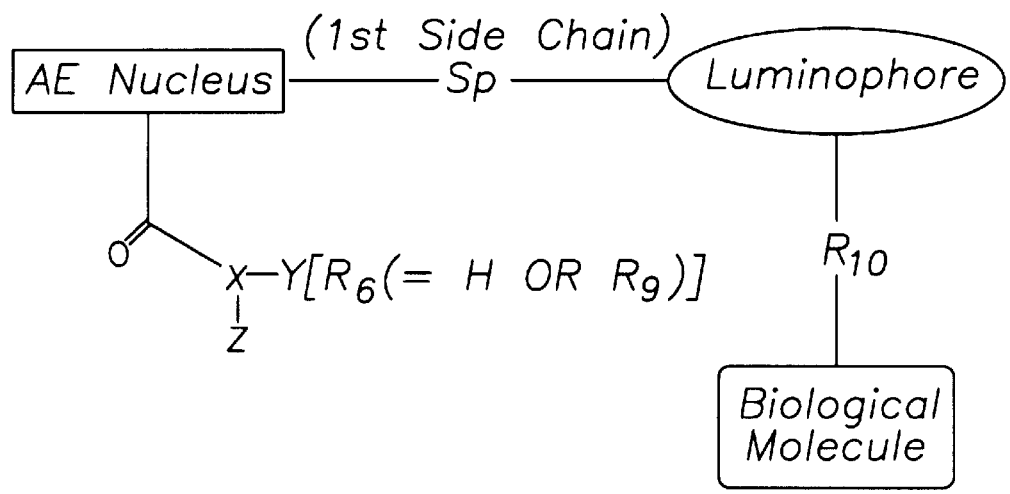

A further alternative design of the ETC's (as shown in FIG. 12C), similarly, could arise by translocating the $R_{10}$ group from the acridinium or benzacridinium moiety to the luminophore moiety. This design would require a bi-functional luminophore, which at one end links covalently to an acridinium or benzacridinium nucleus with or without the mediation of a spacer, and at the other end binds to the biological molecule. Similar precaution against the lowering of quantum yield will also apply for this design. Depending on the structural features of the luminophore at hand, the ease of introducing bi-functional groups to a luminophore and reacting them stepwise with a spacer, acridinium or benzacridinium compound, and biological molecule in any special sequence will also vary. To a person skilled in the art of organic or bioorganic synthesis this would mean the proper selection of different protecting groups for the various functional groups in order to be able to carry out the reactions selectively and in a compatible manner.

Figure 12D:
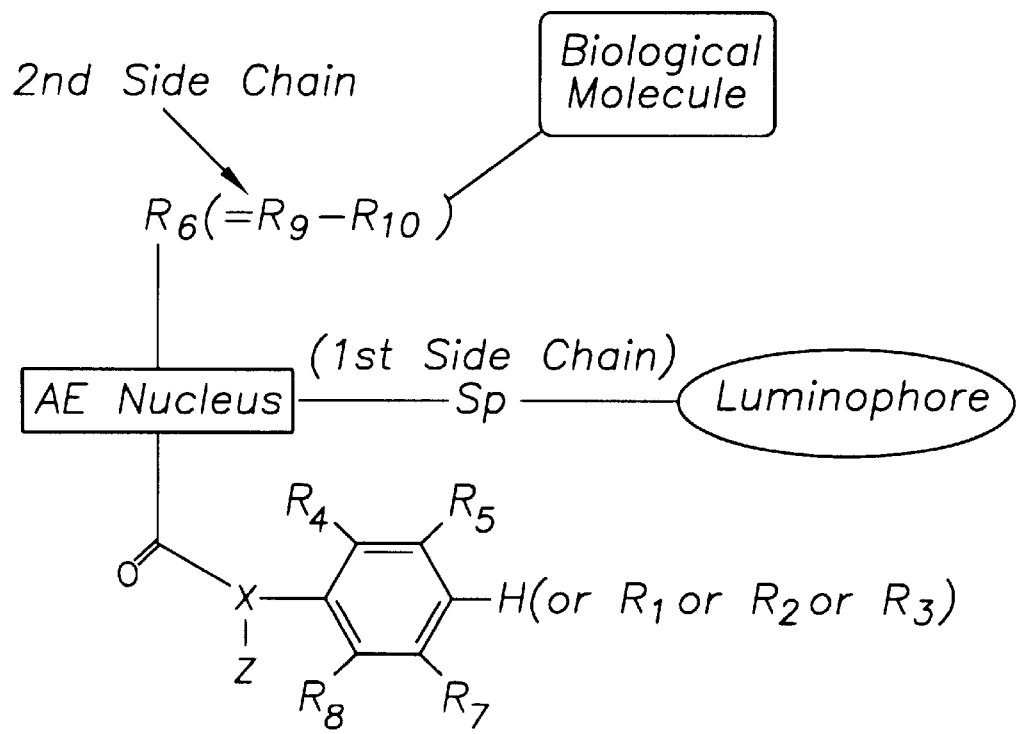

Another alternative design (see FIG. 12D), similar to the above two alternatives, for the ETC's would result from the translocation of the entire $R_6$ group from the phenolic group of the acridinium or benzacridinium moiety in Formulas I and II to the acridinium or benzacridinium nucleus. In this design, the $R_6$ replaces one of the three groups, $R_1$, $R_2$ and $R_3$, on the acridinium or benzacridinium nucleus, where the $R_6$ is a linker for conjugating the biomolecule to the acridinium or benzacridinium nucleus and one of the two other groups ($R_1/R_2$, or $R_2/R_3$, or $R_1/R_3$) represents -Sp-Lumi as defined earlier. The position originally occupied by $R_6$ on the phenoxy moiety is then replaced by a group equivalent to H, $R_1$, $R_2$, or $R_3$, $R_1$, $R_2$, or $R_3$, in this case, has the same definition but excluding -Sp-Lumi. Again, similar caution against the lowering of quantum yield will apply here for this alternative design due to the direct linkage of the biomolecules to the acridinium or benzacridinium nucleus.

A chemiluminescent ETC compound or ETC-labeled conjugate is characterized in that upon chemical treatment the compound or conjugate emits a blue-green, green, yellow, orange, red-orange, or near IR light having a discernible emission spectra peak or maximum. In one embodiment, i.e. ETC compound, the emission maximum is greater than 600 nm and in other preferred embodiments greater than 620 nm and 700 nm, respectively.

Several synthetic approaches are described for the formation of various ETC's, comprising the attachment of different luminophores via different spacers to the peripositions of the acridinium and benzacridinium nucleus, particularly at the $C_2$, $C_3$ and ring nitrogen.

A reverse block synthetic method is described for the preparation of ETC-biomolecule conjugates to circumvent the possible complication when the luminophore moiety of the ETC contains additional functional group (e.g. carboxylate or sulfonate group at the bay area of Rhodamine and Texas Red) which could be co-activated with that of $R_6$ at the acridinium ester moiety and result in undesirable by-products of ETC-biomolecule conjugates. The solution for this complication was provided through reversing the synthetic sequence of constructing the ETC-biomolecule conjugate, i.e the biological molecule was first conjugated with the acridinium ester, which in turn was coupled with the properly activated luminophore. The ETC-biomolecule so constructed was found useful as the tracer in the diagnostic test.

B. Selection of Luminophore

For the choice of luminophore, one can use preactivated and/or functionalized luminophore such as those readily available from the commercial sources (e.g. Molecular Probes, Eugene, Oreg.). Criteria for the choice of the various luminophores are rank-ordered as follows on the basis of necessity: (1) the required excitation and emission spectral ranges, (2) reasonably good stability of the compound, hence the retention of excitation and light emission capability in both extreme pH of acid and base required for the chemical conversion of the acridinium and benzacridinium moiety, (3) good luminescence quantum efficiency, (4) availability of the matching functional group (with or without preactivation) needed for coupling with the functionalized acridinium or benzacridinium described above. Most of the luminophores already existing in literature come with those information needed by one to check against the criteria for selection. For those luminophores of potential usefulness based on their luminescence properties, complete information can be made available through self testing, or further derivatization of the known compound, if necessary, until all four criteria are fulfilled. Thus, for example, luminophores such as Rhodamine functionalized with N-hydroxysuccinimide carboxylate ester at the 5- or 6-position (Molecular Probe Cat# C-1309), Texas Red functionalized with sulfonyl chloride at the 5-position, (Molecular Probe Cat.# T-353) and carboxynaphthofluorescein functionalized with N-hydroxysuccinimide carboxylate ester at the 5- or 6-position (Molecular Probe Cat# C-653) have been chosen in the present invention for their useful properties that meet the four criteria satisfactorily.

While recognizing that the known luminophores for the purpose of the present invention are abundant, the examples are intended to illustrate and not to limit the invention to the use of those exemplified luminophores only. The four criteria will therefore be serving as the guide for those skilled in the art to select either the known or future novel luminophore that is suitable for the construction of the ETC's.

C. Synthesis of Key Intermediates and Target ETC's

In order to introduce the functionalized side chain at certain desired periposition (e.g. 2- or 3-, or N-) of the acridinium or benzacridinium nucleus, methods of previous disclosure, and newly discovered procedures were utilized. For example, introduction of substituents to the 2-, or 3-position of the acridinium nucleus can be achieved by base-catalyzed rearrangement of a N-arylisatin with substituent at the aryl or isatin moiety. Thus, starting with the properly substituted aryl isatins, the key intermediates of 2- or 3-substituted acridine-9-carboxylic acid can be obtained as shown among the following Scheme I–VII for the preparations of various ETC's .

In the copending application, CIP of LEAE, U.S. application Ser. # 08/308,772, U.S. Pat. No. 5,879,894, it was found that a similar approach could be applied to the preparation of 2- or 3-substituted benzacridine-12-carboxylic acid by employing properly substituted N-arylbenzisatin.

Since the peri-substituents in the instant application include a functionalized side chain, additional care and/or steps are necessary as illustrated in the beginning steps of the following Scheme I and V, to introduce the suitably protected functionalized side chain to the aryl portion of the N-arylisatin or N-arylbenzisatin. The protection given to the intended functionalized side chain on N-arylisatin or N-arylbenzisatin can prevent any possible interference from the functional group of the side chain and guarantee the smooth formation of the properly substituted acridine or benzacridine carboxylic acid. Thus the desired functionalized side chain of aminomethyl was protected with phthalic anhydride to form phthalimidomethyl side chain. The protection of the amino group in the instant application was quite unique in that we found the protection was not totally intact after going through the base-catalyzed rearrangement as shown in the partial hydrolysis of the phthalimide moiety. Nevertheless, the protection had been sufficient to render the formation of acridine carboxylic acid unperturbed. In the subsequent steps, the phthalimide moiety was reformed by $SOCl_2$ treatment, because the protection continued to be required in the esterification step of forming the acridine esters and the methylating step of forming the acridinium ester. The amino group was then re-exposed by the hydrazine treatment to remove the phthaloyl protection just prior to the need of conjugating the substituted acridinium ester to a functionalized luminophore to form ETC. Thus, importantly, the instant application also discloses a unique process of synthesizing acridinium ester-based ETC, which utilizes the strategy of phathlimido protection of the amino functionalized side chain. Said protection effectively goes through (or survives) various reactions and finally gets removed under a condition that can leave the acridinium ester intact for necessary chemiluminescent activity.

Detailed descriptions for synthesizing the key acridinium esters with functionalized side chains at the peri-positions and their further derivatizations into ETC's are given in the examples.

A further teaching of forming ETC at the other periposition of the acridinium ester involves the introduction of the functionalized side chain of aminoethylcarbamoylmethyl (AECM) to the ring nitrogen of the acridinium or benzacridinium nucleus as the $R_1$ substituent. The synthetic route is shown in Scheme VIII and described briefly below.

Starting with the model acridine ester, dimethylphenylacridine ester (DMPAeE), the ethoxycarbonylmethyl side chain was attached to the ring nitrogen to form the N-ethyoxycarbonylmethyl-dimethylphenylacridinium ester (NECM-DMPAE) as described by Zomer et.al, (EP 0324202). We found the saponification of NECM-DMPAE did not yield the desired N-carboxymethyl-DMPAE (NCM-DMPAE) as Zomer et.al. reported. Alternatively, we discovered that DMPAE with an extended functionalized side chain of aminoethylcarbamoylmethyl on the ring nitrogen can be obtained by reacting ethylenediamine directly with NECM-DMPAE to give the key intermediate of ED-NCM-DMPAE, which was then coupled with functionalized luminophore (Texas Red) to give the desired ETC.

Similarly, introduction of another functionalized side chain of aminoethylsulfonamidyl-propyl (—$CH_2CH_2CH_2$—$SO_2NHCH_2CH_2NH_2$, also referred to as ED-NSP) to the ring nitrogen of acridinium or benzacridinium nucleus was also found possible. The synthetic route for ED-NSP acridinium ester and the subsequent ETC compound is illustrated in scheme IX described below.

Linkage of acridinium or benzacridinium esters with luminophores via other functional group, such as hydroxy group at the 3-position of the acridine nucleus is also possible. The required 3-hydroxy-acridine-9-carboxylate derivative can be prepared via the well known condensation of isatin with an appropriate phenolic compound, resorcinol (EP#0322926 A2). To facilitate the subsequent coupling with luminophores, the 3-OH group of acridine or benzacridine ester can be first derivatized, prior to the coupling, to produce an amino-functionalized alkyl or aralkyl ether spacer. One preferred embodiment of such modification resulted in the introduction of an aminobenzyloxy (ABO) spacer as shown in the example section (synthesis of Texas Red-3-ABO-DMAE-Bz). The insertion of the aminobenzyloxy spacer was unexpectedly found to produce enhanced stabilizing effect on the luminophore (Texas Red) moiety in the ETC when treated with strong base as required by the general flashing conditions of acridinium esters. No change in the absorption spectrum of a model acridone-N-ABO-Texas Red was observed when stirred at room temperature for 1 day in 0.1 N NaOH. It should be noted here, however, that for the purpose of the present invention, since the light emitted by the ETC's is mostly completed in very short period of time, stablity of the luminophore moieties to basic conditions exceeding over 10 sec is not absolutely required.

After coupling with Texas Red-sulfonyl chloride, a conjugate of acridine ester-3-ABO-Texas Red results. Unlike other synthetic approaches described above, the acridine moiety in this ABO-containing preferred embodiment was N-methylated in the last step to afford an active ETC as illustrated in Scheme X described below.

Another preferred embodiment of the ETC with a 3-aminopropyloxy linkage (Texas Red-3-APO-DMAE-Bz) was also prepared in the similar manner. (described below in Scheme XI)

A simpler construct of DMAE-ethylenediamine-Theophylline has been developed previously as the tracer in Ciba Corning's ACS Theophylline Assay. A natural modification and improvement of the tracer for the present invention is to utilize the similar Theophylline precursor, Theophylline-hexanediamine (Theo-HD), that carries a free amino group. Since the ETC of Rhodamine-2-AM-DMAE carries two carboxylate groups, one from DMAE moiety and one from Rhodamine moiety at the bay area, direct activation of Rhodamine-2-AM-DMAE to form N-hydroxysuccinimide (NHS) ester, followed by coupling with Theo-HD would possibly result in a mixture of conjugates, some of which may contain new linkage at the undesirable bay area carboxylate group, which must be kept free. A stepwise bloc synthesis was, therefore, devised and carried out for this case by first activating a properly protected 2-AM-DMAE and subsequently coupling the activated and protected 2-AM-DMAE derivative with Theo-HD, removing the 2-AM protecting group, and coupling the intermediate with the commercially available Rhodamine derivative specifically activated with NHS at the 5- or 6-carboxylate group. The complete synthesis is shown in below in scheme XII.

The emission characteristics of Rhodamine-2-AM-DMAE-HD-Theophylline was also demonstrated to be essentially that of Rhodamine-2-AM-DMAE as shown in the following section. Similarly, Rhodamine-2-AM-DMAE labeled biological molecules other than Theophylline can be constructed based on the above approach.

D. Biological Molecules Labeled with an ETC

Functionalized ETC's described above and their obvious derivatives can be used to covalently couple with biological molecules containing matching functional groups for labeling purpose. The resulting covalent linkages of amide and thioether are just a few examples most commonly anticipated by artisans skilled in the art. Other kinds of possible linkages that can be formed under organic (e.g. ether, ketone, ester, azo, etc.) or aqueous media (e.g. disulfide) and are well recorded in literature should be considered obvious without the demonstration of unexpected benefits.

Conjugation of ETC containing no interfering/competing functional group(s) in the luminophore moiety to the biological molecules should obviously be the direct labeling of the preformed and activated ETC to the biological molecules. To illustrate how a biological molecule can be conjugated to an ETC to form a tracer in the diagnostic test, and to provide an evidence that the same emission characteristics of ETC can be retained on the tracer, the synthesis of Rhodamine-2-AM-DMAE-hexanediamine-Theophylline conjugate is described.

E. Light Emission Spectra

Figure 1J:
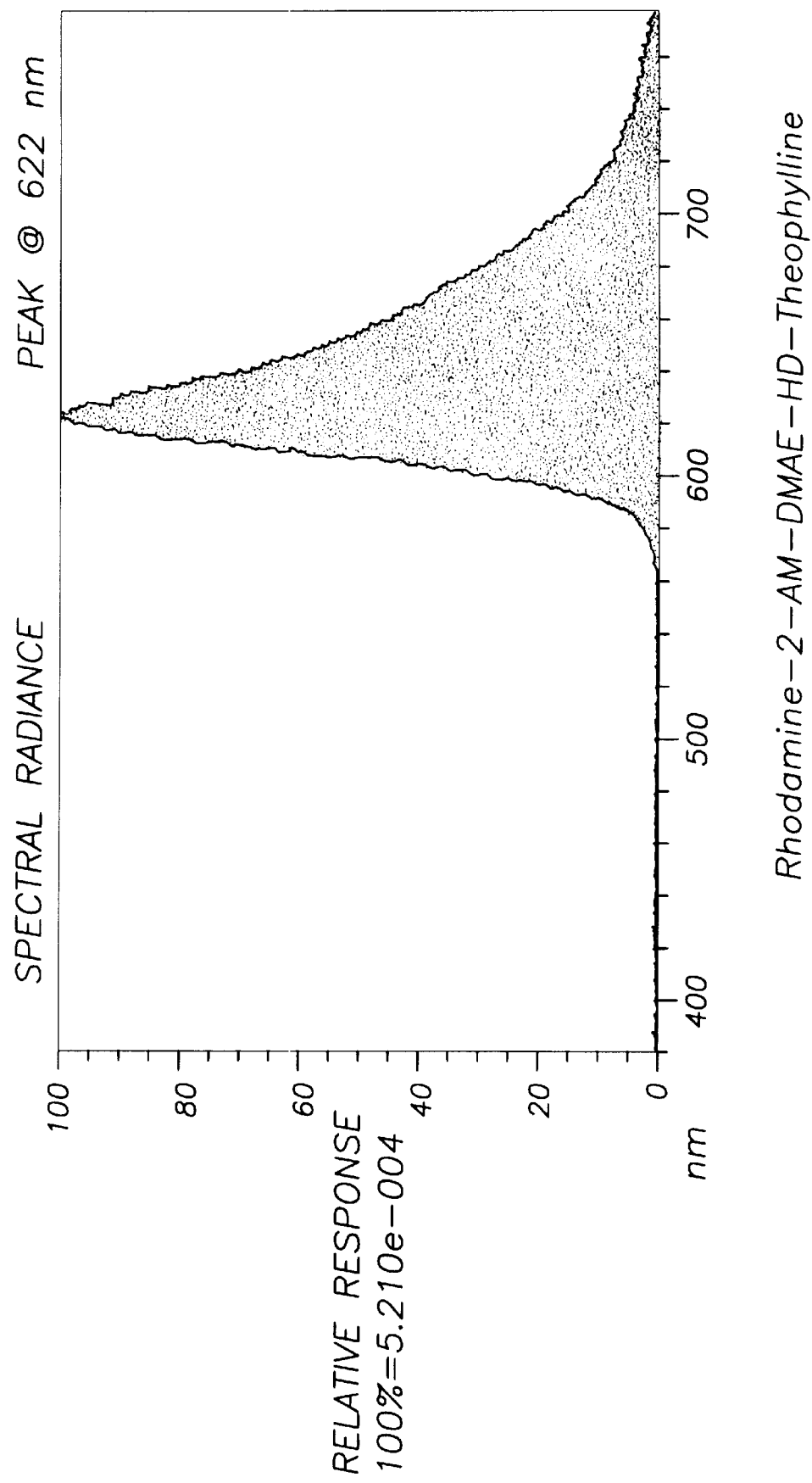
Figure 1K:
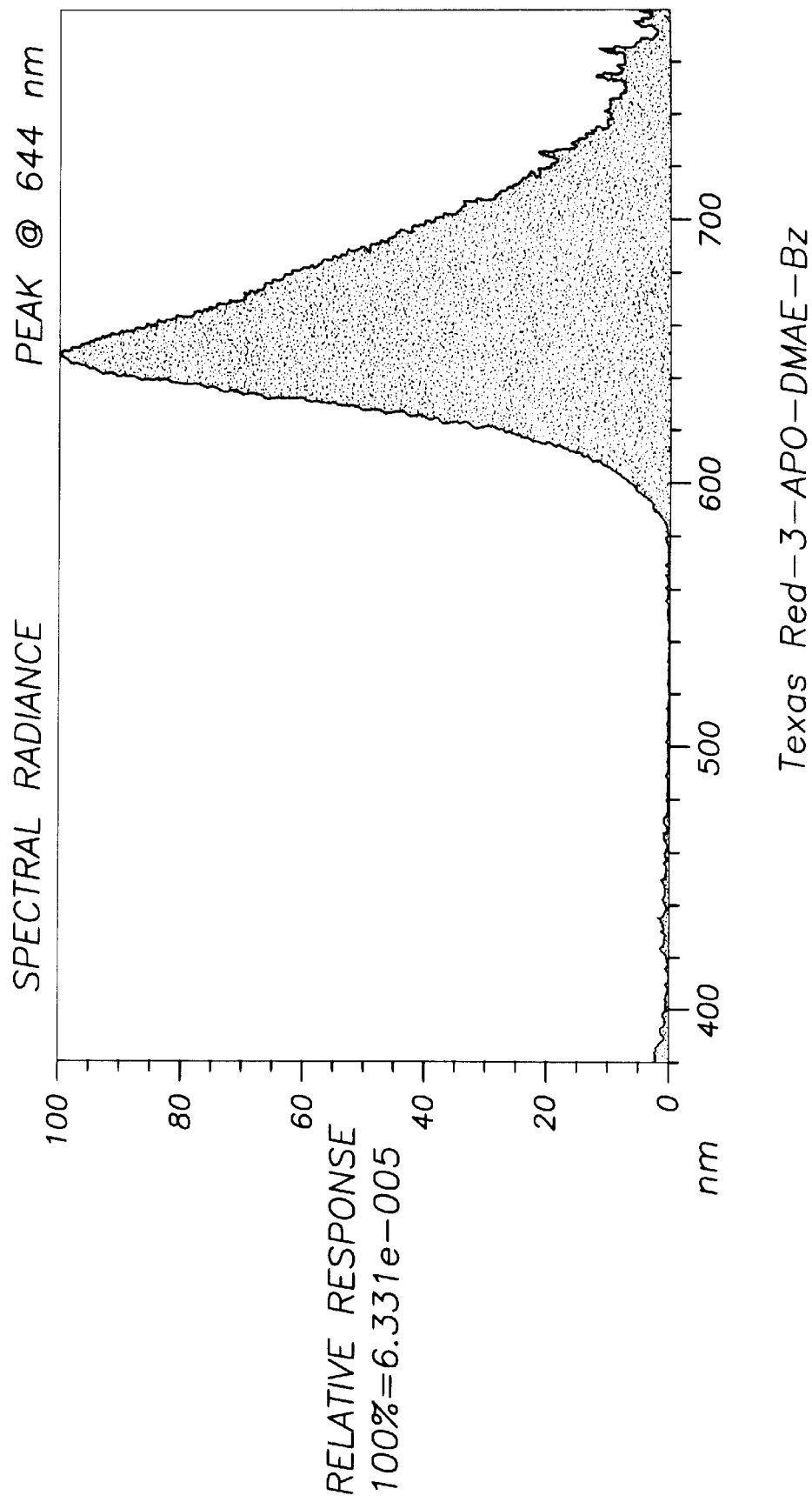
Figure 1L:
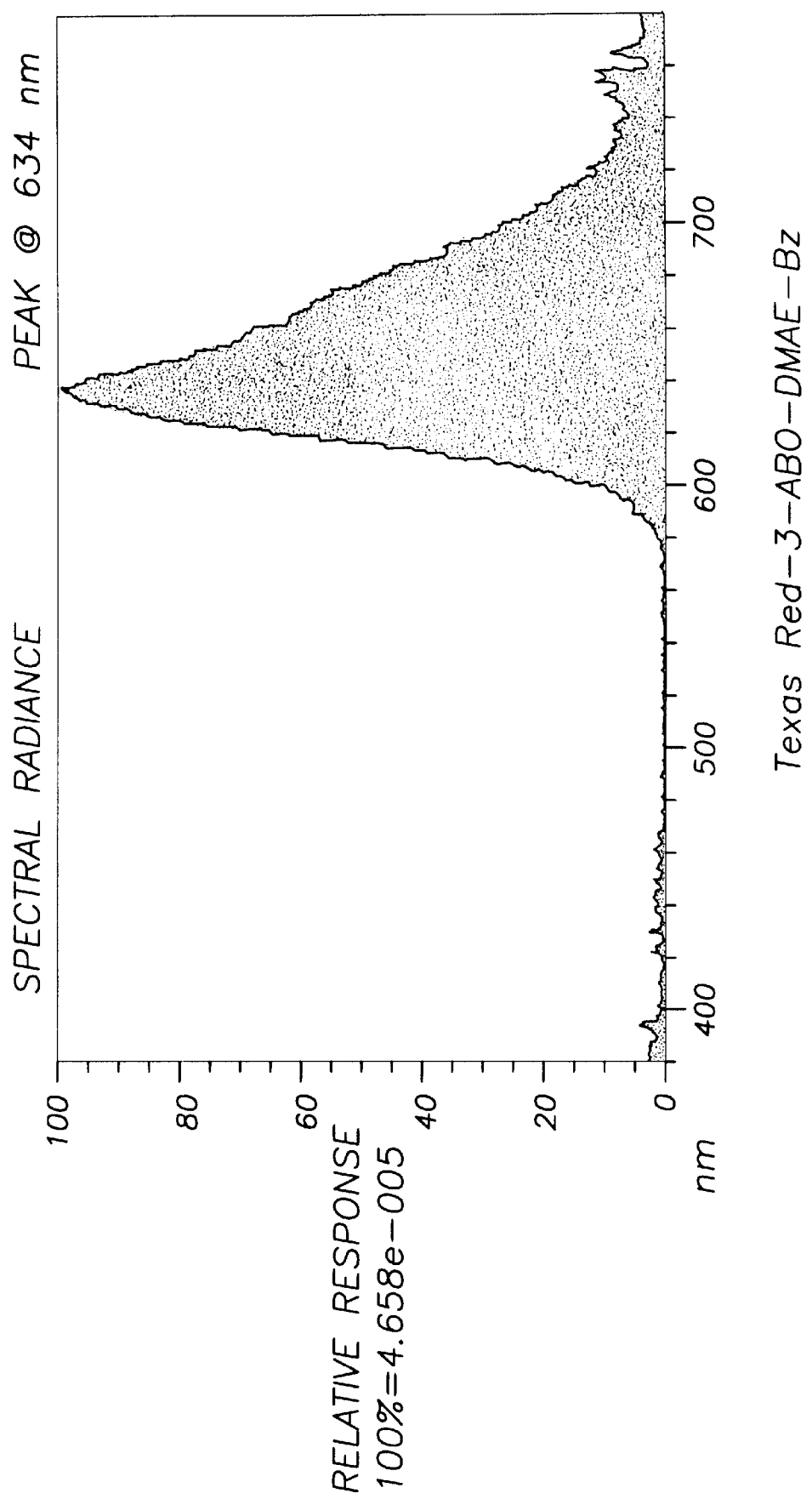
Figure 1M:
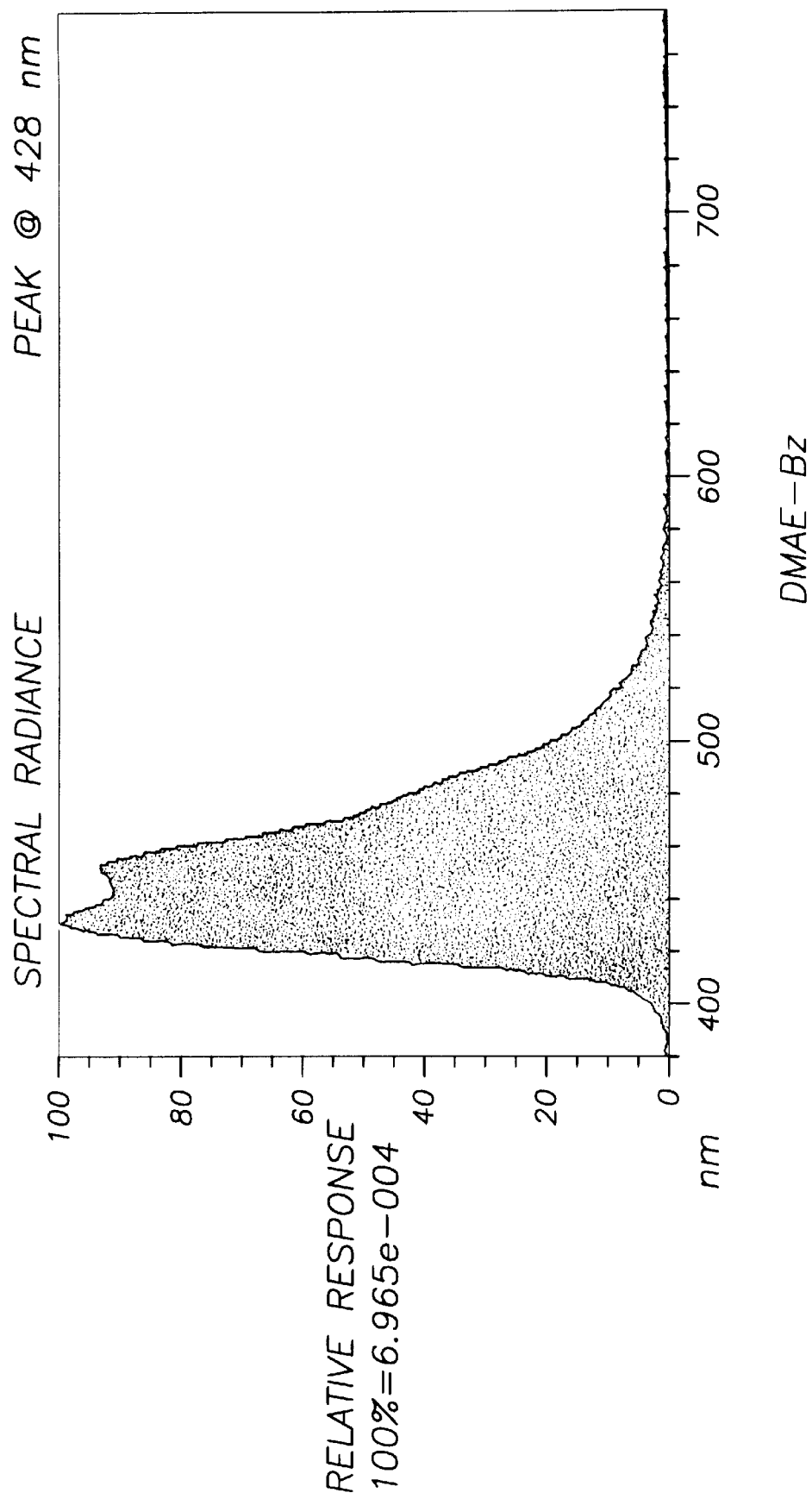
FIGS. 1M and 1N are the emission spectra of the reference compounds, DMAE-Bz and 2-MeO-LEAE-Bz.
Figure 1N:
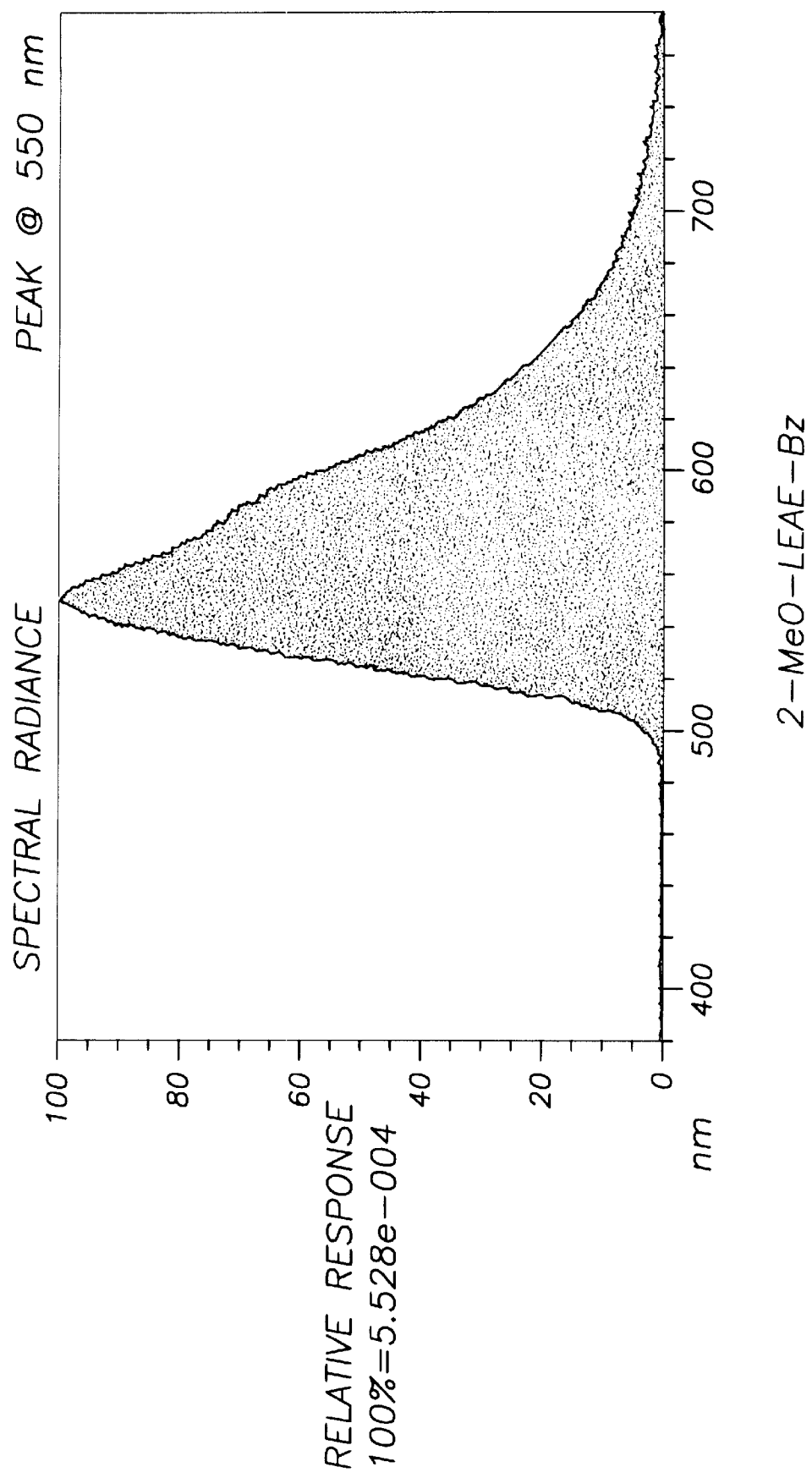

The light emission spectra of ETC's and the reference compounds DMAE-Bz and 2-MeO-LEAE-Bz were determined by a Fast Spectral Scanning System (FSSS) of Photo Research (a division of Kollmorgen Corp) of Burbank, Calif., U.S.A. The experiment was carried out in a dark room. Each compound was dissolved in acetonitrile or N,N-dimethylformamide. The resulting concentrate was diluted with the same solvent to form the working solution which upon flashing gave a light emission with an adequate intensity. A typical experiment utilized 10~100 ug of the sample in 500 ul of the solvent contained in a 13×100 mm borosilicate test tube. The tube was placed on a test tube rack raised to a proper height. A piece of aluminum foil was placed on the back of the tube to enhance the detectability of the emitted light. The FSSS optical head was placed in front of the tube at an approximate distance of 130 mm with its lens focused on the liquid in the tube. The sample solution was first treated with 0.35 ml of the Flashing Reagent #1 (Ciba-Corning Diagnostics) containing 0.1 N $HNO_3$ and 0.1% $H_2O_2$. The room was then darkened, and 0.35 ml of the Flashing Reagent #2 (Ciba-Corning Diagnostics) containing 0.25 N NaOH and 0.2% ARQUAD was added to the reaction mixture immediately. (See U.S. Pat. No. 4,927,769 which is commonly assigned and incorporated herein by reference.) The light which was generated instantaneously following the addition of the Reagent #2 was recorded by FSSS for 5 seconds starting from about one second before the Reagent #2 was added. The various emission spectra determined on FSSS are given in FIGS 1A–N, and also summarized in Table 1.

TABLE 1

| | Emission (nm) | |
|---|---|---|
| Compound | Range* | Max |
| Rhodamine-2-AM-DMAE-Bz | 590–760 | 628 |
| Rhodamine-2-AM-DMAE-CO2H | 590–740 | 620 |
| Texas Red-2-AM-DMAE-CO2H | 590–750 | 624 |

TABLE 1-continued

| Compound | Emission (nm) Range* | Max |
|---|---|---|
| CNF-2-AM-DMAE-CO2H | 670–(^) | 718 |
| Texas Red-3-AM-DMAE-CO2H | 590–720 | 612 |
| Rhodamine-3-AM-DMAE-β-Alanine | 590–750 | 620 |
| Texas Red-3-AM-DMAE-β-Alanine | 590–740 | 628 |
| Texas Red-ED-NCM-DMPAE | 590–760 | 626 |
| Texas Red-ED-NSP-DMPAE | 590–740 | 624 |
| Rhodamine-2-AM-DMAE-HD-Theophylline | 590–740 | 622 |
| Texas Red-3-APO-DMAE-Bz | 590–750 | 644 |
| Texas Red-3-ABO-DMAE-Bz | 590–750 | 634 |
| DMAE-Bz | 400–530 | 428 |
| 2-MeO-LEAE-Bz | 500–700 | 550 |

*Range is set for spectral region with signal intensity of above 5% of peak height.
^ Emission spectral range goes beyond the scanning limit (380–780 nm) of FSSS.

F. Mutually Non-Interfering Light Emission Spectra

Figure 1P:
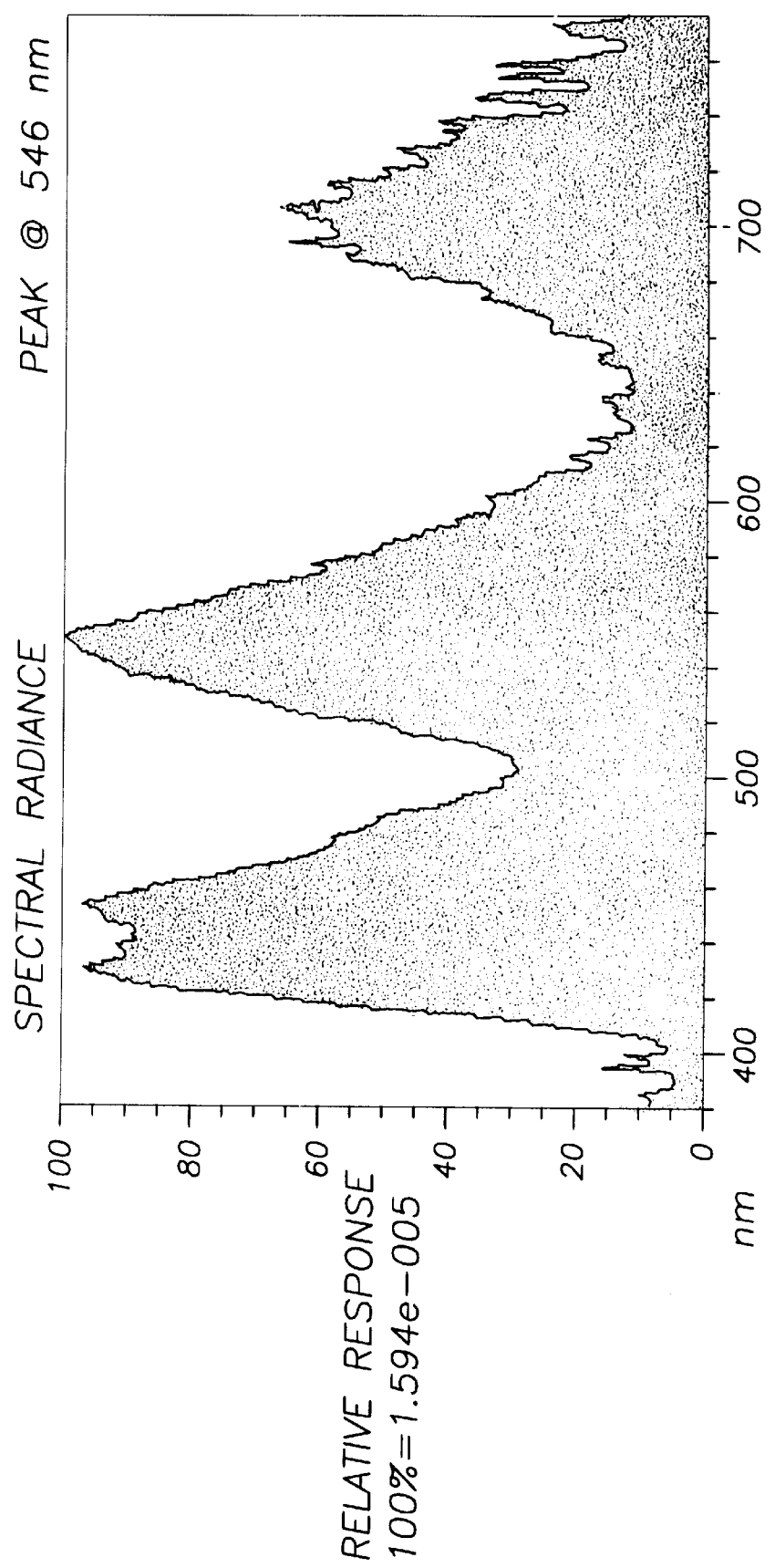
FIG. 1P is the emission spectrum of the mixture of DMAE-Bz, 2-MeO-LEAE-Bz and CNF-2-AM-DMDE-$CO_2H$.

To demonstrate mutually non-interfering light emissions among DMAE, LEAE and ETC, the mixtures of two or three of these compounds that have different emission ranges were flashed under the conditions described above. In the first experiment, a mixture of DMAE-Bz and Rhodamine-2-AM-DMAE-Bz was flashed. In the second experiment, a mixture of DMAE-Bz, 2-MeO-LEAE-Bz and CNF-2-AM-DMAE-CO$_2$H was flashed. As indicated in their respective spectra in FIGS. 1O and 1P, the emission maximum and profile of each component in the mixture are not changed.

G. Light Emission Efficiency

The light emission efficiency of representative ETCs was determined on a Berthold luminometer Magic Lite Analyzer-1 (MLA-1) (Ciba-Corning Diagnostics) without optical filter. Each sample was prepared in acetonitrile or N,N-dimethylformamide at 1 mg/ml, serially diluted to 10 ug/ml with acetonitrile or N,N-dimethylformamide, and further on with 10 mM phosphate buffer containing 0.15 M NaCl, 0.1% BSA, 0.05% NaN$_3$, pH8 to the working solution at concentration of 1 pg/ml for all the samples listed in Table 2, except for DMAE-Bz at concentration of 0.1 pg/ml.

To determine the light emission efficiency, 25 ul of blank buffer matrix or the working solution of each sample was flashed in duplicate by injecting 0.3 ml of the Flashing Reagent #1, followed after 0.1 second delay by injecting 0.3 ml of the Flashing Reagent #2. Light emission was collected for 2 seconds, and the results are given in Table 2.

Figure 2:
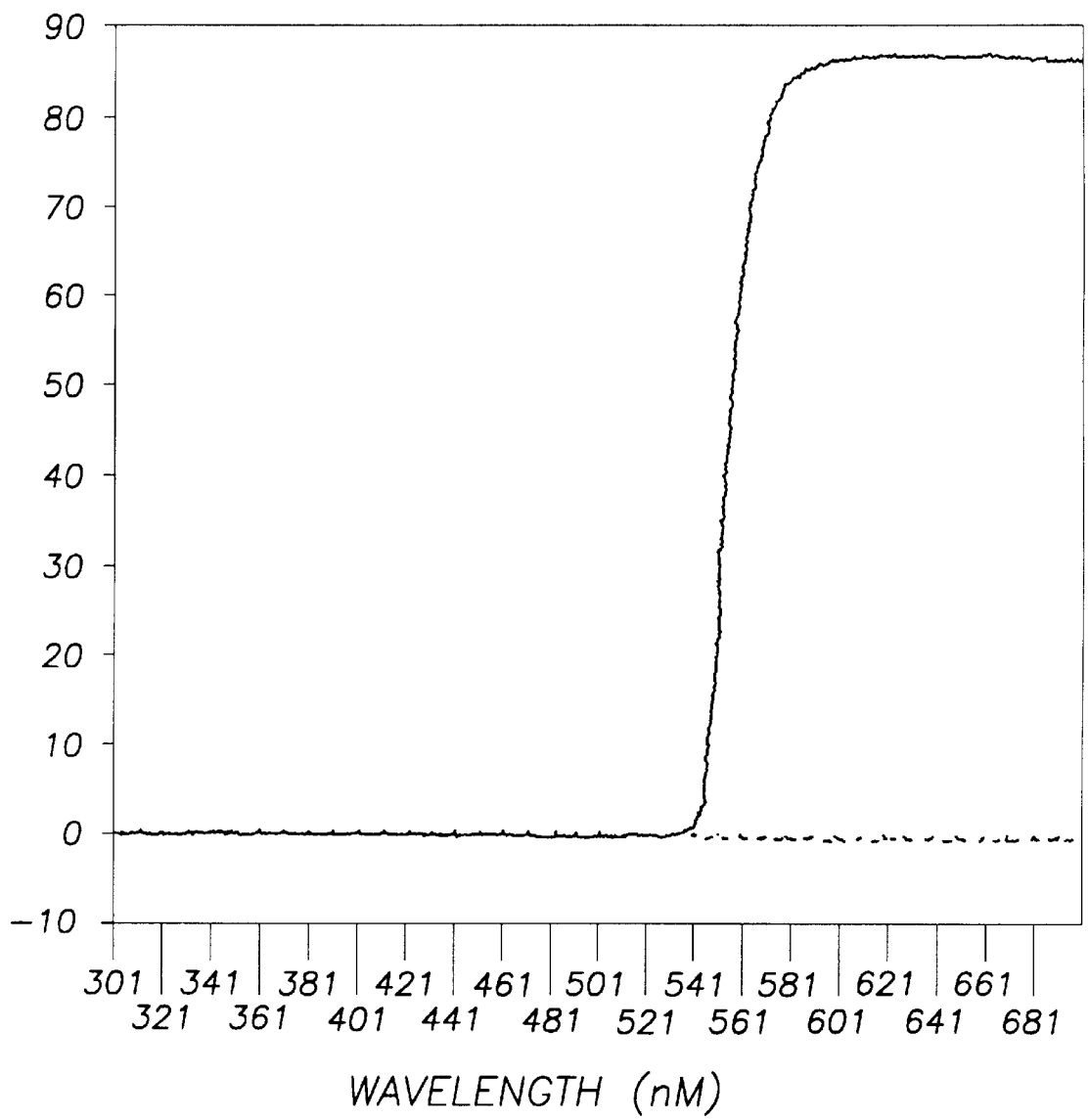
FIG. 2 is the transmittance profile of Schott's OG 550 filter.

The above measurement was also repeated by placing an OG550 filter (Schott Glass Technologies, Inc.) in front of the photo multiplier tube (PMT). The results are given in Table 2. FIG. 2 shows the transmittance profile of the OG550 filter.

Figure 3:
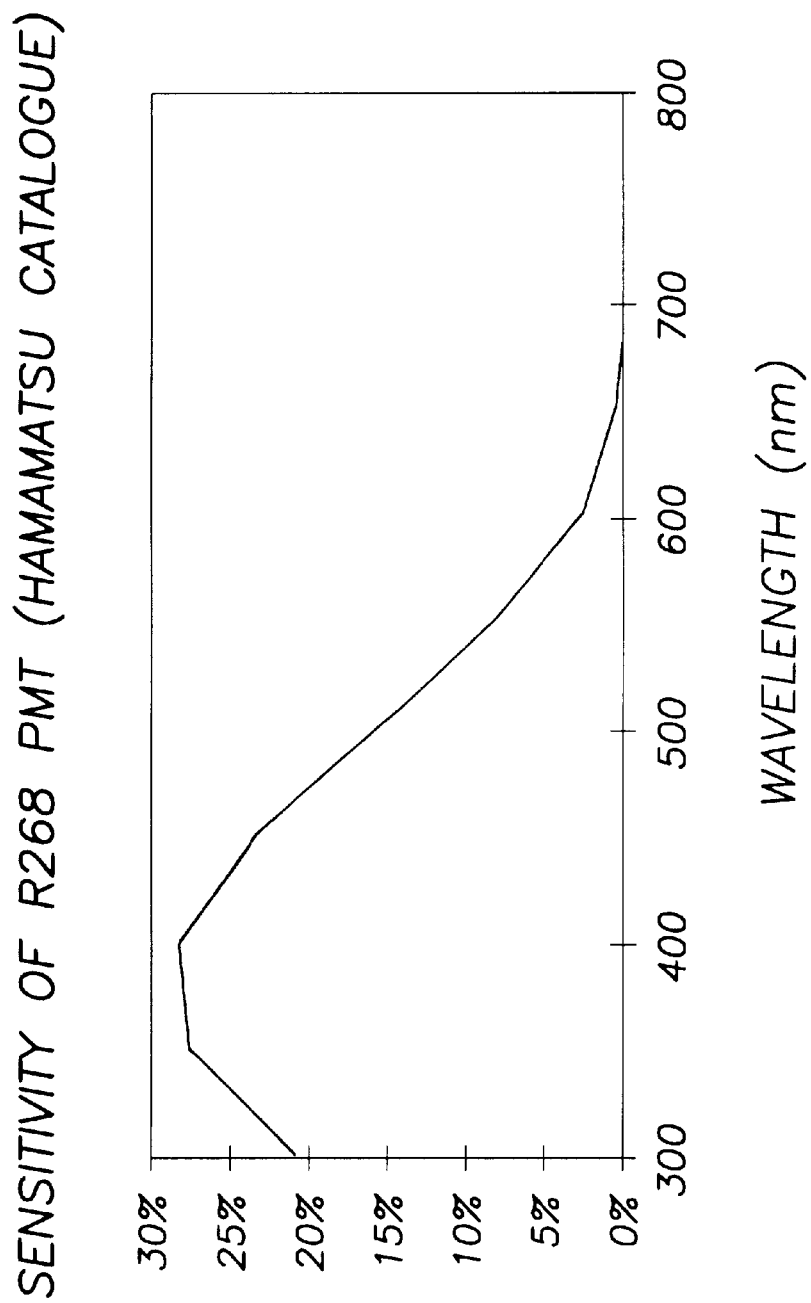
FIG. 3 is the detection efficiency of the R268 photomultiplier tube (Hamamatsu catalogue).
Figure 4:
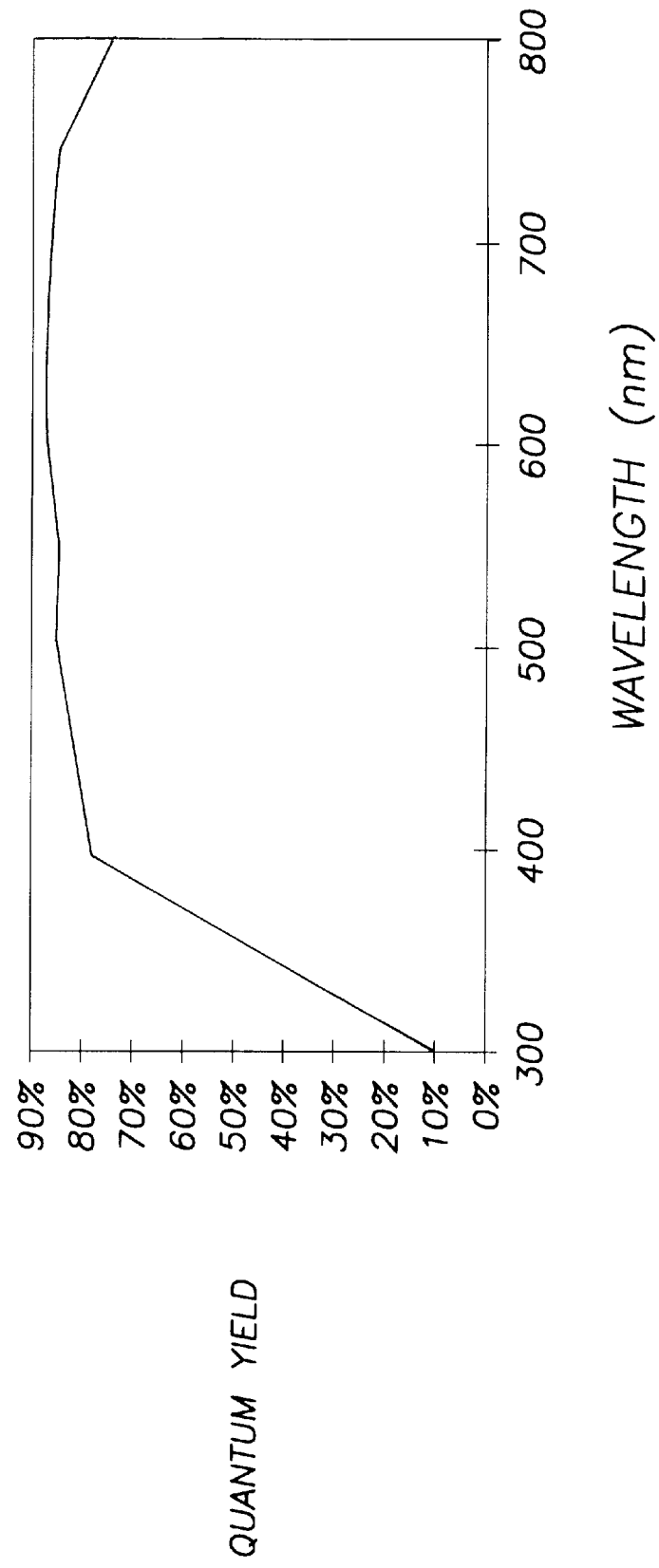
FIG. 4 is the detection efficiency of the thinned, back-illuminated Charge Coupled Device (thinned CCD).

The number of counts of the ETCs detected on MLA1 are 5~13 times lower than that of the free DMAE-Bz. As indicated in FIG. 3, the detection efficiency of the PMT used in this experiment is averagely 22% within the range of 400~500 nm where DMAE-Bz emits light, while the detection efficiency is reduced to 2~3% for the spectral region above 600 nm where all the ETCs emit their lights. This difference of detection efficiency of PMT over different wavelength regions accounts for the major loss of the detected RLUs of the ETCs. There are other light detection devices commercially available. Their detection efficiency at long wavelength region is much higher than that of PMT used in this experiment. For instance, thinned, back-illuminated Charge Coupled Device (thinned CCD) as shown in FIG. 4 can reach from 80% efficiency at 400 nm to 90% efficiency at 700 nm. Therefore, it is predicted that with the improved light detection device like thinned CCD, the light emissions of ETCs detected should increase significantly and are expected to be equal to or better than that of DMAEs.

TABLE 2

Light Emission Efficiency of ETC's Determined on MLA-1 with and without Optical Filter

| Compound | | RLU's/mol | |
|---|---|---|---|
| Filter | MW | No Filter | OG550 |
| Rhodamine-2-AM-DMAE-Bz | 1135 | 9.8 × E18 | 7.6 × E18 |
| Texas Red-2-AM-DMAE-COOH | 1115 | 7.2 × E18 | 5.2 × E18 |
| Texas Red-X-3-AM-DMAE-β-Alanine | 1300 | 1.8 × E19 | 1.3 × E19 |
| Rhodamine-2-AM-DMAE-Theophylline | 1391 | 1.4 × E19 | 1.2 × E19 |
| Rhodamine-2-AM-DMAE-COOH | 1046 | 6.4 × E18 | 3.7 × E18 |
| DMAE-Bz | 587 | 8.6 × E19 | 3.3 × E17 |

H. Flash Kinetics of Light Emission

The overall flash kinetics of the ETC's is determined by two factors: chemiluminescent kinetics of AE moiety in the conjugate as an energy donor and fluorescent kinetics of the luminophore moiety as an energy acceptor. Chemiluminescent kinetics of AE moiety of the ETC's is largely due to the nature of the electronic and/or steric effects of different substituents on the AE moiety. Therefore, the various ETC conjugates would be anticipated to have various flashing rates even under the identical conditions because of the different AE moiety. Although the energy acceptors selected in this study are luminophores having very fast kinetic, they also can be luminophores having a slow kinetic. To determine the overall flash kinetics of the ETC's, a time course study over a period of 10 seconds was conducted by flashing the ETC's and normalizing all the signals collected for different lengths of time up to 10 seconds. The results are summarized in Table 3.

TABLE 3

| Compound | Percent signal released over different lengths of time | | | | | |
|---|---|---|---|---|---|---|
| | 0.5 s | 10 s | 6 s | 4 s | 2 s | 1 s |
| Rhodamine-2-AM-DMAE-Bz | 100 | 94 | 92 | 87 | 65 | 17 |
| Rhodamine-2-AM-DMAE-COOH | 100 | 94 | 93 | 83 | 59 | 13 |
| Texas Red-2-AM-DMAE-COOH | 100 | 98 | 101 | 104 | 107 | 42 |
| CNF-2-AM-DMAE-COOH | 100 | 98 | 93 | 87 | 56 | 11 |
| Texas Red-3-AM-DMAE-COOH | 100 | 97 | 93 | 81 | 50 | 10 |
| Rhodamine-3-AM-DMAE-β-Alanine | 100 | 93 | 87 | 83 | 69 | 29 |

TABLE 3-continued

| Compound | Percent signal released over different lengths of time | | | | | |
|---|---|---|---|---|---|---|
| 0.5 s | 10 s | 6 s | 4 s | 2 s | 1 s | |
| Texas Red-X-3-AM-DMAE-β-Alanine | 100 | 99 | 98 | 97 | 84 | 41 |
| Texas Red-ED-NCM-DMPAE[1] | 100 | 67 | 51 | 30 | 15 | 4 |
| Texas Red-ED-NSP-DMPAE[2] | 100 | 64 | 47 | 28 | 16 | 6 |
| Rhodamine-2-AM-DMAE-HD-Theophylline | 100 | 100 | 100 | 97 | 94 | 36 |
| Texas Red-3-APO-DMAE-Bz | 100 | 97 | 94 | 91 | 80 | 35 |
| Texas Red-3-ABO-DMAE-Bz | 100 | 94 | 92 | 88 | 74 | 35 |
| DMAE-Bz | 100 | 99 | 96 | 80 | 48 | 10 |

[1,2]: Compounds having a very slow flash kinetics with $t_{1/2}$ much greater than 10 seconds.

EXAMPLES

Example 1

Synthesis of Rhodamine-2-AM-DMAE-Bz

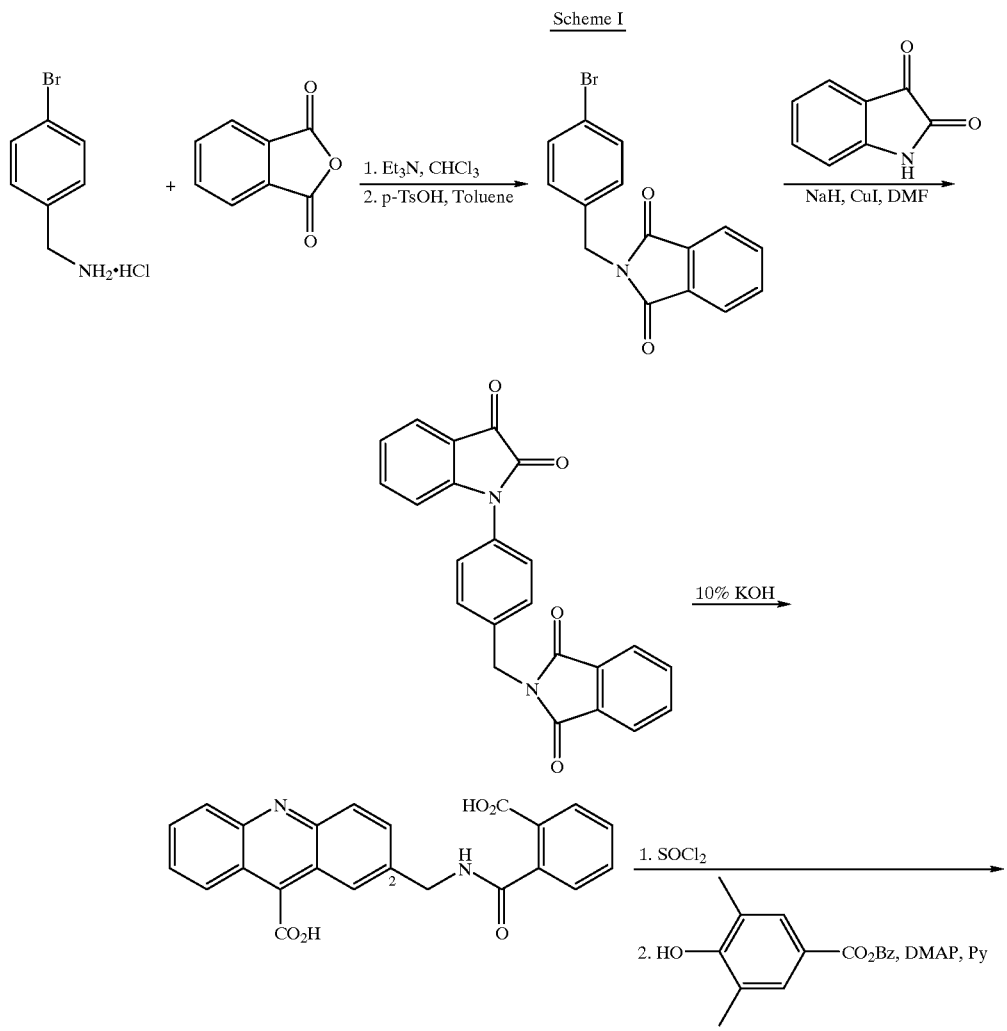

Scheme I

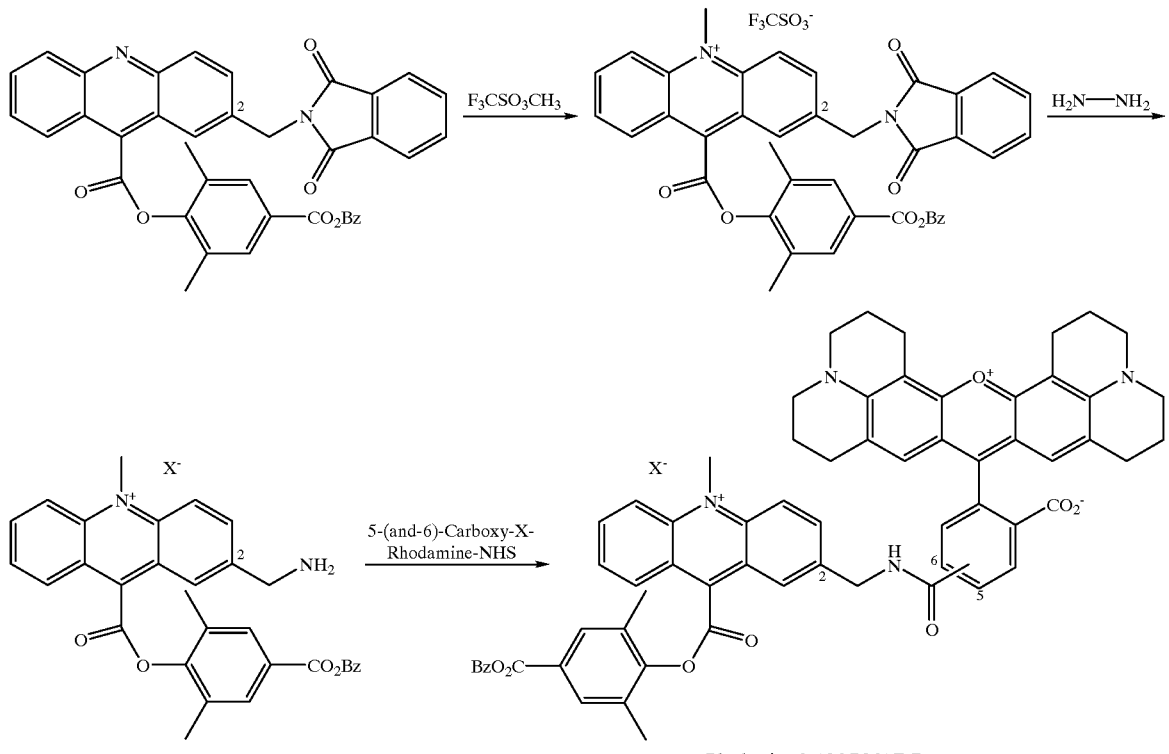

Rhodamine-2-AM-DMAE-Bz

X⁻ = CF₃COO⁻ after the compound was recovered from HPLCmobile phase containing CF3COOH 4-Phthalimidomethyl bromobenzene To a suspension of 10 g (44.94 mmol) of 4-bromobenzylamine hydrochloride in 200 ml of chloroform was added 12.5 ml (89.62 mmol) of triethylamine, followed by the addition of 8.99 g (60.67 mmol) of phthalic anhydride. The mixture was stirred at room temperature for 10 minutes to give a homogeneous solution, which was then heated at 75° C. for three hours. The reaction mixture was then evaporated to remove the chloroform and the residue was suspended in 400 ml of toluene followed by adding 700 mg of p-toluenesulfonic acid monohydrate. The resulting mixture was briefly refluxed at 140° C., and additional 3 ml of triethylamine was added to form a homogeneous solution. The solution was refluxed at 140° C. for 2 hours; and the water formed was collected through a Dean-Stark trap apparatus. The solution was then cooled to room temperature, washed with 3% sodium hydroxide (2×200 ml), water (1×200 ml), brine (1×200 ml), and dried over sodium sulfate. Removal of the solvent under reduced pressure gave 12.07 g (85% yield) of 4-phthalimidomethyl bromobenzene as a white solid. Rf: 0.6 (silica gel, ethyl acetate:hexane=1:2). $^1$H NMR (CDCl$_3$): δ ppm 4.79 (2H, s), 7.31, 7.44 (2H each, AA'BB'), 7.73, 7.84 (2H each, m).

N-(4-Phthalimidomethyl)phenyl isatin

A solution of 1.863 g (12.66 mmol) of isatin in 80 ml of anhydrous N,N-dimethylformamide (DMF) was treated at room temperature with 0.608 g (15.19 mmol) of sodium hydride (60% dispersion) for about 40 minutes until the formation of the hydrogen bubble ceased. Then, cuprous iodide (CuI, 5.303 g, 27.85 mmol) and 4-phthalimidomethyl bromobenzene (6 g, 18.99 mmol) were added; the reaction was allowed to stir under nitrogen at 160° C. for 16 hours. The reaction was cooled down to room temperature and mixed with 400 ml of chloroform. The resulting mixture was filtered. The filtrate was evaporated to dryness under reduced pressure and the residue was separated on a silica flash column (5 to 20% ether/toluene) to give the desired product in 1.76 g (36.4% yield). Rf: 0.2 (silica gel, 10% ether/toluene). MS (MALDI-TOF): m/z 384.437 (observed).

2-(2'-Carboxybenzamido)methyl-acridine-9-carboxylic acid

A mixture of 1.26 g (3.3 mmol) of N-(4-phthalimidomethyl)phenyl isatin in 70 ml of 10% KOH was stirred at 120° C. for 2 hours. The resulting solution was diluted into 250 ml in water and then acidified in an ice bath to give the yellow precipitate. The precipitate was collected, washed with water and air-dried to give 1.26 g (87.5% yield) of the title compound as a yellow solid. Rf: 0.5 (silica gel, CHCl$_3$/MeOH/H$_2$O=55:45:4). MS (MALDI-TOF): m/z 401.577 (M+1).

(4'-Benzyloxycarbonyl-2',6'-dimethyl)phenyl 2-phthalimidomethyl-acridine-9-carboxylate 2-(2'-Carboxybenzamido)methyl-acridine-9-carboxylic acid (905 mg, 2.29 mmol) was refluxed in 10 ml of thionyl chloride for 2 hours. After cooled to room temperature, the solution was reduced to about a half of the volume by blowing with nitrogen and then poured into 75 ml of anhydrous ether. The yellow precipitate was collected and washed with ether (3×20 ml). After dried under vacuum, the yellow solid was suspended in 30 ml of anhydrous pyridine, followed by the addition of 515.8 mg (2.01 mmol) of benzyl 3,5-dimethyl-4-hydroxybenzoate and 100 mg (0.41 mmol) of N,N-dimethylaminopyridine (DMAP). The reaction was stirred at 110° C. for 2 hours and then at 55° C. for another 16 hours. After cooled to room temperature, the mixture was filtered. The filtrate was evaporated to dryness under reduced pressure, and the residue was separated on a silica flash column (2 to 5% ethylacetate/methylenechloride) to give 115 mg (20% yield based on the recovery of the starting material) of the desired product. Rf: 0.5 (silica gel, 10% EtOAc/CH$_2$Cl$_2$). MS (MALDI-TOF): m/z 620.206 (observed).

(4'-Benzyloxycarbonyl-2',6'-dimethyl)phenyl 2-phthalimidomethyl-10-methyl-acridinium-9-carboxylate trifluorosulfonate A solution of (4'-benzyloxycarbonyl-2',6'-dimethyl) phenyl 2-phthalimidomethyl-acridine-9-carboxylate (317.39 mg, 0.512 mmol) in 15 ml of anhydrous methylenechloride was treated with methyl trifluoromethanesulfonate (0.58 ml, 5.12 mmol). The reaction was stirred under nitrogen at room temperature for 16 hours. The solvent was then removed by blowing with nitrogen. The residue was purified on a reverse phase HPLC column (YMC, Wilmington, N.C., 30×500 mm, ODS-A, S-10, 120 Å). The product was eluted at retention time of 19 min in step gradient by mixing 0.05% TFA/H$_2$O (solvent A) and 0.05% TFA/CH$_3$CN (solvent B) in the following manner: 60% B to 100% B in 30 min; flow rate at 30 ml/min; monitored at 260 nm. The removal of the solvents gave 326.6 mg (85% yield) of the title compound. Rf: 0.7 (silica gel, ether). MS (ESI): m/z 635 (M).

(4'-Benzyloxycarbonyl-2',6'-dimethyl)phenyl 2-aminomethyl-10-methyl-acridinium-9-carboxylate trifluoroacetate A solution of (4'-benzyloxycarbonyl-2',6'-dimethyl) phenyl 2-phthalimidomethyl-10-methyl-acridinium-9-carboxylate trifluoromethanesulfonate (17.2 mg, 0.023 mmol) and hydrazine (21.7 ul, 0.69 mmol) in 3 ml of anhydrous DMF was stirred at room temperature for 16 hours. The reaction mixture was then separated on a Beckman prep-60 ADD-ON HPLC system (YMC, Wilmington, N.C., 300×20 mm, ODS-A, S-10, 120 Å). The desired product (4.6 mg, 31% yield) was eluted at retention time of 20 min in step gradient by mixing 0.05% TFA/H$_2$O (solvent A) and 0.05% TFA/CH$_3$CN (solvent B) in the following manner: 30% B for 15 min, then to 60% B in 5 min and further for 20 min; flow rate at 20 ml/min; monitored at 260 nm. MS(ESI): m/z 505 (M).

Rhodamine-2-AM-DMAE-Bz

To a solution of 8.89 mg (0.0144 mmol) of (4'-benzyloxycarbonyl-2',6'-dimethyl)phenyl 2-aminomethyl-10-methyl-acridinium-9-carboxylate trifluoroacetate in 1 ml of anhydrous DMF was added 9.81 ul (0.0704 mmol) of triethylamine and 16.68 mg (0.0264 mmol) of 5-(and -6)-carboxy-X-Rhodamine, succinimidyl ester, sequentially. The reaction was then stirred at room temperature for 16 hours. The product was isolated on a Beckman analytical HPLC Model 126 (Columbia, Md.) with Phenomenex reversed phase semi-prep column (Torrance, Calif., 300×7.8 mm, Bondclone C18 10 mm). It was eluted at retention time of 30 min in step gradient by mixing 0.05% TFA/H$_2$O (solvent A) and 0.05% TFA/CH$_3$CN (solvent B) in the following manner: 30% B to 60% B in 30 min, at 60% B for another 10 min; flow rate 2 ml/min; monitored at 260 nm. The product was obtained in 2.56 mg (17.4% yield). MS(ESI): m/z 1022(M).

Example 2

Synthesis of Texas Red-2-AM-DMAE-COOH

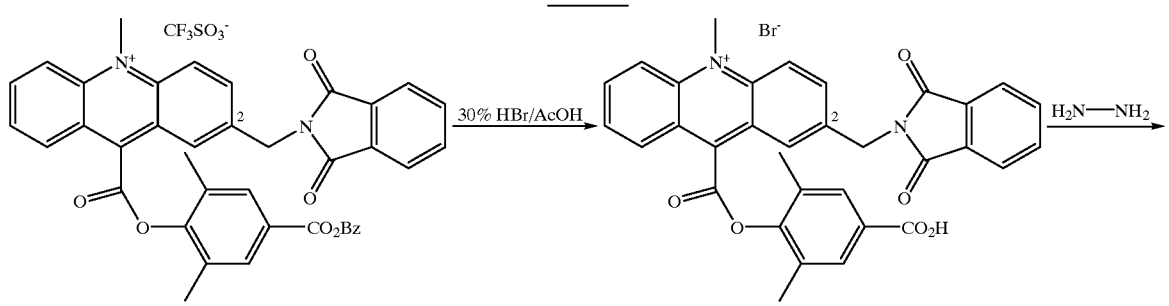

Scheme II

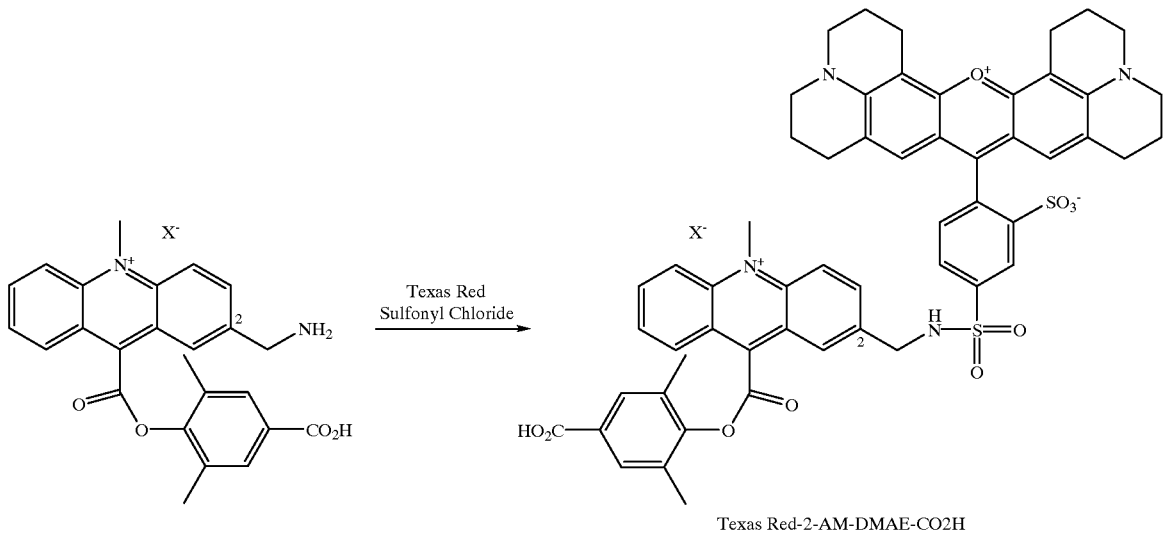

X⁻ = CF3COO⁻ after the compound was recovered from HPLC mobile phase containing CF3COOH (4'-Carboxyl-2',6'-dimethyl)phenyl 2-phthalimidomethyl-10-methyl-acridinium-9-carboxylate bromide A mixture of 200 mg (0.255 mmol) of (4'-benzyloxycarbonyl-2',6'-dimethyl)phenyl 2-phthalimidomethyl-10-methyl-acridinium-9-carboxylate trifluoromethanesulfonate in 4 ml of 30% HBr/AcOH was stirred at 55° C. for 2 hours. After cooled to room temperature, the reaction mixture was blown with nitrogen to reduce the volume to about 1 ml. and then poured into 15 ml of ether. The precipitate was collected and washed with excess amount of ether. After air-dried, 150 mg (89.5% yield) of the product was obtained as an orange solid. This product was analyzed on a Phenomenex reversed phase HPLC column (Torrance, Calif., 300×3.90 mm, Bondclone C18 10 mm). It was eluted at retention time 23.6 min in step gradient by mixing 0.05% TFA/H$_2$O (solvent A) and 0.05% TFA/CH$_3$CN (solvent B) in the following manner: 30% B for 15 min, then to 60% B in 5 min and further for 20 min; flow rate at 1 ml/min; monitored at 260 nm. MS (ESI): m/z 545 (M).

(4'-Carboxyl-2',6'-dimethyl)phenyl 2-aminomethyl-10methyl-acridinium-9-carboxylate trifluoroacetate A solution of (4'-carboxyl-2',6'-dimethyl)phenyl 2-phthalimidomethyl-10-methyl-acridinium-9-carboxylate bromide (130 mg, 0.21 mmol) and hydrazine (104.5 ul, 3.33 mmol) 4 ml of DMF was stirred at room temperature for 2 hours. The reaction was then separated on a Beckman prep-60 ADD-ON HPLC system (YMC, Wilmington, N.C., 300×20 mm, ODS-A, S-10, 120 Å). The desired product was eluted as a major peak at retention time of 20 minutes in step gradient by mixing 0.05% TFA/H$_2$O (solvent A) and 0.05% TFA/CH$_3$CN (solvent B) in the following manner: 5% B to 60% B in 30 min, at 60% B for another 5 min; flow rate at 25 ml/min; monitored at 260 nm. Removal of the solvents gave 56 mg (51% yield) of the product. MS (ESI): m/z 415 (M).

Texas Red-2-AM-DMAE-COOH

A solution of (4'-carboxyl-2',6'-dimethyl)phenyl 2-aminomethyl-10-methyl-acridinium-9-carboxylate trifluoroacetate (2.4 mg, 0.0045 mmol) and Texas Red sulfonyl chloride (15 mg) in 1 ml of anhydrous DMF containing 6.34 ul of Et$_3$N was stirred at room temperature under nitrogen for 16 hours. The reaction was then separated on a Beckman prep-60 ADD-ON HPLC system (YMC, Wilmington, N.C., 300×20 mm, ODS-A, S-10, 120 Å). The desired product (1.5 mg) was eluted at retention time of 30 min in step gradient by mixing 0.05% TFA/H$_2$O (solvent A) and 0.05% TFA/CH$_3$CN (solvent B) in the following manner: 5% B to 60% B in 30 min, at 60% B for another 5 min; flow rate at 16 ml/min; monitored at 260 nm. MS(ESI): m/z 1003 (M+1).

Example 3

Synthesis of Rhodamine-2-AM-DMAE-COOH

Scheme III

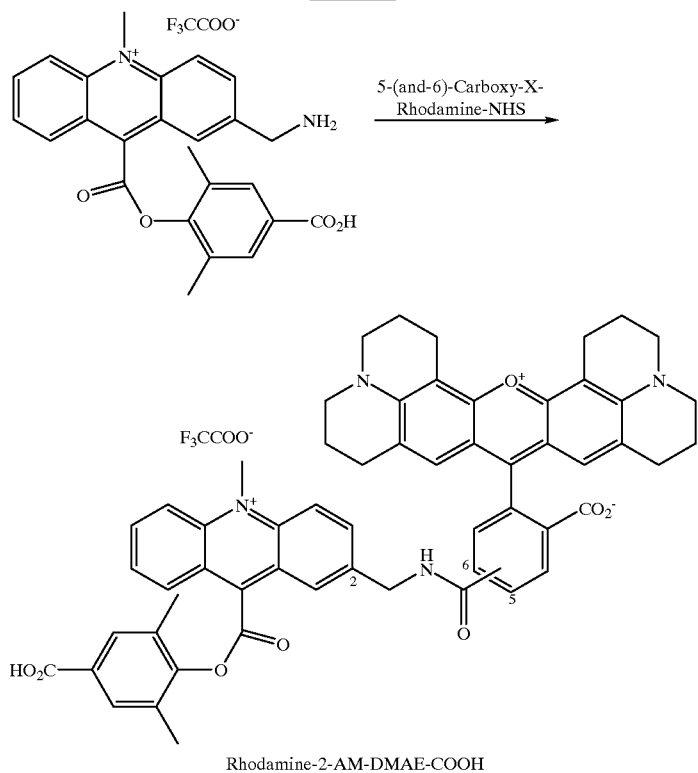

Rhodamine-2-AM-DMAE-COOH

10 To a solution of (4'-carboxyl-2',6'-dimethyl)phenyl 2-aminomethyl-10-methyl-acridinium-9-carboxylate trifluoroacetate (5 mg, 0.0095 mmol) in 2 ml of anhydrous DMF were added triethylamine (19.8 ul, 0.142 mmol) followed by addition of 5-(and -6)-carboxy-X-Rhodamine, succinimidyl ester (17.96 mg, 0.0284 mmol). The reaction was stirred at room temperature for 16 hours. The product was isolated on a Beckman analytical HPLC Model 126 (Columbia, Md.) with Phenomenex reversed phase semi-prep column (Torrance, Calif., 300×7.8 mm, Bondclone C18 10 mm). It was eluted at retention time of 37.2 min in step gradient by mixing 0.05% TFA/H$_2$O (solvent A) and 0.05% TFA/CH$_3$CN (solvent B) in the following manner: at 25% B for 10 min, then to 55% B in 30 min, then to 100% B in 5 min; flow rate at 16 ml/min; monitored at 260 nm. The product was obtained in 2 mg. MS (MALDI-TOF): m/z 934.25 (M+1).

Example 4

Synthesis of CNF-2-AM-DMAE-COOH

Scheme IV

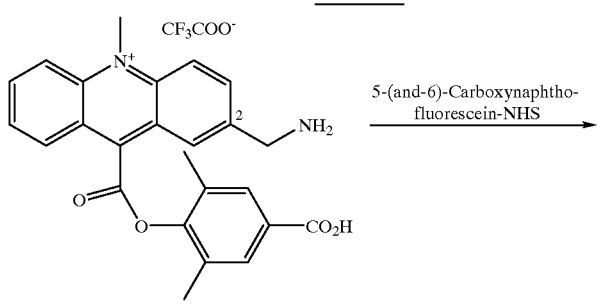

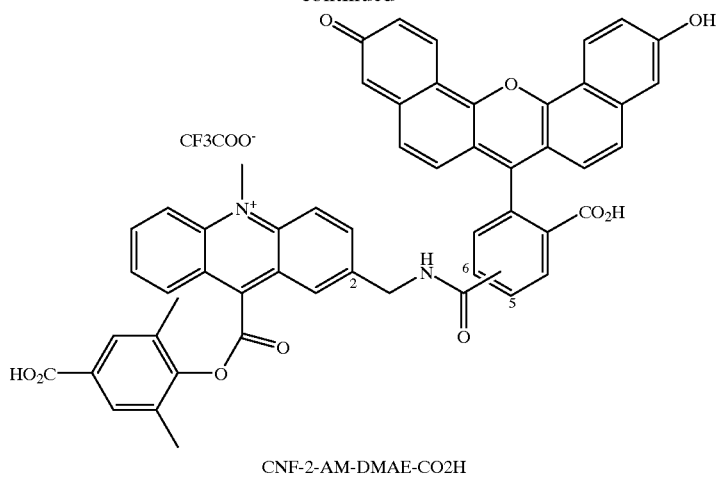

CNF-2-AM-DMAE-CO2H

A solution of 8.7 mg (0.013 mmol) of (4'-carboxyl-2',6'-dimethyl)phenyl 2-aminomethyl-10-methyl-acridinium-9-carboxylate trifluoroacetate and 4 mg (0.0062 mmol) of 5-(and-6-)-carboxynaphthofluorescein, succinimidyl ester in 1 ml of anhydrous DMF containing 5.3 ul (0.031 mmol) of $Et_3N$ was stirred at room temperature under nitrogen for 16 hours. The reaction was then separated on a Beckman prep-60 ADD-ON HPLC system (YMC, Wilmington, N.C., 300×20 mm, ODS-A, S-10, 120 Å). The desired product (1.5 mg) was eluted at retention time of 32 min in step gradient by mixing 0.05% TFA/$H_2O$ (solvent A) and 0.05% TFA/$CH_3CN$ (solvent B) in the following manner: 20% B to 50% B in 30 min, at 50% B for another 10 min; flow rate at 10 ml/min; monitored at 260 nm. MS(ESI): m/z 873.

Example 5

Synthesis of Texas Red-3-AM-DMAE-COOH

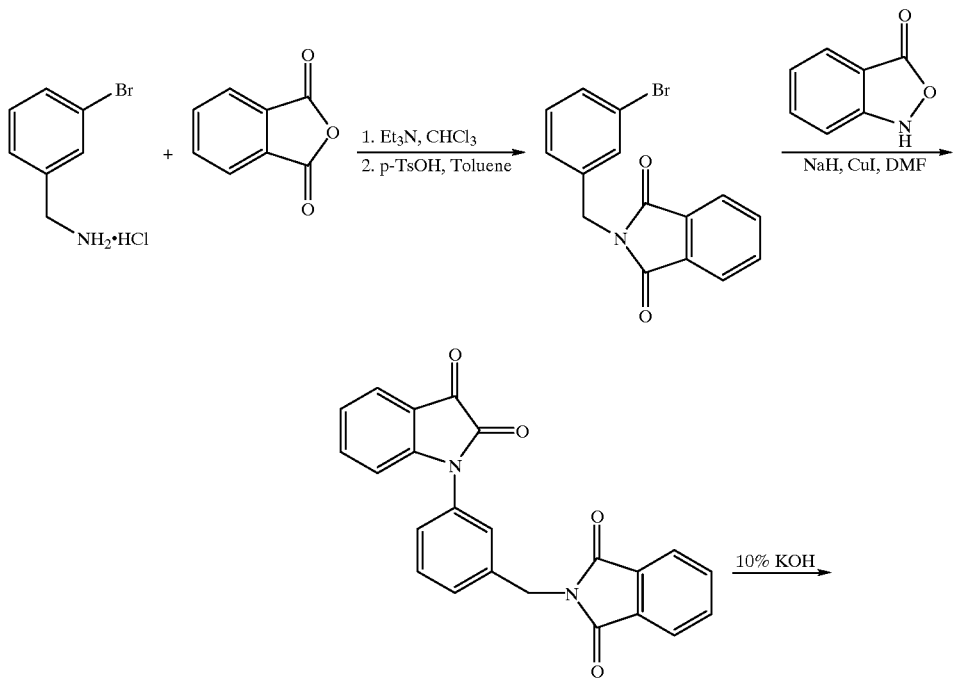

Scheme V

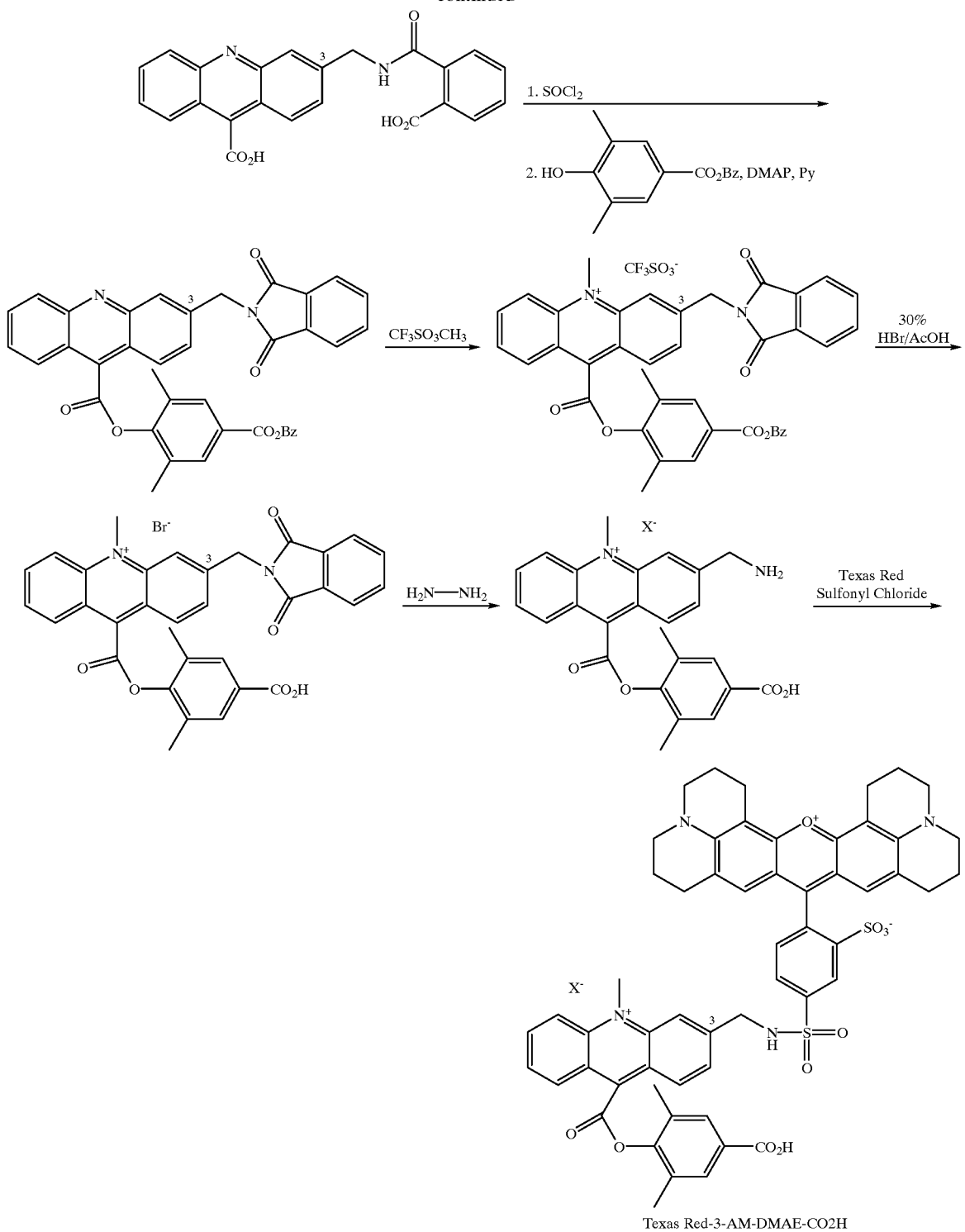

X⁻ = CF3COO⁻ after the compound was recovered from HPLC mobile phase containing CF3COOH 3-Phthalimidomethyl bromobenzene A mixture of 3-bromobenzylamine hydrochloride (10 g, 45 mmol), phthalic anhydride (9.33 g, 63 mmol) and triethylamine (12.5 ml, 90 mmol) in 200 ml of toluene was refluxed at 130° C. for 13 hours, and the water formed in the reaction was collected via a Dean Stark trap apparatus. The reaction was then cooled to room temperature and another 200 ml of toluene was added followed by the addition of 1 g of p-toluenesulfonic acid monohydrate. The resulting mixture was further refluxed at 130° C. for 3 hours with the Dean-Stark trap apparatus. The mixture was cooled to room temperature, and washed with 3% sodium hydroxide solution (3×200 ml), water (3×200 ml), brine (1×200 ml) and dried over magnesium sulfate. Removal of the solvent gave 13.2 g (92% yield) of the desired product. Rf: 0.7 (silica gel, 30% ether/hexane). $^1$H NMR (CDCl$_3$): δ ppm 4.77 (2H, s), 7.15 (1H, t, J=7.8 Hz), 7.34 (2H, t, J=7.8 Hz), 7.53 (1H, s), 7.68 (2H, m), and 7.82 (2H, m).

N-(3-Phthalimidomethyl)phenyl isatin

A solution of isatin (2.17 g, 14.77 mmol) in 200 ml of anhydrous DMF was treated with NaH (60% dispersion, 0.709 g, 17.72 mmol) at room temperature for half an hour. The resulting brown mixture was treated with 3-phthalimidomethyl bromobenzene (7 g, 22.15 mmol) and cuprous iodide (5.61 g, 29.54 mmol). The mixture was heated at 160° C. under nitrogen for 18 hours. After cooled to room temperature, the mixture was diluted with 800 ml of chloroform. The resulting mixture was filtrated; the filtrate was evaporated under reduced pressure to give the crude product as a brown material. Rf: 0.9 (silica gel, 20% ether/hexane).

3-(2'-Carboxybenzamido)methyl-acridine-9-carboxylic acid

The crude N-(3-phthalimidomethyl)phenyl isatin was refluxed in 200 ml of 10% potassium hydroxide at 130° C. for 3 hours. After cooled to room temperature, the mixture was filtrated. The filter cake was washed with 20 ml of 10% potassium hydroxide. The combined filtrate was acidified in an ice bath with concentrated hydrochloric acid with stirring to pH 1~2. The resulting solid was washed with water (4×100 ml), air-dried and further dried over phosphorus pentoxide at 100° C. overnight, to give the desired product in 5.36 g (yield: 91% from isatin). Rf: 0.5 (silica gel, chloroform/methanol/water 55:45:5). MS (MALDI-TOF): m/z 401.665 (M+1).

(4'-Benzyloxycarbonyl-2',6'-dimethyl)phenyl 3-phthalimidomethyl-acridine-9-carboxylate A mixture of 3-(2'-carboxybenzamido)methyl-acridine-9-carboxylic acid (3.1 g) in thionyl chloride (60 ml) was heated at 110° C. for an hour to form a homogeneous solution, which was further heated for additional 1.5 hours. The reaction mixture was cooled to room temperature and reduced to about 30 ml on water respirator. The resulting concentrate was poured into 150 ml of anhydrous ether. The precipitate was collected, washed with ether (2×50 ml) and dried under vacuum to give the light-brown product, 1.91 g (57% yield). This material (1.91 g, 4.38 mmol) was dissolved in 100 ml of anhydrous pyridine, and treated with benzyl 3,5-dimethyl-4-hydroxybenzoate (1.12 g, 4.38 mmol) at room temperature under nitrogen with stirring for 15 hours. The solution was then evaporated under reduced pressure to dryness. The residue was separated on a silica flash chromatography column by elution with 4 liters of 25% ethyl acetate in hexane. The fractions containing the desired product was combined. Removal of the solvents under reduced pressure gave the title compound in 470 mg (yield: 17%). Rf: 0.8 (silica gel, 10% methanol/chloroform). MS (ESI): m/z 621.3 (M+1).

(4'-Benzyloxycarbonyl-2',6'-dimethyl)phenyl 3-phthalimidomethyl-10-methyl-acridinium-9-carboxylate trifluorosulfonate A solution of (4'-benzyloxycarbonyl-2',6'-dimethyl) phenyl 3-phthalimidylmethyl-acridinie carboxylate (100 mg, 0.1613 mmol) in 5 ml of anhydrous methylene chloride was treated with methyl trifluoromethylsulfonate (182 ml, 1.613 mmol). The solution was stirred at room temperature under nitrogen for 16 hours. The volume of the resulting mixture was reduced to about 2 ml by blowing with nitrogen. The resulting mixture was treated with 10 ml of anhydrous ether. The precipitate was collected and washed with ether (5×5 ml), to give 110 mg (87%) of the bright-yellow product. MS (ESI): m/z 635.6 (M$^+$).

(4'-Carboxy-2',6'-dimethyl)phenyl 3-phthalimidomethyl-10-methyl-acridinium-9-carboxylate bromide A mixture of (4'-benzyloxycarbonyl-2',6'-dimethyl) phenyl 3-phthalimidylmethyl-10-methyl-acridinium-9-carboxylate trifluorosulfonate (105 mg) in 2 ml of 30% hydrogen bromide in acetic acid was heated with stirring at 55° C. for 2 hours. After cooled to room temperature, the mixture was treated with 20 ml of anhydrous ether. The yellow precipitate was collected and washed with ether (6×5 ml) to afford 90 mg of the product quantitatively. MS (ESI): m/z 545.7 (M$^+$).

(4'-Carboxyl-2',6'-dimethyl)phenyl 3-aminomethyl-10-methyl-acridinium-9-carboxylate trifluoroacetate A solution of (4'-carboxy-2',6'-dimethyl)phenyl 3-phthalimidomethyl-10-methyl-acridinium-9-carboxylate bromide (60 mg, 0.112 mmol) and hydrazine (60.4 ul, 1.927 mmol) in 2 ml of DMF was stirred at room temperature under nitrogen for 4 hours to give a suspension. The filtration removed the solid, and the filtrate was evaporated under reduced pressure to dryness. The residue was separated on a Beckman prep-60 ADD-ON HPLC system (YMC, Wilmington, N.C., 300×20 mm, ODS-A, S-10, 120 Å), eluted in step gradient by mixing 0.05% TFA/H$_2$O (solvent A) and 0.05% TFA/CH$_3$CN (solvent B) in the flowing manner: 5% B to 60% B in 30 min; flow rate at 16 ml/min; monitored at 260 nm. The desired product was eluted as a broad peak at retention time of 23.5 min to 25.2 min. Removal of the solvents under reduced pressure afforded 21 mg (yield: 36%) of the desired product.

$^1$H NMR (MeOD-d4): δ ppm 1.60 (6H, s), 3.57 (3H, s), 4.20 (2H, s), 7.10 (1H, dt, J$_1$=7.8 Hz, J$_2$=0.8 Hz), 7.16 (dd, J$_1$=8.0 Hz, J$_2$=1.6 Hz), 7.29 (d, J=8.4 Hz), 7.35 (d, J=1.2 Hz), 7.48 (dt, J$_1$=7.2 Hz, J$_2$=1.6 Hz), 7.58 (2H, s), 7.60 (dd, J$_1$=7.8 Hz, J$_2$=1.6 Hz), and 7.66 (d, J=7.9 Hz).

Texas Red-3-AM-DMAE-COOH

A solution of (4'-carboxy-2',6'-dimethyl)phenyl 3-aminomethyl-10-methyl-acridinium-9-carboxylate trifluoroacetate (12 mg, 0.027 mmol) in 1 ml of anhydrous DMF containing 31.7 ul (0.27 mmol) of Et$_3$N was treated with Texas Red sulfonyl chloride (30 mg, 0.0475 mmol) with stirring at room temperature under nitrogen for 16 hours. The reaction mixture was separated on a Beckman prep-60 ADD-ON HPLC system (YMC, Wilmington, N.C., 300×20 mm, ODS-A, S-10, 120 Å). The desired product (3.4 mg) was eluted at retention time of 33 min in step gradient by mixing 0.05% TFA/H$_2$O (solvent A) and 0.05% TFA/ CH$_3$CN (solvent B) in the following manner: 5% B to 60% B in 30 min, at 60% B for another 5 min; flow rate at 16 ml/min; monitored at 260 nm. MS(ESI): m/z 1003 (M+1).

Example 6

Synthesis of Rhodamine-3-AM-DMAE-β-Alanine

Scheme VI

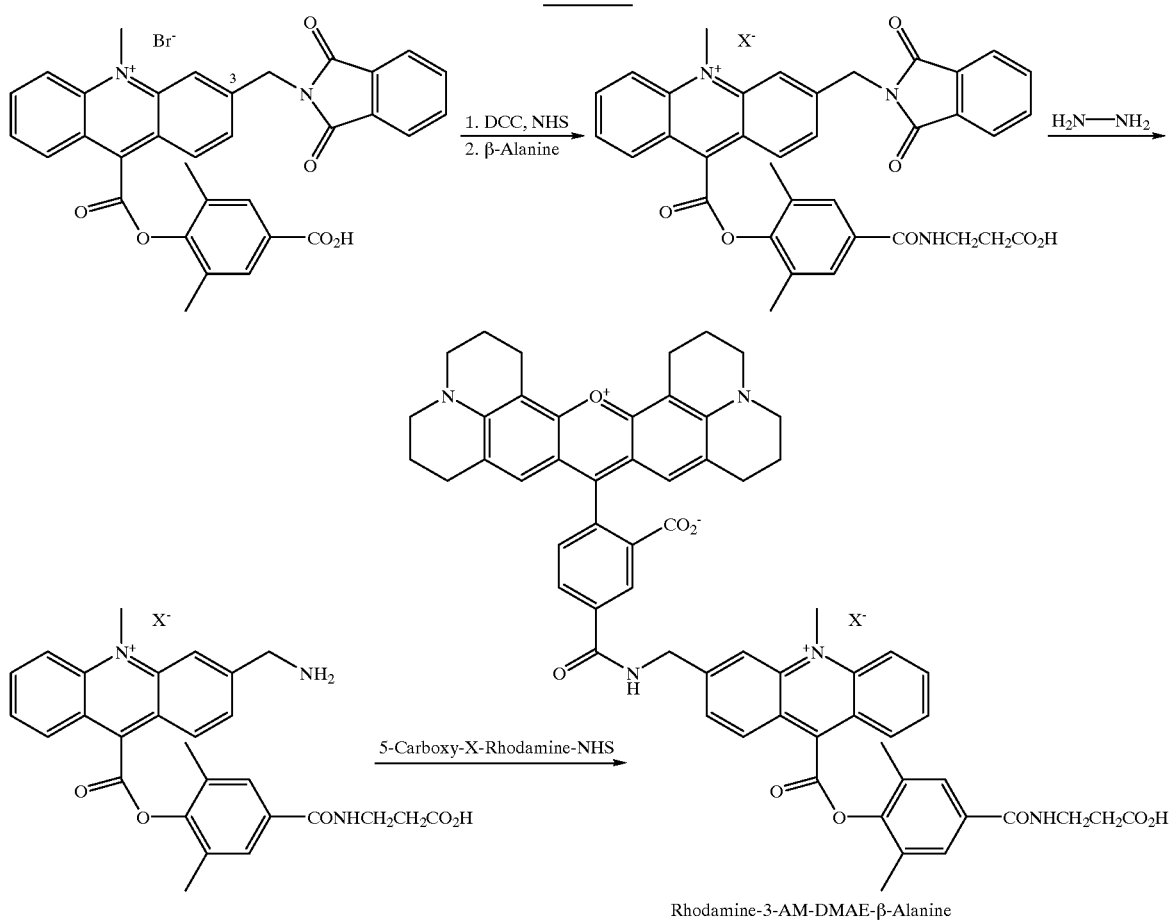

X⁻ = CF₃COO⁻ after the compound was recovered from HPLC mobile phase containing CF3COOH (4'-Carboxyethylamidocarbonyl-2',6'-dimethyl)phenyl 3-phthalimidolmethyl-10-methyl-acridinium-9-carboxylate trifluoroacetate A solution of (4'-carboxyl-2',6'-dimethyl)phenyl 3-phthalimidomethyl-10-methyl-acridinium-9-carboxylate bromide (65 mg, 0.104 mmol) in the mixed solvent of DMF (2 ml) and acetonitrile (3 ml) was treated with 1,3-dicyclohexylcarbodiimide (DCC, 70 mg, 0.335 mmol) and N-hydroxysuccinimide (NHS, 36 mg, 0.313 mmol). The reaction was stirred at room temperature for 5 hours and then evaporated to dryness. The resulting residue was reconstituted in 2 ml of anhydrous DMF and the insoluble materials were removed by filtration. To the filtrate was added a solution of β-alanine (93 mg, 1.04 mmol) in 2 ml of 0.2 M carbonate buffer, pH 9, followed by the addition of another 3 ml of DMF. The reaction was allowed to stir at room temperature for 16 hours, and then separated on a Beckman prep-60 ADD-ON HPLC system (YMC, Wilmington, N.C., 300×20 mm, ODS-A, S-10, 120 Å). The desired product (45.2 mg, yield 59%) was eluted at retention time of 27 min in step gradient by mixing 0.05% TFA/H₂O (solvent A) and 0.05% TFA/CH₃CN (solvent B) in the following manner: at 30% B for 15 min, then to 60% B in 5 min and at 60% B for 20 min; flow rate at 16 ml/min; monitored at 260 nm. MS(MALDI-TOF): m/z 618 (M+2).

(4'-Carboxyethylamidocarbonyl-2',6'-dimethyl)phenyl 3-phthalimidomethyl-10-methyl-acridinium-9-carboxylate trifluoroacetate A solution of (4'-carboxyethylamidocarbonyl-2',6'-dimethyl)phenyl 3-phthalimidomethyl-10-methyl-acridinium-9-carboxylate trifluoroacetate (45.2 mg, 0.0734 mmol) in 2 ml of anhydrous DMF was treated with 46 ul (0.147 mmol) of hydrazine for 2 hours. The reaction mixture was separated on a Beckman prep-60 ADD-ON HPLC system (YMC, Wilmington, N.C., 300×20 mm, ODS-A, S-10, 120 Å). The desired product (29 mg, yield 71%) was eluted at retention time of 27 min in step gradient by mixing 0.05% TFA/H₂O (solvent A) and 0.05% TFA/CH₃CN (solvent B) in the following manner: 5% B to 60% B in 30 min, at 60% B for another 10 min and then to 100% B in 5 min, flow rate at 16 ml/min; monitored at 260 nm. MS(MALDI-TOF): m/z 487 (M+1).

Rhodamine-3-AM-DMAE-β-Alanine

To a solution containing (4'-carboxyethylamidocarbonyl-2',6'-dimethyl)phenyl 3-aminolmethyl-10-methyl-acridinium-9-carboxylate trifluoroacetate (2.82 mg, 0.004 mmol) and triethylamine (11 ul, 0.0791 mmol) in 1 ml of anhydrous DMF was added 5-carboxy-X-Rhodamine, succinimidyl ester (5 mg, 0.0079 mmol). The reaction was allowed to stir at room temperature for 3 hours, and then separated on a Beckman prep-60 ADD-ON HPLC system (YMC, Wilmington, N.C., 300×20 mm, ODS-A, S-10, 120 Å). The desired product (1.56 mg) was eluted at retention time of 30.8 min in step gradient by mixing 0.05% TFA/H₂O (solvent A) and 0.05% TFA/CH₃CN (solvent B) in the following manner: 5% B to 60% B in 30 min, at 60% B for another 10 min and then to 100% B in 5 min; flow rate at 16 ml/min; monitored at 260 nm. MS(MALDI-TOF): m/z 1000 (M–3).

Example 7
Synthesis of Texas Red-X-3-AM-DMAE-β-Alanine separated on a Beckman prep-60 ADD-ON HPLC system (YMC, Wilmington, N.C., 300×20 mm, ODS-A, S-10, 120 Å). The desired product (0.85 mg) was eluted at retention time of 41 min in step gradient by mixing 0.05% TFA/H$_2$O (solvent A) and 0.05% TFA/CH$_3$CN (solvent B) in the following manner: 25% B for 10 min, then to 55% B in 30

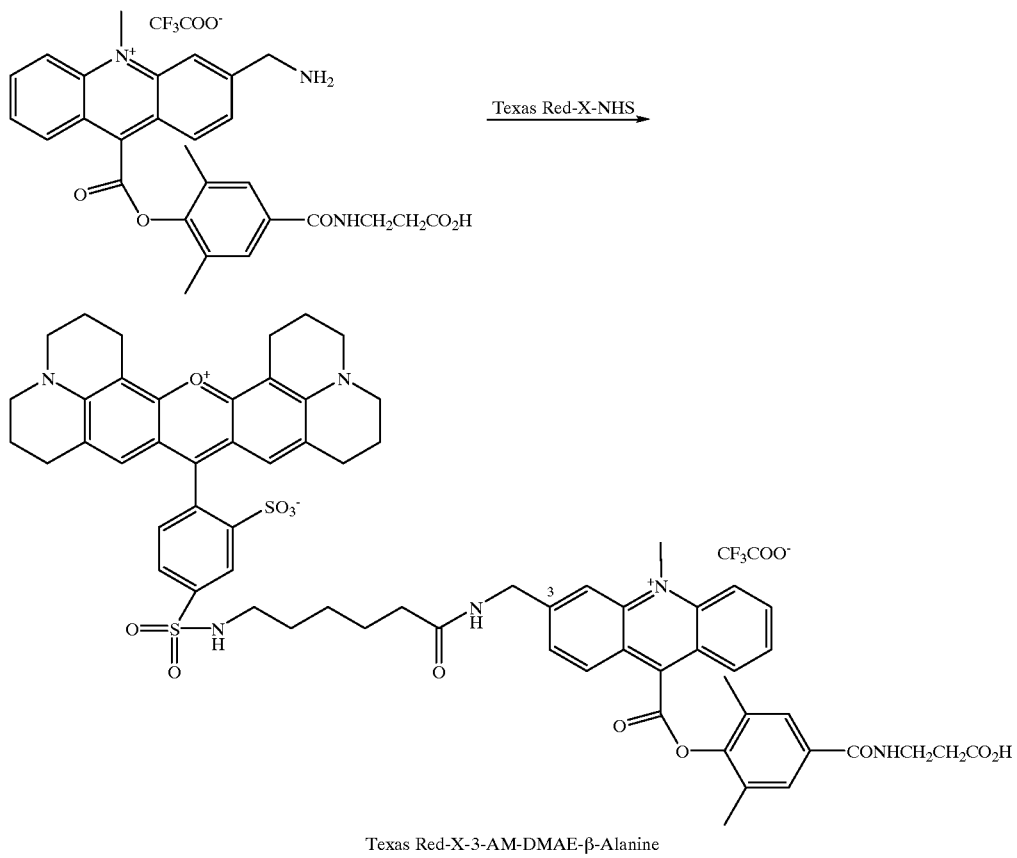

Texas Red-X-3-AM-DMAE-β-Alanine

To a solution containing (4'-carboxyethylamidocarbonyl-2',6'-dimethyl)phenyl 3-aminolmethyl-10-methyl-acridinium-9-carboxylate trifluoroacetate (2.18 mg, 0.0031 mmol) and triethylamine (8.5 ul, 0.061 mmol) in 1 ml of anhydrous DMF was treated with Texas Red-X, succinimidyl ester (5 mg, 0.0061 mmol). The reaction was allowed to stir at room temperature for 16 hours. The mixture was min, then to 100% B in 5 min; flow rate at 16 ml/min; monitored at 260 nm. MS(MALDI-TOF): m/z 1188 (M+1).

Example 8

Synthesis of Texas Red-ED-NCM-DMPAE

Scheme VIII

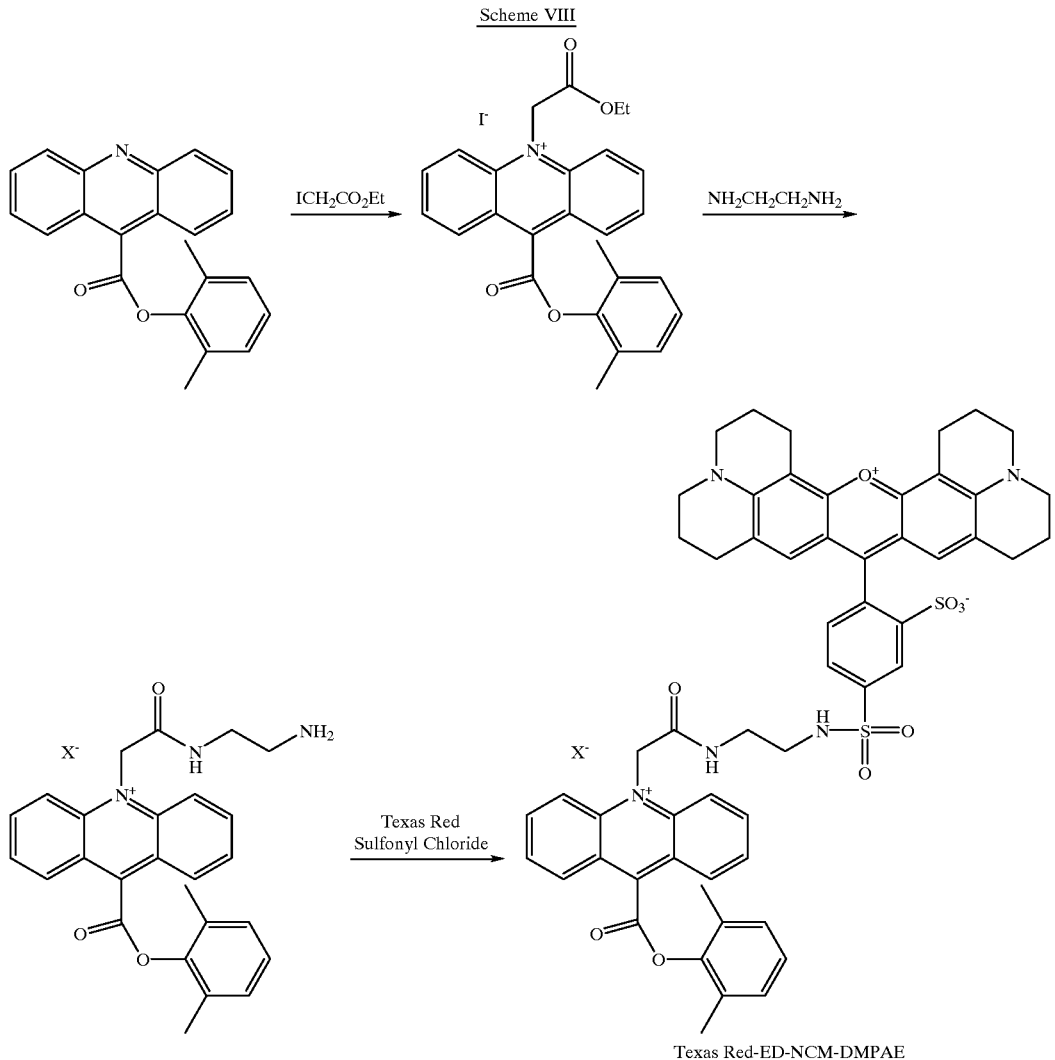

X⁻ = CF₃COO⁻ after the compound was recovered from HPLC mobile phase containing CF3COOH (2',6'-Dimethyl)phenyl 10-Ethoxycarbonylmethyl-acridinium-9-carboxylate iodide (2',6'-Dimethyl)phenyl acridine-9-carboxylate (0.5 g, 1.53 mmol) was suspended in ~8 mL ethyl iodoacetate and the reaction was heated in an oil-bath under a nitrogen atmosphere at 90° C. for 16 hours. The reaction, which had turned dark brown, was cooled to room temperature and poured into a mixture of diethyl ether (25 mL) and hexanes (50 mL). A brown solid separated out. Precipitation of the product was completed by cooling the suspension in the ether/hexane mixture in the refrigerator for 2 hours. The precipitate was then collected by filtration and redissolved in a mixture of chloroform and methanol. Concentration under reduced pressure afforded 0.23 g of a reddish-brown powder. (28% yield). TLC (silica) $R_f$=0.6 (2% methanol in chloroform). MS (MALDI-TOF): m/z 414.1 (M⁺).

(2',6'-Dimethyl)phenyl 10-Aminoethylcarbamoylmethyl-acridinium-9-carboxylate trifluoroacetate (2',6'-Dimethyl)phenyl 10-ethoxycarbonylmethyl-acridinium-9-carboxylate iodide (77 mg) was stirred with ~2 mL ethylenediamine at room temperature under a nitrogen atmosphere for 16 hours. The reaction mixture was then concentrated under reduced pressure and the residue was dissolved in methanol (1 mL). The crude product was purified by preparative HPLC on a $C_{18}$ column (YMC 30x300 mm) at a solvent flow rate=16 mL/minute, and UV detection at 260 nm, using a gradient of 0–60% MeCN in aqueous trifluoroacetic arid (0.05%) over 40 minutes. Under these conditions, the product eluted as a broad peak centered at 26 minutes. The HPLC fraction containing the product was lyophilized to dryness to yield 7.8 mg of a yellow powder (10% yield). MS (ESI): m/z 428.7 (M⁺).

Texas Red-ED-NCM-DMPAE

Texas Red sulfonyl chloride (10 mg, 0.016 mmol) was added into a solution of 3.02 mg (0.004 mmol) of (2',6'-dimethyl)phenyl 10-aminoethylcarbamoylmethyl-acridinium-9-carboxylate trifluoroacetate and 5.58 ul (0.04 mmol) of Et₃N in 1 ml of anhydrous DMF. The reaction was stirred at room temperature under nitrogen for 16 hours, and then separated on a Beckman prep-60 ADD-ON HPLC system (YMC, Wilmington, N.C., 300x20 mm, ODS-A, S-10, 120 Å). The desired product (2.42 mg) was eluted at retention time of 42 min in step gradient by mixing 0.05% TFA/H₂O (solvent A) and 0.05% TFA/CH₃CN (solvent B) in the following manner: 5% B to 60% B in 30 min, at 60%

Example 9
Synthesis of Texas Red-ED-NSP-DMPAE

B for another 5 min and then to 100% B in 5 min; flow rate at 16 ml/min; monitored at 260 nm. MS(ESI): m/z 1017 (M+1).

by preparative HPLC on a $C_{18}$ column (YMC 30×300 mm) at a solvent flow rate=16 mL/minute, with UV detector at 260 nm, and a gradient of 0–60% MeCN in aqueous trifluoroacetic acid (0.05%) over 40 minutes. Under these conditions, the product was eluted as a broad peak centered at 34 minutes. The HPLC fraction containing the product

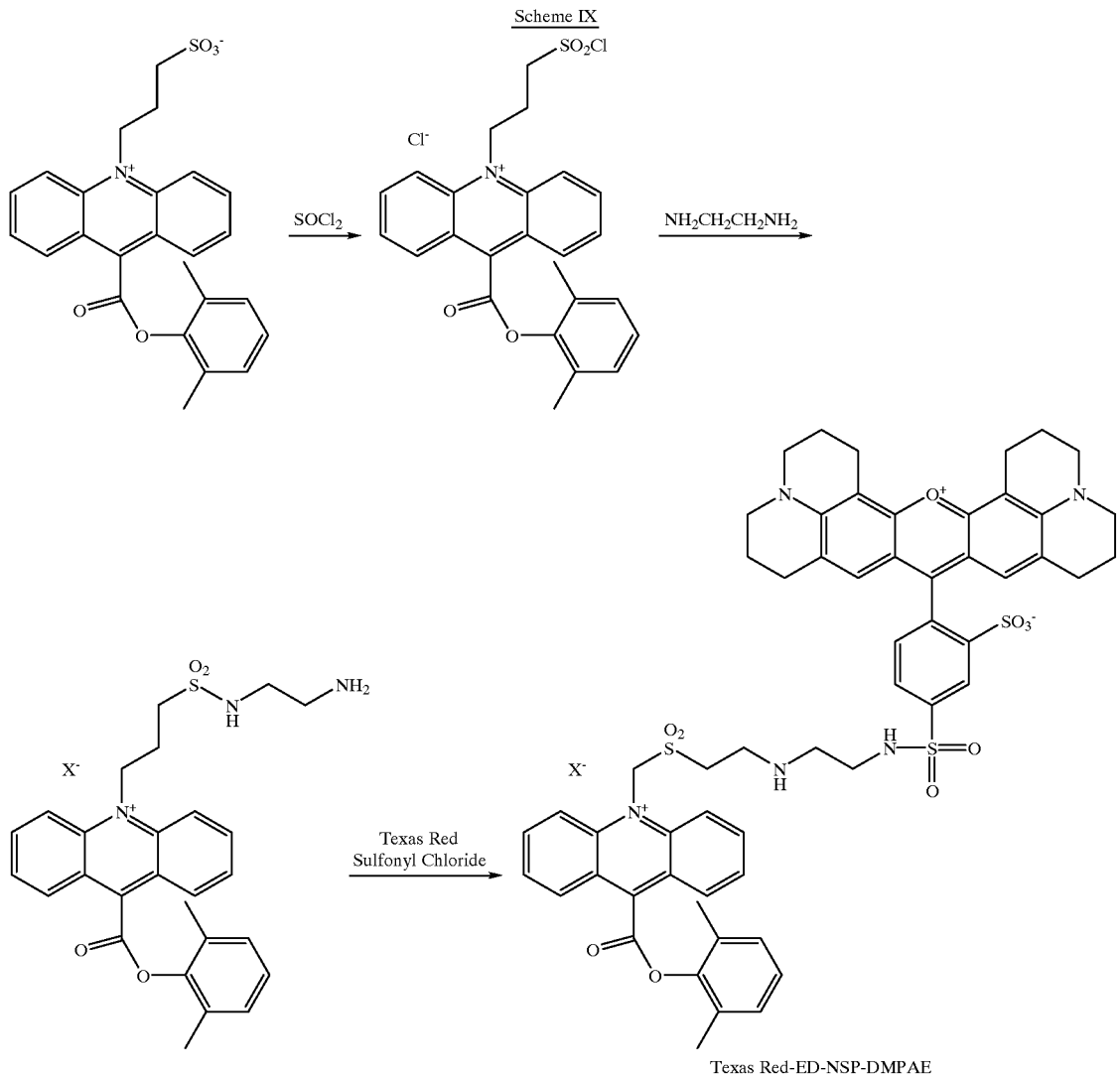

X⁻ = CF₃COO⁻ after the compound was recovered from HPLCmobile phase containing CF3COOH (2',6'-Dimethyl)phenyl N-Aminoethylaminosulfonylpropyl-acridinium-9-carboxylate trifluoroacetate N-Sulfopropyl-2',6'-dimethylphenylacridnium ester (0.1 g) was suspended in thionyl chloride (2 mL) and the suspension was refluxed under a nitrogen atmosphere for 3–4 hours. The reaction turned clear upon reflux. The reaction mixture was then cooled to room temperature and diethyl ether (~25–35 mL) was added. A yellow precipitate appeared. The ether was decanted and the precipitate was rinsed with ether three times to remove traces of thionyl chloride. Finally, the remaining solid was treated with ethylene diamine (1 mL) and pyridine (1 mL). The resulting reaction was stirred at room temperature for 2–3 hours and then concentrated under reduced pressure. The residue was dissolved in methanol (~1 mL) and the product was purified was lyophilized to dryness to afford a yellow powder. Yield 26 mg (25%). MS (ESI): m/z 492.8 (M+H⁺).

Texas Red-ED-NSP-DMPAE

A solution of (2',6'-dimethyl)phenyl 10-aminoethylaminosulfonylpropyl)-acridinium-9-carboxylate trifluoroacetate (4 mg, 0.005 mmol) and Et₃N (9.59 ul, 0.075 mmol) in 1 ml of anhydrous DMF was treated with Texas Red sulfonyl chloride (10 mg, 0.016 mmol) with stirring at room temperature under nitrogen for 16 hours. The resulting mixture was separated on a Beckman prep-60 ADD-ON HPLC system (YMC, Wilmington, N.C., 300×20 mm, ODS-A, S-10, 120 Å). The desired product (0.3 mg) was eluted at retention time of 37.8 min in step gradient by mixing 0.05% TFA/H2O (solvent A) and 0.05% TFA/CH₃CN (solvent B) in the following manner: 5% B to 60%

B in 30 min, at 60% B for another 5 min; flow rate at 16 ml min; monitored at 260 nm. MS(MALDI-TOF): m/z 1083 (M+2).

Example 10

Synthesis of Texas Red-3-ABO-DMAE-Bz

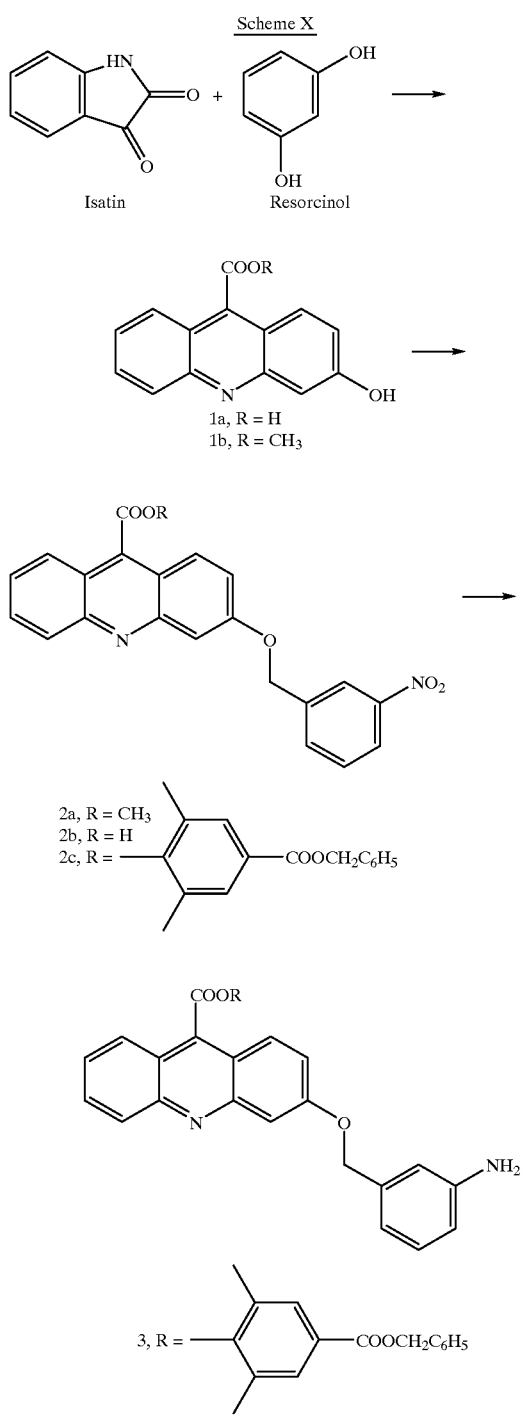

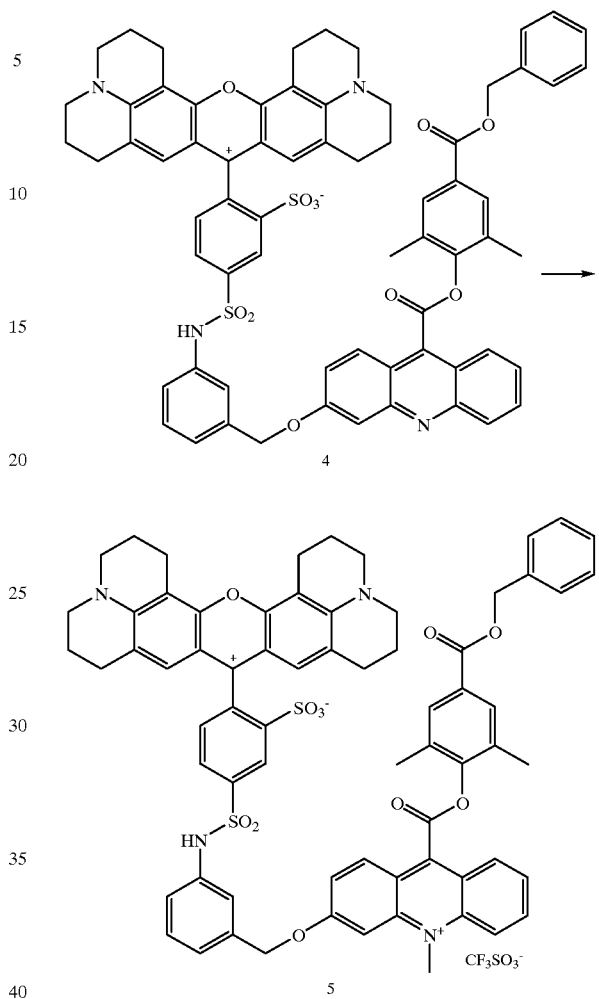

3-Hydroxyacridine-9-carboxylic acid methyl ester

3-Hydroxyacridine-9-carboxylic acid was prepared analogously to EP 0322926 A2. 3-Hydroxyacridine-9-carboxylic acid (7.8 g; 32.6 mmol) was dissolved in 200 ml sodium bicarbonate solution (10%) and stirred for 2 hours at room temperature. The precipitated sodium salt was separated on a Büchner funnel and dried, yield 7.8 g (91%). The sodium salt (7.0 g; 26.8 mmol) was esterified with methyliodide (5.6 g; 37.5 mmol) in 50 ml DMSO at room temperature. After 2 hours the solution was poured into 600 ml water and the precipitate separated, washed with water and dried in vacuo at 50° C. Yield 5.8 g (86%), Fp.>250° C. $^1$H-NMR(DMSO-$d_6$): 10.80 (1H, s, OH, exchangeable); 8.20–7.30(7H, ar.) and 4.18 ppm (3H, s, $CH_3$). MS: $M^+$=253.

3-(m-Nitrobenzyloxy)acridine-9-carboxylic acid methyl-ester

3-Hydroxyacridine-9-carboxylic acid methyl ester (14.6 g; 57.7 mmol) was dissolved in 500 ml DMF, then potassium carbonate (25.0 g; 181 mmol) and m-nitrobenzylbromide (15.0 g; 69.4 mmol) were added and stirred at room temperature. After 4 hours the mixture was filtered and the filtrate was evaporated to dryness in vacuo. The residue was dissolved in $CH_2Cl_2$ and washed with HCl 1N, NaOH 1N and sodium chloride solution (10%). After drying with sodium sulfate and evaporating to dryness the residue was flash chromatographed (column: 10 cm diameter) in $CH_2Cl_2$+1% methanol (fractions of 200 ml). Fractions 7–23 were combined, evaporated and the residue was collected on a Büchner funnel and washed with diethylether. Yield 8.7 g (39%), Fp.>250° C. $^1$H-NMR(CDCl$_3$): 5,35(2H, s, CH$_2$) and 4,22 ppm (3H, s, CH$_3$). MS: M$^+$=388.

3-(m-Nitrobenzyloxy)acridine-9-carboxylic acid 3-(m-Nitrobenzyloxy)acridine-9-carboxylic acid methylester (6.5 g; 16.7 mmol) was refluxed in 400 ml dioxane and 300 ml NaOH 1N. After 2 hours the solution was cooled and acidified to pH 1 with HCl conc., then evaporated in vacuo. The precipitate was collected on a Büchner funnel, washed with water and dried in vacuo at 50° C. Yield 5.9 g (95%), Fp.>250° C. $^1$H-NMR(DMSO-d$_6$): 8.44(1H, s, ar.); 8.23(1H, d, ar.); 8.10(2H, t, ar.); 8.03(1H, d, ar.); 7.95(1H, d, ar.); 7.72(2H. m, ar.); 7.42(2H, m, ar.); 7.27(1H, d, ar.); and 5.50 ppm (2H, s, CH$_2$). MS: M$^+$=374.

(4'-Benzyloxycarbonyl-2',6'-dimethyl)phenyl 3-(m-nitrobenzyloxy)acridine-9-carboxylate p-Toluolsulfonylchloride (38.0 g; 0.2 mol) and 3-(m-nitrobenzyloxy)acridine-9-carboxylic acid (3.75 g; 0.02 mol) in 300 ml pyridine were stirred at room temperature. After 2 hours 4-hydroxy-3,5-dimethyl-benzoic acid benzylester (3.1 g; 0.023 mol; prepared from 4-hydroxy-3,5-dimethyl-benzoic acid, potassium carbonate and benzylbromide in DMF at room temperature, Fp. 104–106° C.) was added to the clear solution. After 18 hours the solution was evaporated, the residue dissolved in ethylacetate and washed with HCl 1N, NaOH 1N and NaCl solution (10%). After drying over sodium sulfate and evaporating the residue (42 g) was flash chromatographed (column: 7 cm diameter) with $CH_2Cl_2$+5% ethylacetate. Yield 5,2 g (87%) crystallized from ethylacetate/hexane. Fp. 147–148° C. 1H-NMR (CDCl$_3$): 8.42–7.32(18H, ar.) and 5,50 ppm (4H, s, 2 CH$_2$).

(4'-Benzyloxycarboyl-2',6'-dimethyl)phenyl 3-(m-aminobenzyloxy)acridine-9-carboxylate A mixture of (4'-Benzyloxycarbonyl-2',6'-dimethyl)phenyl 3-(m-nitrobenzyloxy)acridine-9-carboxylate (3. g; 5.1 mmol), charcoal (1.3 g), iron(III)-chloride hexahydrate (0.18 g; 0.7 mmol), 40 ml N,N-dimethylhydrazine and 250 ml dry methanol was refluxed under stirring. After 4 hours the mixture was cooled and filtered, the residue was exhaustingly extracted with $CHCl_3$ and the filtrate evaporated to dryness. The residue was then collected on a Büchner funnel and washed with diethylether. Yield 2.5 g (84%), Fp. 184–186° C. $^1$H-NMR(CDCl$_3$): 5.40(2H, s, CH$_2$); 5.20(2H, s, CH$_2$) and 3,75 ppm (2H, s, NH$_2$, exchangeable). MS: M$^+$=582.

Texas Red-3-ABO-DMAeE-Bz

A mixture of Texas red (sulforhodamine 101 sulfonylchloride; 0.625 g; 1.0 mmol), (4'-Benzyloxycarboyl-2',6'-dimethyl)phenyl 3-(m-aminobenzyloxy)acridine-9-carboxylate (1.164 g; 2.0 mmol) and 30 ml $CH_2Cl_2$ was stirred under argon at room temperature. After 20 hours the solution was evaporated and the residue flash chromatographed on silicagel (column: 5.5 cm diameter) with $CHCl_3$+3% methanol (fractions of 50 ml). Fractions 21–38 were collected, evaporated and once more chromatographed on $Al_2O_3$ (Brockman, Neutral, Akt. 1). The first red zone (disulfonamide) was eluted with $CHCl_3$+3% methanol and a second red zone of Texas Red-3-ABO-DMAeE-Bz was eluted with $CHCl_3$+6% methanol. Yield 0.40 g (34%). $^1$H-NMR(CDCl$_3$): 8.89(1H, d, ar.); 8.41(1H, s, NH, exchangeable); 8.32–7.13(20H, ar.); 6.70(2H, s, ar.); 5.40 (2H, s, CH$_2$); 5.19(2H, s, CH$_2$); 3.28, 2.78 2.48, 1,90(24H, m, 12 CH$_2$) and 2.40 ppm (6H, s, 2 CH$_3$). MS: MH$^+$=1170.8. UV/VIS(CHCl$_3$): $\lambda_{max}$=578 nm.

Texas Red-3-ABO-DMAE-Bz

Texas Red-3-ABO-DMAeE-Bz (46.8 mg; 4×10$^{-5}$ mol) and methyl trifluoromethansulfonate (78.7 mg; 48×10$^{-5}$ mol) in 10 ml $CH_2Cl_2$ were allowed to stand at room temperature. After 18 hours the solution was evaporated in vacuo at room temperature and the residue collected with diethylether on a Büchner funnel and dried 24 hours at room temperature in high vacuo. Yield 45 mg (95%). $^1$H-NMR (CDCl$_3$): 9.82(1H, s, exchangeable); 8.53–7.33 & 6.40(23H, ar.); 5.40 (4H, s, 2 CH$_2$); 3.45(3H, s, CH$_3$NH$^+$) and 2.46 ppm (6H, s, 2 CH$_3$). MS: M$^+$=1148.8. UV/VIS(CHCl$_3$): $\lambda_{max}$=590 nm.

Example 11

Synthesis of Texas Red-3-APO-DMAE-Bz

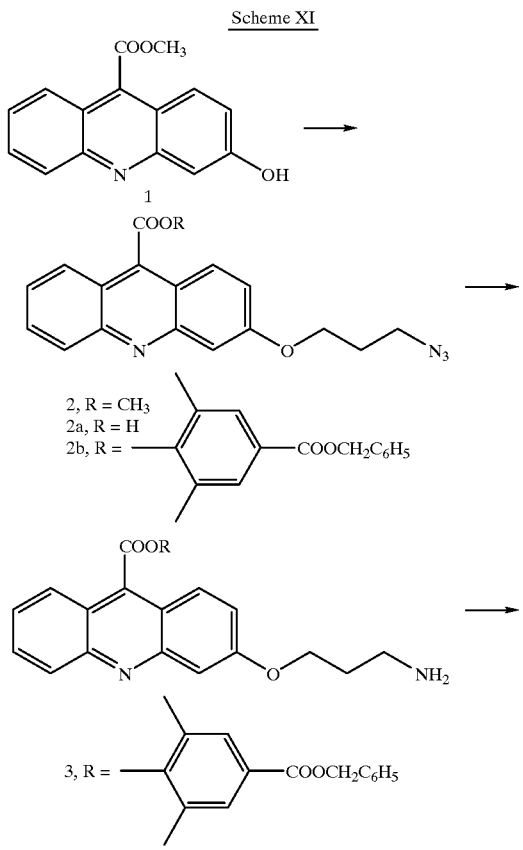

Scheme XI

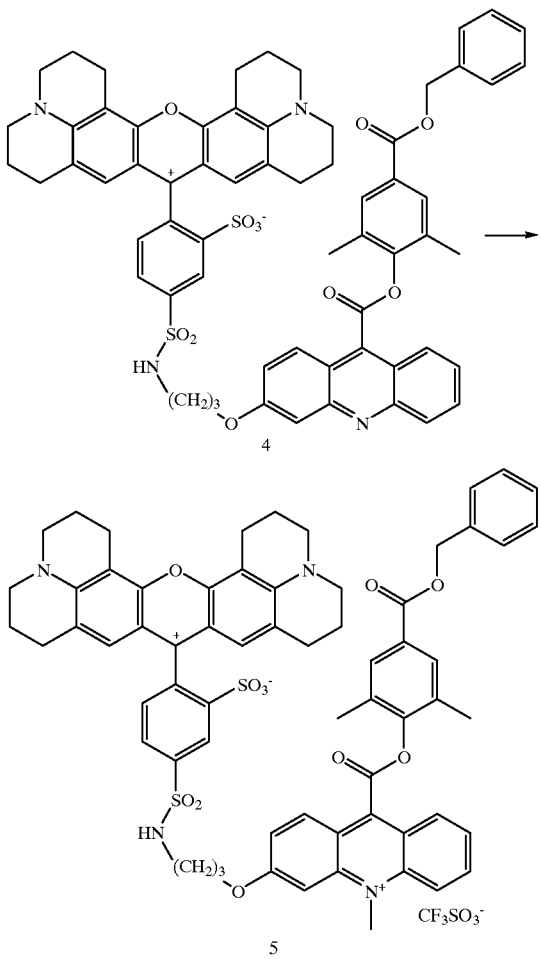

ω-Azidopropyl-p-tolylsulfonate

To a mixture of sodium azide (26.0 g; 0.4 mol) and 200 ml DMF 3-bromopropanol (35.0 g; 0.4 mol) was added dropwise under stirring at room temperature and then heated to 110° C. After 23 hours the mixture was cooled and 1000 ml diethylether and 500 ml water were added and separated. The aqueous phase was extracted twice with 500 ml diethylether and the organic phase was washed four times with 600 ml water. Drying over sodium sulfate and evaporating yielded 16.3 g (40%) crude ω-azido-propanol as yellowish liquid.

To a mixture of crude ω-azidopropanol (10.1 g; 0.1 mol) and 50 ml pyridine, p-toluol-sulfonylchloride (19.1 g; 0.1 mol) was added under stirring at 0° C. in 6 portions. After 3 hours the mixture was poured onto water, extracted with diethylether and washed with HCl 1N. Drying over sodium sulfate and evaporating yielded 22.5 g (88%) ω-azidopropyl-p-tolylsulfonate as yellowish liquid. $^1$H-NMR: 7.80, 7.63(4H, $A_2B_2$, ar.); 4.12(2H, t, $CH_2$); 3.40(2H, t, $CH_2$); 2.46(3H, s, $CH_3$) and 1.90 ppm (2H, quint, $CH_2$).

3-(ω-Azidopropyloxy)acridine-9-carboxylic acid methylester

Methyl 3-hydroxy-acridine-9-carboxylate (0.2 g; 0.04 mol) was dissolved in 1000 ml DMF, then potassium carbonate 22.2 g; 0.16 mol) and ω-azidopropyl-p-tolylsulfonat (15.2 g; 0.15 mol) were added and stirred at room temperature. After 5 hours a further amount of the azide (5.2 g; 0.05 mol) was added and stirring at room temperature was continued for 19 hours. The potassium carbonate was filtered and the filtrate evaporated in vacuo to dryness. The residue was flash chromatographed with $CH_2Cl_2$+5% ethylacetate. Yield 8.0 g crystallized from diisopropylether. Fp.=96–97° C. $^1$H-NMR(CDCl$_3$): 8.18(1H, d, ar.); 7.97(1H, d, ar.); 7.90(1H, d, ar.); 7.78(1H, m, ar.); 7.55(1H, m, ar.); 7.49(1H, s, ar.); 7.28(1H, d, ar.); 4.30(2H, t, $CH_2$); 4.20(3H, s, $CH_3$); 3.60(2H, t, $CH_2$) and 2.18 ppm (2H, quint, $CH_2$). MS: M$^+$=366.

3-(ω-Azidopropyloxy)-acridine-9-carboxylic acid 3-(ω-Azidopropyloxy)acridine-9-carboxylic acid methylester (0.673 g; 2.0 mmol) was refluxed in 40 ml dioxane and 30 ml NaOH 1N. After 1 hour the solution was cooled, acidified to pH 1 with HCl conc. and then evaporated in vacuo. The precipitate was collected on a Büchner funnel, washed with water and dried in vacuo at 50° C. Yield 0.58 g (86%), Fp. 252° C. (decomp.). $^1$H-NMR(DMSO-d$_6$): 8.20–7.35(7H, ar.); 4.32(2H, t, $CH_2$); 3.60(2H, t, $CH_2$) and 2.10(2H, quint, $CH_2$). MS: M+H$^+$=323.

(4'-Benzyloxycarbonyl-2',6'-dimethyl)phenyl 3-(ω-azidopropyloxy)-acridine-9-carboxylate p-Toluolsulfonylchloride (57 g; 0.3 mol) and 3-(ω-azidopropyloxy)-acridine-9-carboxylic acid (9.5 g; 0.03 mol) in 750 ml pyridine were stirred at room temperature. After 3 hours 4-hydroxy-3,5-dimethyl-benzoic acid benzylester (9.2 g; 0.036 mol) was added. After 20 hours the solution was evaporated, the residue dissolved in ethylacetate and washed with HCl 1N, NaOH 1N and NaCl solution (10%). After drying over sodium sulfate and evaporating the residue was flash chromatographed (column 10 cm diameter) with $CH_2Cl_2$+5% ethylacetate. Yield 13.2 g (78%), crystallized from diisopropylether. Fp. 91–93° C. $^1$H-NMR(CDCl$_3$): 8.40–7.33(14H, ar.); 5.40(2H, s, $CH_2$); 4.32(2H, t, $CH_2$); 3.10(2H, t, $CH_2$); 2.48(6H, s, 2 $CH_3$) and 2.20 ppm (2H, quint, $CH_2$). MS: M$^+$=560.

(4'-Benzyloxycarbonyl-2',6'-dimethyl)phenyl 3-(ω-aminopropyloxy)acridine-9-carboxylate (4'-Benzyloxycarbonyl-2',6'-dimethyl)phenyl 3-(ω-azidopropyloxy)-acridine-9-carboxylate (2.8 g; 5 mmol) and triphenylphosphine (2.6 g; 10 mmol) were stirred in 100 ml THF at room temperature for 6 hours, then water (2.5 ml) was added and stirring was continued for 17 hours. Then the solution was evaporated and 200 ml diethylether and 80 ml HCl 1N were added. The precipitate was filtered and distributed in 100 ml CHCl$_3$ and 50 ml NaOH 1N; the organic phase was then washed with NaCl solution (10%), dried over sodium sulfate and evaporated to dryness. Yield 3.3 g viscous oil (96%). $^1$H-NMR(CDCl$_3$): 8.40–7.30(14H, ar.); 5.40(2H, s, $CH_2$); 4.30(2H, t, $CH_2$); 2.95(2H, t, $CH_2$); 2.45(6H, s, 2 $CH_3$) and 2.08 ppm (2H, quint, $CH_2$) MS: M$^+$=534.

Texas Red-3-APO-DMAeE-Bz

A mixture of Texas red (sulforhodamine 101 sulfonylchloride; 1.068 g; 1 mmol), (4'-Benzyloxycarbonyl-2',6'-dimethyl)phenyl 3-(ω-aminopropyloxy)acridine-9-carboxylate (0.626 g; 2 mmol) and 70 ml $CH_2Cl_2$ was stirred under argon at room temperature. After 20 hours the solution was evaporated and chromatographed on $Al_2O_3$ (Brockman, A, Akt. 1) with $CHCl_3$+3% methanol (fractions of 30 ml). The first 5 fractions contained the disulfonamide. The second red zone contained the desired product, fractions 16–38 were collected and evaporated to dryness. Yield 0.265 g (24%). 1H-NMR(CDCl$_3$): 8.88, 8.38–7.23 and 6.80(19H, ar.); 5.85(1H, t, NH, exchangeable); 5.40(2H, s, $CH_2$); 2.44(6H, s, 2 $CH_3$); 4.25, 4.40, 2.95, 2.75, 2.69, 2.20, 2.02 and 1.88 ppm (30H, 15, m, $CH_2$). MS: MH$^+$=1122.8. UV/VIS(CHCl$_3$): $\lambda_{max.}$=577 nm.

Texas Red-3-APO-DMAE-Bz

Texas Red-3-APO-DMAeE-Bz (45 mg; $4\times10^{-5}$ mol) and methyl trifluoromethansulfonate (78.7 mg; $48\times10^{-5}$ mol) in 10 ml $CH_2Cl_2$ were allowed to stand at room temperature. After 20 hours the solution was evaporated in vacuo at room temperature and the residue collected with diethylether on a Büchner funnel and dried 24 hours at room temperature in high vacuo. $^1$H-NMR($CDCl_3$): 8.68, 8.50–7.35 and 6.67 (19H, ar.); 8.56(1H, d, exchangeable); 5.40(2H, s, $CH_2$); 3.78(3H, s, $CH_3$); 2.45(6H, s, 2 $CH_3$); 4.56, 3.51, 3.02, 2.75, 2.32, 2.10 and 1.75 ppm (30H, m, 15 $CH_2$). MS: $M^+$=1136.7. UV/VIS ($CHCl_3$): $\lambda_{max.}$=592 nm.

Example 12

Synthesis of Rhodamine-2-AM-DMAE-HD-Theophylline

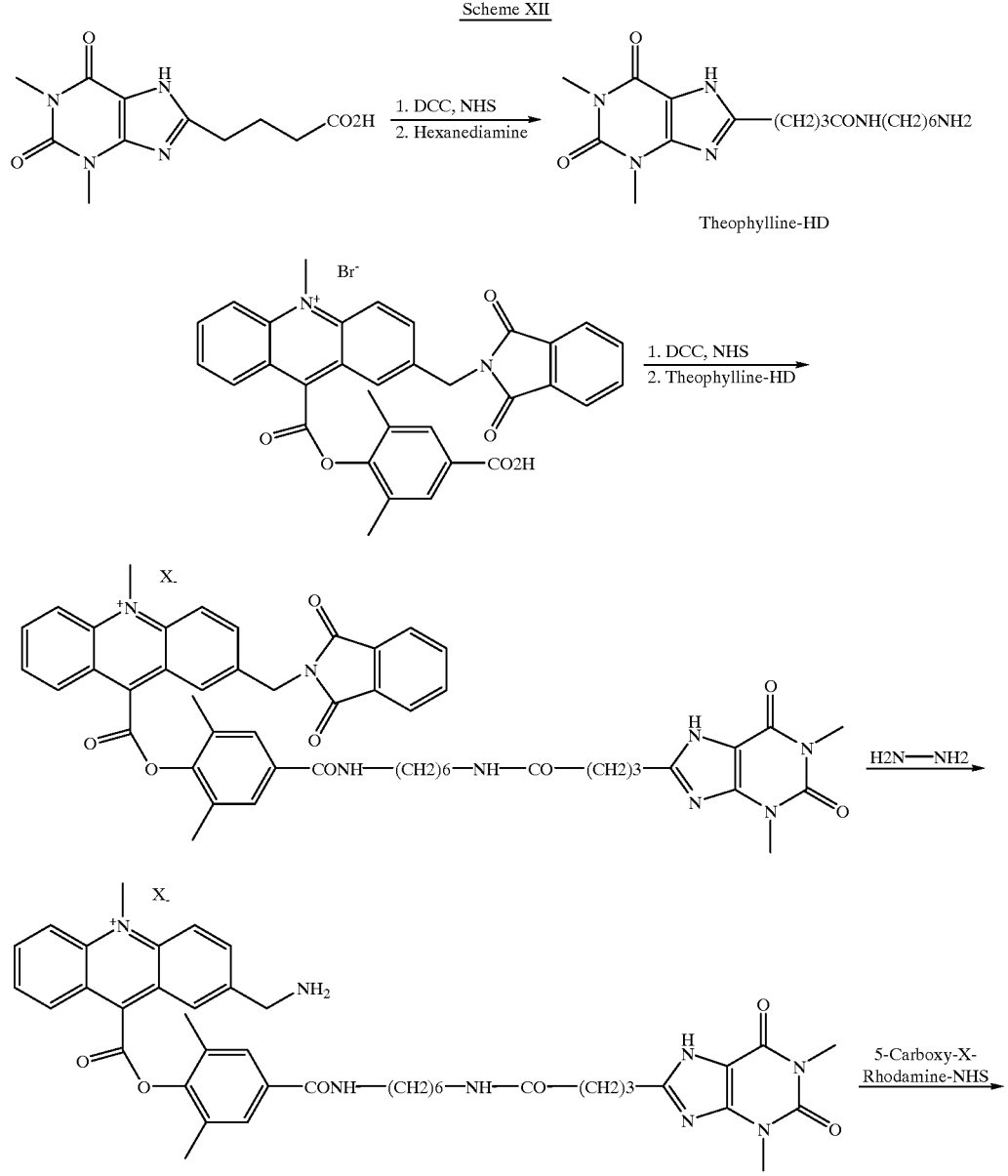

-continued

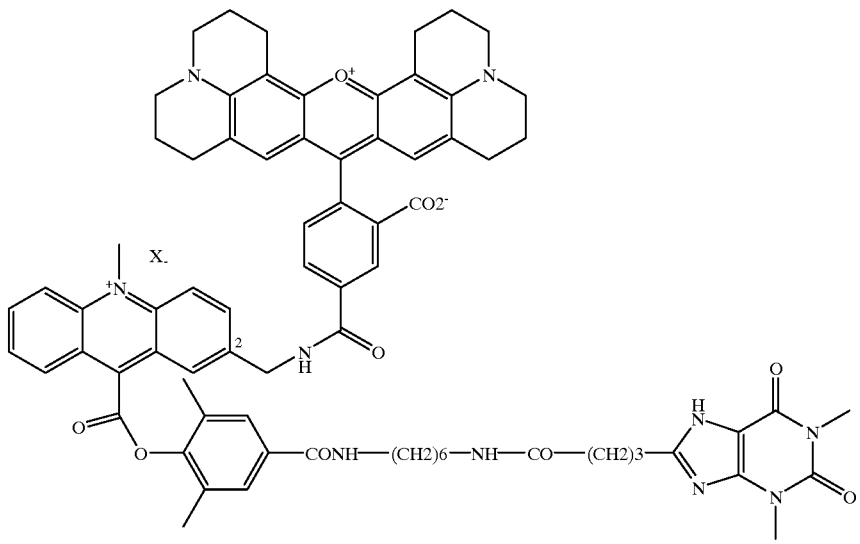

Rhodamine-2-AM-DMAE-HD-Theophylline

X_ = CF3COO—— after the compound was recovered from HPLC mobil phase containing CF3COOH Aminohexylamido-theophylline (Theophylline-HD)

To a solution containing 30 mg (0.113 mmol) of 8-carboxypropyl-theophylline in 1.5 ml of anhydrous DMF was added 69.7 mg (0.339 mmol) of DCC and 77.8 mg (0.678 mmol) of NHS. The reaction was allowed to stir at room temperature for 16 hours to form the NHS ester of 8-carboxypropyl-theophylline. This was then treated with a solution of 131 mg (1.13 mmol) of 1,6-hexyldiamine in 1 ml of 0.2 M carbonate buffer, pH 9.0 and 0.5 ml of DMF. The reaction was stirred at room temperature for three hours and then separated on a Beckman prep-60 ADD-ON HPLC system (YMC, Wilmington, N.C., 300×20 mm, ODS-A, S-10, 120 Å). The desired product (55 mg) was eluted at retention time of 26 min in step gradient by mixing 0.05% TFA/H$_2$O (solvent A) and 0.05% TFA/CH$_3$CN (solvent B) in the flowing manner: at 10% B for 15 min and then to 30% B in 10 min, at 30% B for 10 min and then to 100% B in 5 min; flow rate at 16 ml/min; monitored at 260 nm. MS(MALDI-TOF): m/z 365 (M+1).

[4-(Theophylline-8-butanoylamido)hexylamidocarbonyl-2,6-dimethyl]phenyl 2-phthalimidomethyl-10-methyl-acridinium-9-carboxylate trifluoroacetate A solution of (4-carboxyl-2,6-dimethyl)phenyl 2-phthalimidomethyl-10-methyl-acridinium-9-carboxylate bromide (10 mg, 0.0152 mmol) in the mixed solvent of anhydrous acetonitrile (1 ml) and DMF (0.5 ml) was treated with DCC (12.5 mg, 0.061 mmol) and NHS (10.5 mg, 0.092 mmol). After 4 hours, the reaction was evaporated under reduced pressure to dryness. The residue was redissolved in 1 ml of anhydrous DMF and then filtered to remove the insoluble materials. The filtrate was treated with triethylamine (19 ul, 0.137 mmol), followed by the addition of aminohexylamido-theophylline (20 mg, 0.0547 mmol). The reaction was allowed to stir at room temperature under nitrogen for 2 hours. The mixture was then separated on a Beckman prep-60 ADD-ON HPLC system (YMC, Wilmington, N.C., 300×20 mm, ODS-A, S-10, 120 Å). The desired product (18 mg) was eluted at retention time of 25.6 min in step gradient by mixing 0.05% TFA/H$_2$O (solvent A) and 0.05% TFA/CH$_3$CN (solvent B) in the following manner: at 30% B for 15 min, then to 60% B in 5 min and at 60% B for 20 min; flow rate at 16 ml/min; monitored at 260 nm. MS (MALDI-TOF): m/z 891 (M+1).

[4-(Theophylline-8-butanoylamido)hexylamidocarbonyl-2,6-dimethyl]phenyl 2-aminomethyl-10-methyl-acridinium-9-carboxylate trifluoroacetate A solution of [4-(theophylline-8-butanoylamido)hexylamidocarbonyl-2,6-dimethyl]phenyl 2-phthalimidomethyl-10-methyl-acridinium-9-carboxylate trifluoroacetate (15 mg, 0.0149 mmol) in 1.6 ml of methanol was treated with hydrazine (42.2 ml, 1.345 mmol) for one hour. The reaction mixture was separated on a Beckman prep-60 ADD-ON HPLC system (YMC, Wilmington, N.C., 300×20 mm, ODS-A, S-10, 120 Å). The desired product (12.8 mg) was eluted at retention time of 25.6 min in step gradient by mixing 0.05% TFA/H$_2$O (solvent A) and 0.05% TFA/CH$_3$CN (solvent B) in the following manner: 20% B to 60% B in 30 min, at 60% B for another 5 min; flow rate at 16 ml/min; monitored at 260 nm. MS (MALDI-TOF): m/z 762 (M+1).

Rhodamine-2-AM-DMAE-HD-theophylline

A solution of [4-(Theophylline-8-butanoylamido)hexylamidocarbonyl-2,6-dimethyl]phenyl 2-aminomethyl-10-methyl-acridinium-9-carboxylate trifluoroacetate (2 mg, 0.00233 mmol) in 1 ml of anhydrous DMF containing 16.5 ul (0.0297 mmol) of triethylamine was treated with succinimidyl ester (5 mg, 0.00791 mmol) with stirring at room temperature for 3 hours. The reaction mixture was separated on a Beckman prep-60 ADD-ON HPLC system (YMC, Wilmington, N.C., 300×20 mm, ODS-A, S-10, 120 Å). The desired product (3.75 mg) was eluted at retention time of 24.5 min in step gradient by mixing 0.05% TFA/H$_2$O (solvent A) and 0.05% TFA/CH$_3$CN (solvent B) in the following manner: 20% B to 60% B in 30 min, at 60% B for another 5 min; flow rate at 16 ml/min; monitored at 260 nm. MS (MALDI-TOF): m/z 1279 (M+1).

Example 13

Application of an ETC Tracer in a Competitive Binding Assay

Figure 5:
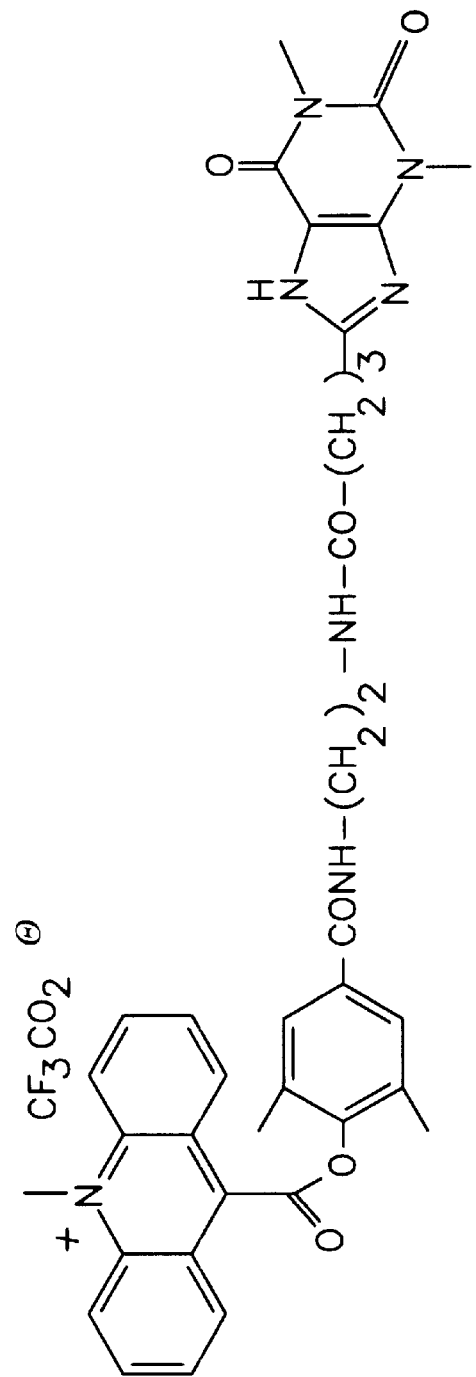
FIG. 5 is the structure of DMAE-ED-Theophylline tracer.
Figure 6:
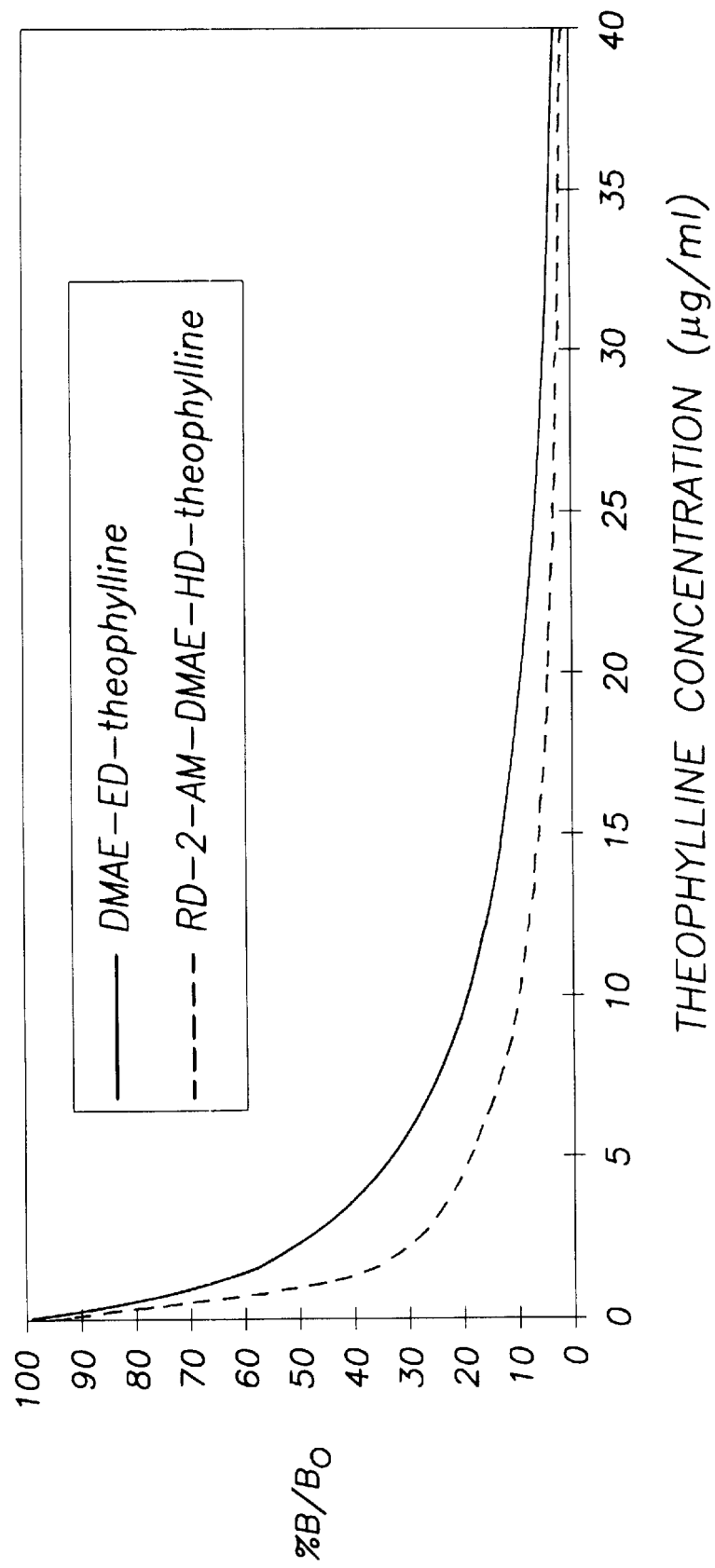
FIG. 6 is a comparison of the standard curves of Ciba Corning Diagnostics Corp. ACS theophylline assay, resulting from the use of DMAE-ED-Theophyline and Rhodamine-2-AM-DMAE-HD-Theophylline tracers, respectively.

Assay performance functionality of Rhodamine-2-AM-DMAE-HD-theophylline (Scheme XII) as an ETC tracer was evaluated through direct comparison with the reference DMAE-ED-theophylline tracer (FIG. 5). The automated Ciba-Corning ACS™ Theophylline Assay, run on a Ciba-Corning Automated Chemiluminescence System: 180® (ACS: 180), was utilized for this purpose. In this assay the acridinium ester labeled theophyllines and the theophylline Rhodamine-2-AM-DMAE-HD-theophylline and DMAE-ED-theophylline tracers (FIG. 6).

Competitive displacement of Rhodamine-2-AM-DMAE-HD-theophylline tracer from the solid phase by theophylline indicated the functional competence of Rhodamine-2-AM-DMAE-HD-theophylline as a tracer for the quantitation of theophylline concentration (Table 4).

TABLE 4

Change in % $B/B_o$ Relative to Theophylline Concentration

| Tracer | Theophylline Concentration ($\mu$g/mL) | | | | | | |
|---|---|---|---|---|---|---|---|
|  | 0.00 | 1.25 | 2.50 | 5.00 | 10.0 | 20.0 | 40.0 |
| DMAE-ED-theophylline | 100 | 65 | 50 | 33 | 19 | 9.0 | 2.9 |
| Rhodamine-2-AM-DMAE-HD-theophylline | 100 | 44 | 29 | 19 | 10 | 4.1 | 1.6 | standards (Ciba Corning Diagnostics Corp.) compete for a limited amount of murine monoclonal anti-theophylline antibody which was covalently coupled to a paramagnetic particle solid phase. A reaction mixture containing 20 $\mu$l of theophylline standard, 450 $\mu$l of solid phase and 100 $\mu$l of probe was incubated at 37° C. for 7.5 min. Theophylline standards contained theophylline in concentrations of 0.00, 1.25, 2.50, 5.00, 10.0, 20.0 and 40.0 $\mu$g/ml. The solid phase was collected on an array of permanent magnets and washed twice with deionized water to remove unbound tracer. The chemiluminescent reaction was initiated, as described previously. Data were collected as photons detected by the ACS: 180 and expressed as RLU.

A non-linear, inverse relationship exists between the theophylline concentration present in the standard and the RLUs detected by the ACS: 180. Mean RLU values resulting from a specific theophylline concentration and represented here as $\mu$, were calculated from three replicates. Non-tracer assay reagents also contribute a small and sometimes significant number of RLUs. Therefore, a control reaction, containing all assay reagents except tracer, was run in parallel to determine non-tracer reagent background, represented here as b. Mean RLUs, $\mu$, were corrected to represent RLUs obtained from the tracer only, represented here as B, where B=$\mu$−b. Where the theophylline concentration was 0.00 $\mu$g/ml, the corrected mean RLU value was represented as $B_0$. Several standard competitive assay criteria were examined to evaluate Rhodamine-2-AM-DMAE-HD-theophylline tracer functionality. The principal parameter for this comparative evaluation was % $B/B_0$. In addition to % $B/B_0$, the secondary indicators of comparative performance were minimal detectable analyte concentration (sensitivity) and % c.v.

As with theophylline concentration and RLUs, a non-linear, inverse relationship exists between the theophylline concentration present in the standard and % $B/B_0$. Calculation for % $B/B_0$, was simply % $B/B_0$=100×$B/B_0$. The standard curve, graphed with theophylline concentration on the x-axis verses % $B/B_0$ on the y-axis, was common to both Exponential regression was used to approximate standard curve shape in the equation form of y=bm$^x$ or x=(lny−lnb)/lnm. Theoretical sensitivity was calculated as the theophylline concentration for a value B, obtained by the subtraction of two standard deviations from the corrected $B_0$ mean. The minimal detectable theophylline concentration using Rhodamine-2-AM-DMAE-HD-theophylline as a tracer was comparable to that obtained from the DMAE-ED-theophylline tracer (Table 4).

The % c.v. values for the three replicates at a specific theophylline concentration were calculated as % c.v.=(100× standard deviation/$\mu$). While the % c.v. values were slightly higher overall for the Rhodamine-2-AM-DMAE-HD-theophylline tracer, they were not detrimentally so since target % c.v. values should be less than or equal to five percent (Table 5).

TABLE 5

% C.V. for Three Replicates

| Tracer | Theophylline Concentration ($\mu$g/mL) | | | | | | |
|---|---|---|---|---|---|---|---|
|  | 0.00 | 1.25 | 2.50 | 5.00 | 10.0 | 20.0 | 40.0 |
| DMAE-ED-theophylline | 2.0 | 2.7 | 2.1 | 1.6 | 0.6 | 1.6 | 1.3 |
| Rhodamine-2-AM-DMAE-HD-theophylline | 2.5 | 0.7 | 2.4 | 2.6 | 2.0 | 2.8 | 4.3 |

Application of an ETC Tracer in a Simultaneous Dual Analyte Binding Assay

Figure 7:
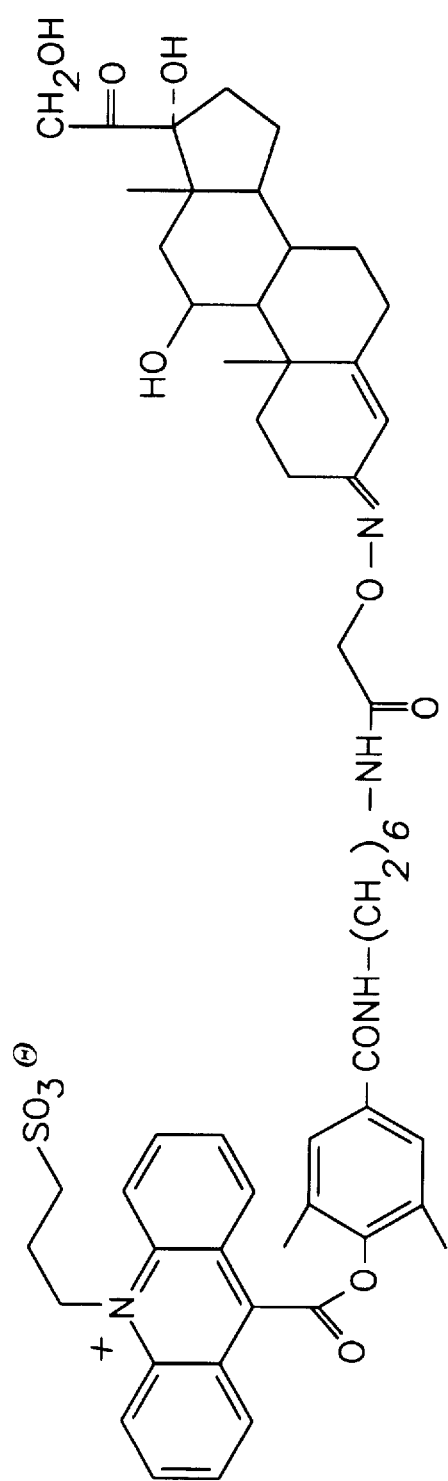
FIG. 7 is the structure of NSP-DMAE-HD-3-CMO-Cortisol tracer.
Figure 8:
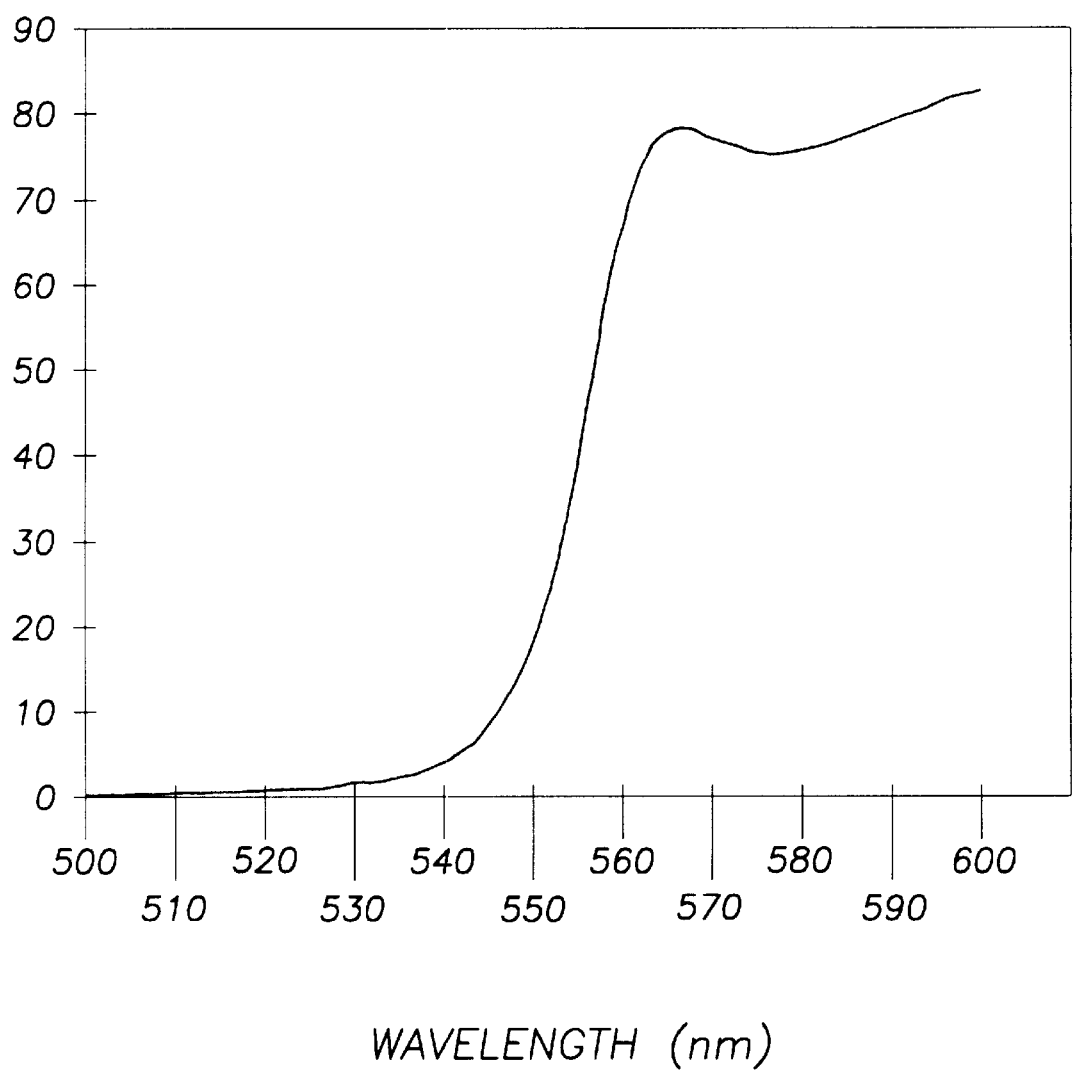
FIG. 8 is the transmission spectrum of Corion LL-550 filter.
Figure 9:
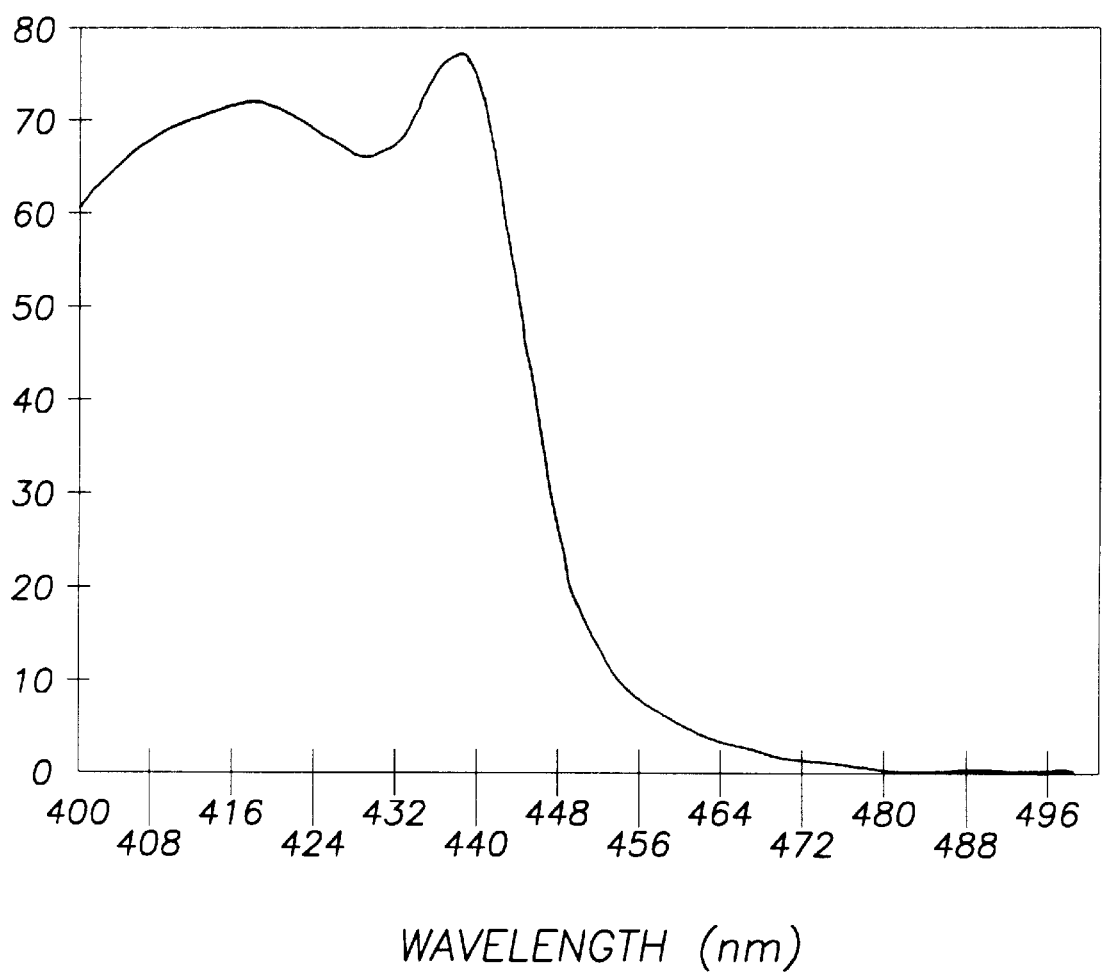
FIG. 9 is the transmission spectrum of Corion LS-450 filter.
Figure 10:
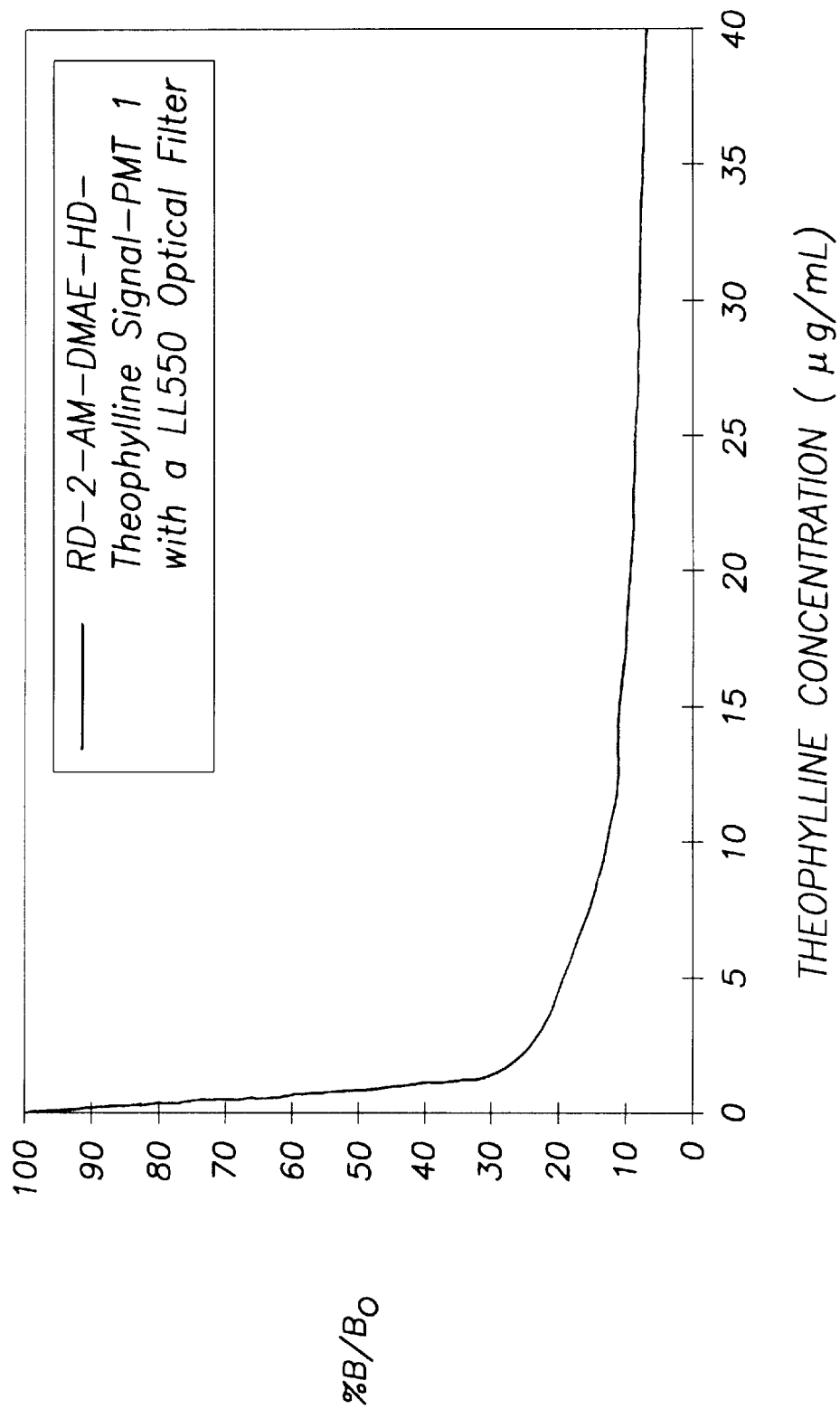

Dual Theophylline/Cortisol Binding Assay—Functionality of Rhodamine-2-AM-DMAE-HD-theophylline as a tracer in a dual analyte assay for the quantitation of theophylline was evaluated with the parallel determination of cortisol concentration using a NSP-DMAE-HD-3-CMO-cortisol tracer (FIG. 7). A manual assay employing components identical or similar in nature to those described previously was utilized for this purpose. As with the interaction between Rhodamine-2-AM-DMAE-HD-theophylline tracer, theophylline standard and theophylline binding solid-phase, the NSP-DMAE-HD-3-CMO-cortisol tracer and cortisol from cortisol-containing standards (Ciba Corning Diagnostics Corp.) compete for a limited amount of polyclonal rabbit anti-cortisol antibody, covalently coupled to a paramagnetic particle solid phase. A reaction mixture containing 20 $\mu$l of theophylline standard, 20 $\mu$l of cortisol standard, 450 µl of theophylline solid phase, 250 µl of cortisol solid phase, 100 µl of Rhodamine-2-AM-DMAE-HD-theophylline tracer and 50 µl of NSP-DMAE-HD-3-CMO-cortisol tracer was incubated at ambient temperature for 2 h. Cortisol standards contained cortisol in concentrations of 0.00, 10.0, 20.0, 60.0, 120, 300 and 800 ng/ml, while theophylline standards were the same as those described above. The solid phase was collected on an array of permanent magnets and washed twice with deionized water to remove unbound tracer. The chemiluminescent reaction was initiated, as described previously. Data were collected as photons in two channels detected by a Ciba-Corning Dual-PMT Fixture® (dual luminometer), equipped with a Corion LL-550 optical filter (FIG. 8) on PMT 1 and a Corion LS450 optical filter (FIG. 9) on PMT 2. Data were expressed as RLUs.

Figure 11:
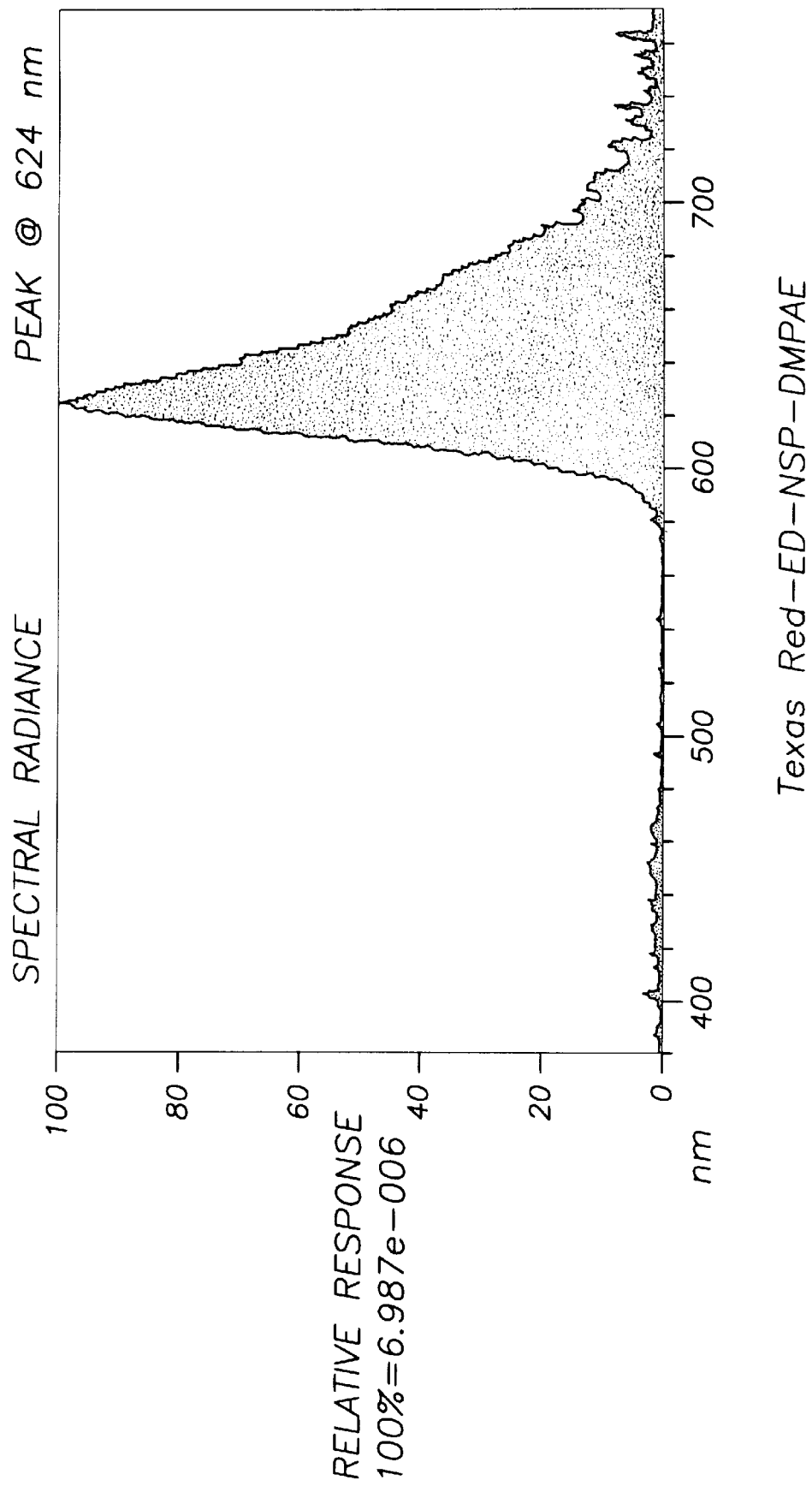
FIG. 11 is a cortisol standard curve determined from an assay mixture of theophylline and cortisol standards.
Figure 10:
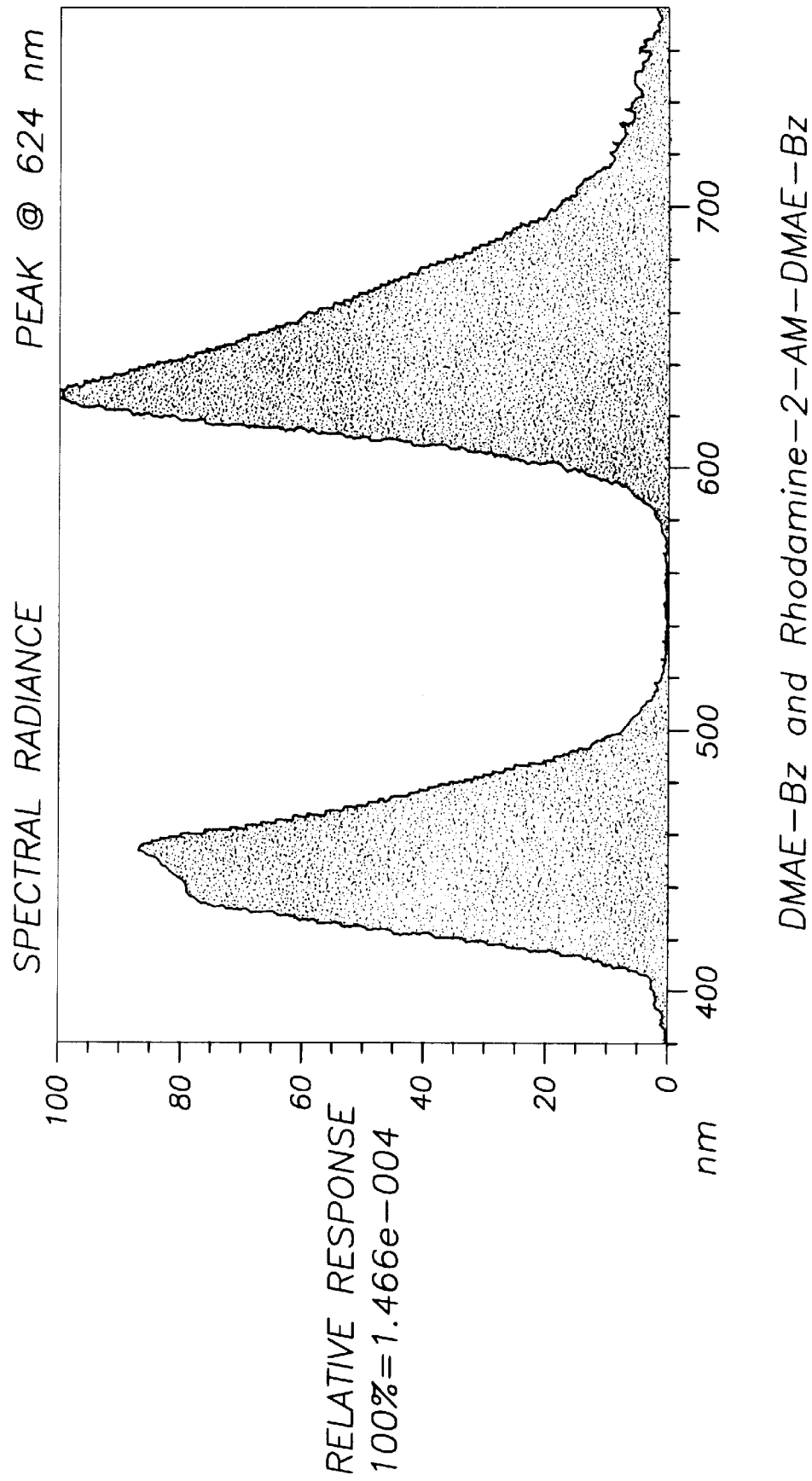
FIG. 10 is a theophylline standard curve determined from an assay mixture of theophylline and cortisol standards.

As with the theophylline assay a non-linear, inverse relationship exists between the cortisol concentration present in the cortisol standard and the RLUs detected by the dual luminometer. Standard competitive assay parameters were calculated as described above. The standard curve, graphed with theophylline and cortisol concentration on the x-axis verses % $B/B_0$ on the y-axis, illustrated that the standard curves could be independently constructed from a mixed analyte assay (FIGS. 10 and 11).

We claim:

1. A chemiluminescent labeled conjugate comprising an acridinium or benzacridinium moiety covalently attached to a luminophore via a spacer, said moiety further conjugated to a biological molecule of interest, wherein said spacer is of an appropriate length to allow the excited species generated from said moiety to transfer energy to said luminophore, resulting in the emission of light in the spectral region of said luminophore.

2. The chemiluminescent labeled conjugate of claim 1, wherein said spacer is a linear, branched, or cyclic alkyl, alkenyl, alkynyl, alkoxyl, or aralkyl chain of less than 50 angstrom long, optionally including up to 20 heteroatoms.

3. The chemiluminescent labeled conjugate of claim 2, wherein said spacer is less than 30 angstrom long, optionally including up to 12 heteroatoms.

4. The chemiluminescent labeled conjugate of claim 3, wherein said spacer is less than 10 angstrom long, optionally including up to 8 heteroatoms.

5. The chemiluminescent labeled conjugate of claim 1, wherein said spacer comprises at least one linkage resulting from the coupling of side chains of the acridinium or benzacridinium moiety and said luminophore, wherein said linkage is selected from the group consisting of —NHCO— (amide), —CONH— (amide), —NHCOO— (carbamate), —O— (ether), C=N—O— (oxime ether), —S— (thioether, or sulfide), —S—S— (disulfide), —NHCO—NH— (urea), —NHCSNH— (thiourea), —C=N—(imino)-, —NH— (amino), —N=N— (diazo), —COO— (ester), —C=C— (vinyl, alkenyl, or olefinic), and —SO₂NH— (sulfonamide), —C≡C— (alkynyl), —OPO₃—, —PO₃—, —OSO₃—, and —SO₃—.

6. The chemiluminescent labeled conjugate of claim 1, wherein said luminophore is capable of producing emission spectra covering from blue to infra red region.

7. The chemiluminescent labeled conjugate of claim 1, wherein said luminophore is selected from the group consisting of a phosphorescent moiety, a fluorescent moiety and, a fluorescent or phosphorescent moiety precursor convertible to a fluorescent or phosphorescent moiety.

8. The chemiluminescent labeled conjugate of claim 1, wherein said biological molecule of interest is selected from the group consisting of haptens, ligands, polysaccharides, polypeptides, receptors, antibodies, and nucleic acids.

9. A chemiluminescent labeling agent comprising an acridinium or benzacridinium moiety covalently attached to a luminophore via a spacer, wherein said spacer is of an appropriate length to allow the excited species generated from said moiety to transfer energy to said luminophore, resulting in the emission of light in the spectral region of said luminophore.

10. The chemiluminescent labeling agent of claim 9, wherein said spacer is a linear, branched or cyclic alkyl, alkenyl, alkynyl, alkoxyl, or aralkyl chain of less than 50 angstrom long, optionally including up to 20 heteroatoms.

11. The chemiluminescent labeling agent of claim 10, wherein said spacer is less than 30 angstrom long, optionally including up to 12 heteroatoms.

12. The chemiluminescent labeling agent of claim 11, wherein said spacer is less than 10 angstrom long, optionally including up to 8 heteroatoms.

13. The chemiluminescent labeling agent of claim 9, wherein said spacer comprises at least one linkage resulting from the coupling of side chains of the acridinium or benzacridinium moiety and said luminophore, wherein said linkage is selected from the group consisting of —NHCO— (amide), —CONH— (amide), —NHCOO— (carbamate), —O— (ether), —C=N—O— (oxime ether), —S— (thioether, or sulfide), —S—S— (disulfide), —NHCO—NH— (urea), —NHCSNH— (thiourea), —C=N—(imino)-, —NH— (amino), —N=N— (diazo), —COO— (ester), —C=C— (vinyl, alkenyl, or olefinic), and —SO₂NH— (sulfonamide), —C≡—C— (alkynyl), —OPO₃—, —PO₃—, —OSO₃—, and —SO₃—.

14. The chemiluminescent labeling agent of claim 9, wherein said luminophore is capable of producing emission spectra covering from blue to infra red region.

15. The chemiluminescent labeling agent of claim 14, wherein said luminophore is selected from the group consisting of a phosphorescent moiety, a fluorescent moiety and, a fluorescent or phosphorescent moiety precursor convertible to a fluorescent or phosphorescent moiety.

16. A chemiluminescent labeled conjugate of the formula (I) or (II):

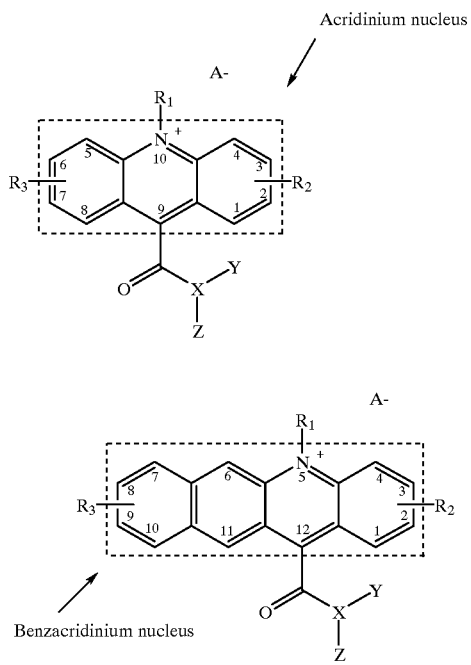

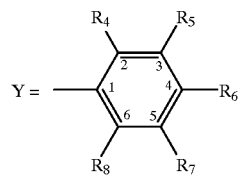

wherein
- one of $R_1$, $R_2$, or $R_3$ is luminophore linked to a first side chain, wherein said side chain is of an appropriate length to allow the excited species generated from the acridinium or benzacridinium moiety to transfer energy to said luminophore, resulting in the emission of light in the spectral region of said luminophore;
- when $R_1$ is not substituted with a luminophore linked to a first side chain, then $R_1$ alternatively, is an alkyl, alkenyl, alkynyl or aralkyl, containing optionally up to 20 heteroatoms;
- when $R_2$ or $R_3$ are not substituted with a luminophore linked to a first side chain, then $R_2$ and $R_3$ alternatively, are identical or different, single or multiple groups at $C_{1-4}$ and $C_{5-8}$ for formula (I), and at $C_{1-4}$ and $C_{6-11}$ for formula (II) respectively, selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;
- $A^-$ is a counterion;
- X is nitrogen, oxygen or sulfur;
- when X is oxygen or sulfur, Z is omitted and Y is a polysubstituted aryl moiety of the formula:

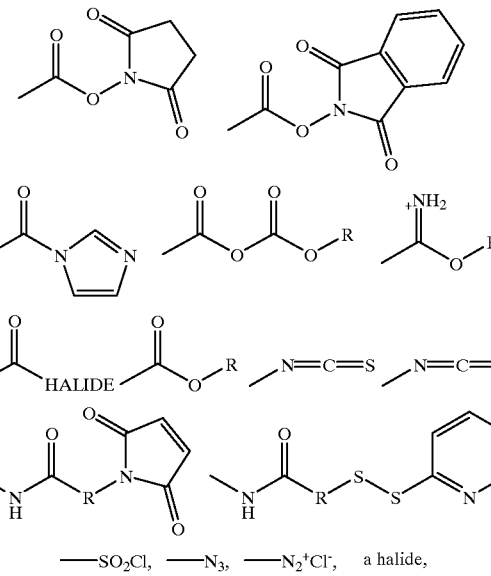

where $R_4$ and $R_8$ are alkyl, alkenyl, alkynyl, alkoxyl (—OR), alkylthiol (—SR), or substituted amino groups that serve to stabilize the —COX— linkage between the acridinium or benzacridinium nucleus and the Y moiety, through steric and/or electronic effect; $R_4$ and $R_8$ can be either the same or different; one of $R_4$ and $R_8$ can be hydrogen;
- $R_5$ and $R_7$ are selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;
- $R_6$ is —$R_9$—$R_{10}$, where $R_9$ is a second side chain, not required but optionally can be a branched or straight-chained alkyl, substituted or unsubstituted aryl or aralkyl containing optionally up to 20 heteroatoms, and
- $R_{10}$ is (a) a leaving group or an electrophilic functional group attached to a leaving group selected from the group consisting of —$SO_2Cl$, —$N_3$, —$N_2^+Cl^-$, a halide, (b) —COOH, Q—R—Nu, —Q—R—$I_n$Nu—, —Q—Nu, —R—Nu and —Nu, wherein n is a number of at least 1, Nu is a nucleophilic group, Q is a functional linkage, I is an ionic or ionizable group;
- when X is nitrogen, Y is (1) a branched or straight-chain alkyl group, containing up to 20 carbon atoms and optionally up to 10 heteroatoms or (2) a substituted or non-substituted aryl or heteroaryl group containing up to 20 carbon atoms; Z is —$SO_2$— Y', where Y' is defined the same as Y above (in the case where X is nitrogen); Y and Y' can have either the same or different chemical composition;
- R is selected from the group consisting of alkyl, alkenyl, alkynyl, aryl and aralkyl containing optionally up to 20 heteroatoms;
- $R_5$, $R_6$, and $R_7$ are interchangeable; and
- $R_{10}$ is conjugated to a biological molecule of interest.

17. The chemiluminescent labeled conjugate of claim 16, wherein said first side chain is a linear, branched, or cyclic alkyl, alkenyl, alkynyl, alkoxyl, or aralkyl chain of less than 50 angstrom long, optionally including up to 20 heteroatoms.

18. The chemiluminescent labeled conjugate of claim 17, wherein said first side chain is less than 30 angstrom long, optionally including up to 12 heteroatoms.

19. The chemiluminescent labeled conjugate of claim 18, wherein said first side chain is less than 10 angstrom long, optionally including up to 8 heteroatoms.

20. The chemiluminescent labeled conjugate of claim 16, wherein said first side chain comprises at least one linkage resulting from the coupling of said side chains of the acridinium or benzacridinium moiety and said luminophore, wherein said linkage comprises —NHCO— (amide), —CONH— (amide), —NHCOO— (carbamate), —O— (ether), —C=N—O— (oxime ether), —S— (thioether, or sulfide), —S—S— (disulfide), —NHCO—NH— (urea), —NHCSNH— (thiourea), —C=N— (imino)-, —NH— (amino), —N=N— (diazo), —COO— (ester), —C=C— (vinyl, alkenyl, or olefinic), and —SO$_2$NH— (sulfonamide), —C≡C— (alkynyl), —OPO$_3$—, —PO$_3$—, —OSO$_3$—, or —SO$_3$—.

21. The chemiluminescent labeled conjugate of claim 16, wherein said luminophore is capable of producing emission spectra covering from blue to infra red region.

22. The chemiluminescent labeled conjugate of claim 21, wherein said luminophore is selected from the group consisting of a phosphorescent moiety, a fluorescent moiety and, a fluorescent or phosphorescent moiety precursor convertible to a fluorescent or phosphorescent moiety.

23. The chemiluminescent labeled conjugate of claim 16, wherein said biological molecule of interest is selected from the groups consisting of haptens, ligands, polysaccharides, polypeptides, receptors, antibodies, and nucleic acids.

24. A chemiluminescent labeling agent for conjugation to a biological molecule of interest, said agent having the formula (I) or (II):

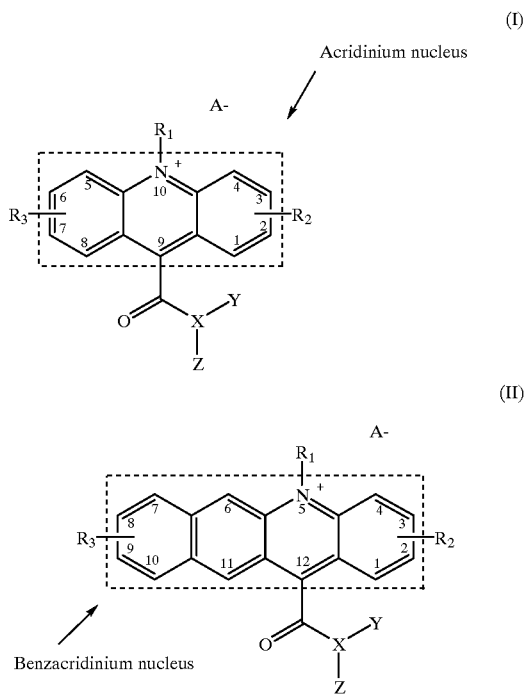

wherein
one of $R_1$, $R_2$, or $R_3$ is a luminophore linked to a first side chain, wherein said side chain is of an appropriate length to allow the excited species generated from the acridinium or benzacridinium moiety to transfer energy to said luminophore, resulting in the emission of light in the spectral region of said luminophore;
when $R_1$ is not substituted with a luminophore linked to a first side chain, then $R_1$ alternatively, is an alkyl, alkenyl, alkynyl or aralkyl, containing optionally up to 20 heteroatoms;

when $R_2$ or $R_3$ are not substituted with a luminophore linked to a first side chain, then $R_2$ and $R_3$ alternatively, are identical or different, single or multiple groups at $C_{1-4}$ and $C_{5-8}$ for formula (I), and at $C_{1-4}$ and $C_{6-11}$ for formula (II) respectively, selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

$A^-$ is a counterion;

X is nitrogen, oxygen or sulfur;

when X is oxygen or sulfur, Z is omitted and Y is a polysubstituted aryl moiety of the formula:

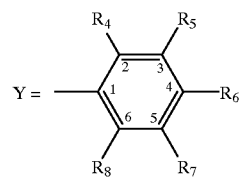

where $R_4$ and $R_8$ are alkyl, alkenyl, alkynyl, alkoxyl (—OR), alkylthiol (—SR), or substituted amino groups that serve to stabilize the —COX— linkage between the acridinium or benzacridinium nucleus and the Y moiety, through steric and/or electronic effect; $R_4$ and $R_8$ can be either the same or different; one of $R_4$ and $R_8$ can be hydrogen;

$R_5$ and $R_7$ are selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

$R_6$ is —$R_9$—$R_{10}$, where $R_9$ is a second side chain, not required but optionally can be a branched or straight-chained alkyl, substituted or unsubstituted aryl or aralkyl containing optionally up to 20 heteroatoms, and $R_{10}$ is (a) a leaving group or an electrophilic functional group attached to a leaving group selected from the group consisting of

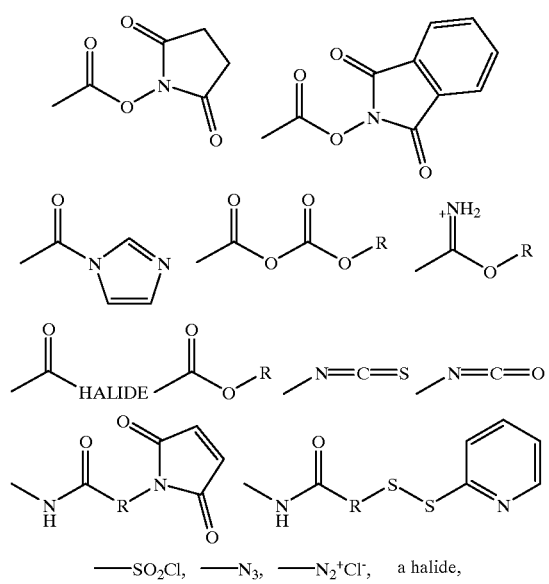

—SO$_2$Cl, —N$_3$, —N$_2^+$Cl$^-$, a halide, (b) —COOH, Q—R—Nu, —Q—R—I$_n$Nu—, —Q—Nu, —R—Nu and —Nu, wherein n is a number of at least 1, Nu is a nucleophilic group, Q is a functional linkage, I is an ionic or ionizable group;

when X is nitrogen, Y is (1) a branched or straight-chain alkyl group, containing up to 20 carbon atoms and optionally up to 10 heteroatoms or (2) a substituted or non-substituted aryl or heteroaryl group containing up to 20 carbon atoms; Z is —SO$_2$—Y', where Y' is defined the same as Y above (in the case where X is nitrogen); Y and Y' can have either the same or different chemical composition;

R is selected from the group consisting of alkyl, alkenyl, alkynyl, aryl and aralkyl containing optionally up to 20 heteroatoms;

$R_5$, $R_6$, and $R_7$ are interchangeable; and $R_{10}$ is conjugated to a biological molecule of interest.

25. The chemiluminescent labeling agent of claim 24, wherein said first side chain is a linear, branched, or cyclic alkyl, alkenyl, alkynyl, alkoxyl, or aralkyl chain of less than 50 angstrom long, optionally including up to 20 heteroatoms.

26. The chemiluminescent labeling agent of claim 25, wherein said first side chain is less than 30 angstrom long, optionally including up to 12 heteroatoms.

27. The chemiluminescent labeling agent of claim 26, wherein said first side chain is less than 10 angstrom long, optionally including up to 8 heteroatoms.

28. The chemiluminescent labeling agent of claim 24, wherein said first side chain comprises at least one linkage resulting from the coupling of said side chains of the acridinium or benzacridinium moiety and said luminophore, wherein said linkage comprises —NHCO— (amide), —CONH— (amide), —NHCOO— (carbamate), —O— (ether), —C=N—O— (oxime ether), —S— (thioether, or sulfide), —S—S— (disulfide), —NHCO—NH— (urea), —NHCSNH— (thiourea), —C=N— (imino)-, —NH— (amino), —N=N— (diazo), —COO— (ester), —C=C— (vinyl, alkenyl, or olefinic), and —SO$_2$NH— (sulfonamide), —C≡C— (alkynyl), —OPO$_3$—, —PO$_3$—, —OSO$_3$—, or —SO$_3$—.

29. The chemiluminescent labeling agent of claim 24, wherein said luminophore is capable of producing emission spectra covering from blue to infra red region.

30. The chemiluminescent labeling agent of claim 29, wherein said luminophore is selected from the group consisting of a phosphorescent moiety, a fluorescent moiety and, a fluorescent or phosphorescent moiety precursor convertible to a fluorescent or phosphorescent moiety.

31. The chemiluminescent labeling agent of claim 24, wherein said biological molecule of interest is selected from the group consisting of haptens, ligands, polysaccharides, polypeptides, receptors, antibodies, and nucleic acids.

32. The chemiluminescent labeling agent of claim 24, wherein $R_{10}$ is attached to said first side chain and capable of coupling to said biological molecule of interest, and $R_6$ is hydrogen or $R_9$.

33. The chemiluminescent labeling agent of claim 24, wherein $R_{10}$ is attached to said luminophore, said luminophore being covalently linked at one end via the first side chain to said acridinium or benzacridinium nucleus and at the other end capable of coupling to said biological molecule of interest via $R_{10}$, and $R_6$ is hydrogen or $R_9$.

34. The chemiluminescent labeling agent of claim 24, wherein $R_6$ is capable of being linked to said biological molecule of interest and has its location exchanged with that of $R_1$, $R_2$, or $R_3$, said $R_1$, $R_2$, or $R_3$ being a substituent without a lumiphore.

35. In a binding assay comprising contacting an analyte and at least one chemiluminescent labeled compound or macromolecule, and determining the degree of binding between said analyte and said compound, or macromolecule; or in a binding assay comprising contacting an analyte and at least one chemiluminescent labeled compound, or macromolecule, to competitively displace or mutually exclude said chemiluminescent labeled compound, or macromolecule, from a limited number of common capture molecules for the determination of the degree of competitive, or mutually exclusive binding, or a combination of both the aforementioned binding assay architectures, comprising the improvement wherein said chemiluminescent labeled compound is the chemiluminescent labeled conjugate of claim 16.

36. The binding assay of claim 35, wherein at least two analytes are determined using at least two different chemiluminescent labeled compounds, with at least one of said compounds being said chemiluminescent conjugate, each of said compounds or conjugates having discernible emission spectra.

37. The binding assay of claim 36 wherein three analytes are determined using three different chemiluminescent labeled compounds, with at least one of said compounds being said chemiluminescent conjugate, each of said compounds or conjugates having discernible emission spectra.

38. The binding assay procedure of claim 36, wherein said determination of said analytes is performed simultaneously in the same reaction medium.

39. A test kit for determining the presence of at least one analyte in a test sample comprising at least one container of a chemiluminescent labeled conjugate of claim 16, having discernible emission spectrum.

40. The test kit of claim 39 further comprising a container of a second chemiluminescent labeled conjugate, wherein each of said conjugates have discernible emission spectra.

41. A method of preparing a chemiluminescent labeling agent of claim 24 comprising covalently linking an activated luminophore via said first side chain to said acridinium or said benzacridinium nucleus.

42. The method of claim 41, wherein said first side chain is a linear, branched, or cyclic alkyl, alkenyl, alkynyl, alkoxyl, or aralkyl chain of less than 50 angstrom long, optionally including up to 20 heteroatoms.

43. The method of claim 42, wherein said first side chain is less than 30 angstrom long, optionally including up to 12 heteroatoms.

44. The method of claim 43, wherein said first side chain is less than 10 angstrom long, optionally including up to 8 heteroatoms.

45. The method of claim 41, wherein said first side chain comprises at least one linkage resulting from the coupling of side chains of said acridinium or benzacridinium moiety and said luminophore, wherein said linkage comprises —NHCO— (amide), —CONH— (amide), —NHCOO— (carbamate), —O— (ether), —C=N—O— (oxime ether), —S— (thioether, or sulfide), —S—S— (disulfide), —NHCO—NH— (urea), —NHCSNH— (thiourea), —C=N— (imino)-, —NH— (amino), —N=N— (diazo), —COO— (ester), —C=C— (vinyl, alkenyl, or olefinic), and —SO$_2$NH— (sulfonamide), —C≡C— (alkynyl), —OPO$_3$—, —PO$_3$—, —OSO$_3$—, or —SO$_3$—.

46. A method of producing a chemiluminescent labeled conjugate of claim 16 comprising (a) covalently linking said biological molecule of interest to the second side chain of said acridinium or said benzacridinium moiety, then covalently linking the first side chain of said acridinium or benzacridinium moiety to an activated luminophore, or (b) covalently linking an activated luminophore to the first side chain of said acridinium or said benzacridinium moiety, then covalently linking the second side chain of said acridinium or benzacridinium moiety to said biological molecule of interest.

47. A method of producing a chemiluminescent labeled conjugate of claim 16 comprising covalently linking said biological molecule of interest to said polysubstituted aryl moiety of said acridinium or said benzacridinium moiety, then covalently linking said acridinium or benzacridinium moiety to a luminophore via said first side chain.

48. The method of claim 47, wherein said first side chain is a linear, branched, or cyclic alkyl, alkenyl, alkynyl, alkoxyl, or aralkyl chain of less than 50 angstrom long, optionally including up to 20 heteroatoms.

49. The method of claim 48, wherein said first side chain is less than 30 angstrom long, optionally including up to 12 heteroatoms.

50. The method of claim 49, wherein said first side chain is less than 10 angstrom long, optionally including up to 8 heteroatoms.

51. The method of claim 47, wherein said first side chain comprises at least one linkage resulting from the coupling of the functionalized side chain of the acridinium or benzacridinium nucleus and said functionalized luminophore.

52. The method of claim 51 wherein said linkage comprises —NHCO— (amide), —CONH— (amide), —NHCOO— (carbamate), —O— (ether), —C=N—O— (oxime ether), —S— (thioether, or sulfide), —S—S— (disulfide), —NHCO—NH— (urea), —NHCSNH— (thiourea), —C=N— (imino)-, —NH— (amino), —N=N— (diazo), —COO— (ester), —C=C— (vinyl, alkenyl, or olefinic), and —SO$_2$NH— (sulfonamide), —C≡C— (alkynyl), —OPO$_3$—, —PO$_3$—, —OSO$_3$—, —SO$_3$—.

53. The labeled conjugate of claim 16 in which said luminophore is Texas Red, Rhodamine, or Carboxynaphthofluorescein.

54. A chemiluminescent labeled conjugate of the formula (I) or (II):

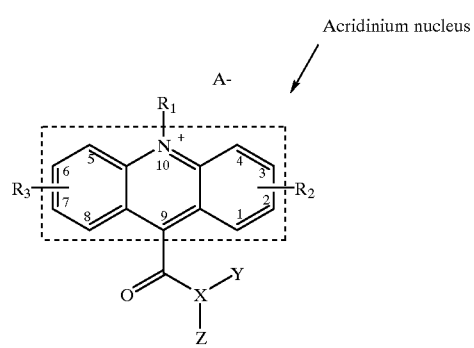

Acridinium nucleus (I)

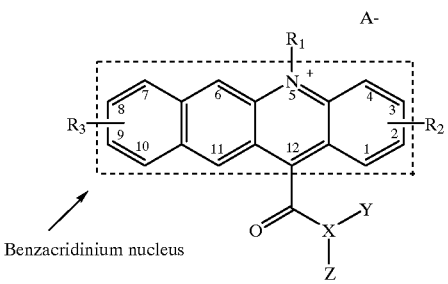

Benzacridinium nucleus (II)

wherein
one of $R_1$, $R_2$, or $R_3$ is a luminophore linked to a first side chain, wherein said side chain is of an appropriate length to allow the excited species generated from the acridinium or benzacridinium moiety to transfer energy to said luminophore, resulting in the emission of light in the spectral region of said luminophore;
when $R_1$ is not substituted with a luminophore linked to a first side chain, then $R_1$ alternatively, is an alkyl, alkenyl, alkynyl or aralkyl, containing optionally up to 20 heteroatoms;
when $R_2$ or $R_3$ are not substituted with a luminophore linked to a first side chain, then $R_2$ and $R_3$ alternatively, are identical or different, single or multiple groups at $C_{1-4}$ and $C_{5-8}$ for formula (I), and at $C_{1-4}$ and $C_{6-11}$ for formula (II) respectively, selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;
R is selected from the group consisting of alkyl, alkenyl, alkynyl, aryl and aralkyl containing optionally up to 20 heteroatoms;
A$^-$ is a counterion;
X is nitrogen, oxygen or sulfur;
when X is oxygen or sulfur, Z is omitted and Y is a polysubstituted aryl moiety of the formula:

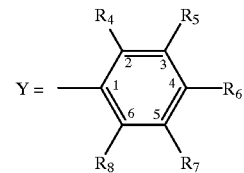

where $R_4$ and $R_8$ are alkyl, alkenyl, alkynyl, alkoxyl (—OR), alkylthiol (—SR), or substituted amino groups that serve to stabilize the —COX— linkage between the acridinium or benzacridinium nucleus and the Y moiety, through steric and/or electronic effect; $R_4$ and $R_8$ can be either the same or different; one of $R_4$ and $R_8$ can be hydrogen;
$R_5$ and $R_7$ are selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

$R_6$ is hydrogen or $R_9$, where $R_9$ is a side chain, not required but optionally can be a branched or straight-chained alkyl, substituted or unsubstituted aryl or aralkyl containing optionally up to 20 heteroatoms, and $R_5$, $R_6$, and $R_7$ are interchangeable;

$R_{10}$ is (a) a leaving group or an electrophilic functional group attached to a leaving group selected from the group consisting of

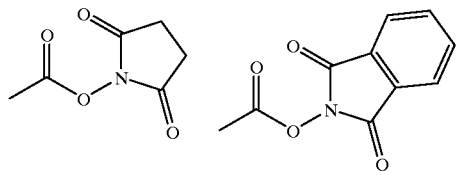

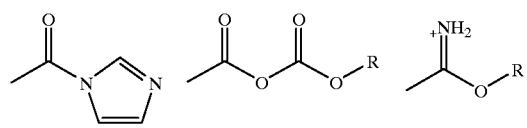

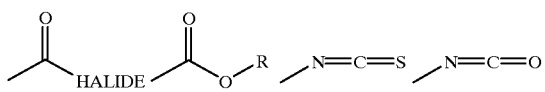

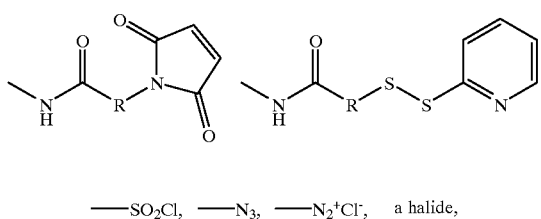

—SO$_2$Cl, —N$_3$, —N$_2^+$Cl$^-$, a halide, (b) —COOH, Q—R—Nu, —Q—R—I$_n$Nu—, —Q—Nu, —R—Nu and —Nu, wherein n is a number of at least 1, Nu is a nucleophilic group, Q is a functional linkage, I is an ionic or ionizable group;

when X is nitrogen, Y is (1) a branched or straight-chain alkyl group, containing up to 20 carbon atoms and optionally up to 10 heteroatoms or (2) a substituted or non-substituted aryl or heteroaryl group containing up to 20 carbon atoms; Z is —SO$_2$—Y', where Y' is defined the same as Y above (in the case where X is nitrogen); Y and Y' can have either the same or different chemical composition;

wherein $R_{10}$ is attached to said first side chain of said $R_1$, $R_2$ or $R_3$ and coupled with a biological molecule of interest.

55. A chemiluminescent labeled conjugate of the formula (I) or (II):

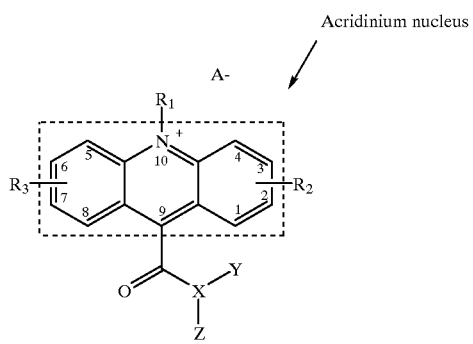

Acridinium nucleus

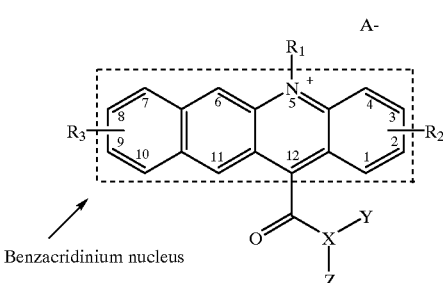

Benzacridinium nucleus wherein one of $R_1$, $R_2$, or $R_3$ is a luminophore linked to a first side chain, wherein said side chain is of an appropriate length to allow the excited species generated from the acridinium or benzacridinium moiety to transfer energy to said luminophore, resulting in the emission of light in the spectral region of said luminophore;

when $R_1$ is not substituted with a luminophore linked to a first side chain, then $R_1$ alternatively, is an alkyl, alkenyl, alkynyl or aralkyl, containing optionally up to 20 heteroatoms;

when $R_2$ or $R_3$ are not substituted with a luminophore linked to a first side chain, then $R_2$ and $R_3$ alternatively, are identical or different, single or multiple groups at $C_{1-4}$ and $C_{5-8}$ for formula (I), and at $C_{1-4}$ and $C_{6-11}$ for formula (II) respectively, selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

R is selected from the group consisting of alkyl, alkenyl, alkynyl, aryl and aralkyl containing optionally up to 20 heteroatoms;

A$^-$ is a counterion;

X is nitrogen, oxygen or sulfur;

when X is oxygen or sulfur, Z is omitted and Y is a polysubstituted aryl moiety of the formula:

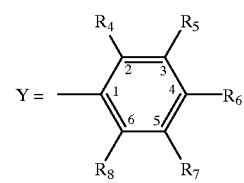

where $R_4$ and $R_8$ are alkyl, alkenyl, alkynyl, alkoxyl (—OR), alkylthiol (—SR), or substituted amino groups that serve to stabilize the —COX— linkage between the acridinium or benzacridinium nucleus and the Y moiety, through steric and/or electronic effect; $R_4$ and $R_8$ can be either the same or different; one of $R_4$ and $R_8$ can be hydrogen;

$R_5$ and $R_7$ are selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

$R_6$ is hydrogen or $R_9$, where $R_9$ is a second side chain, not required but optionally can be a branched or straight-chained alkyl, substituted or unsubstituted aryl or aralkyl containing optionally up to 20 heteroatoms, and $R_5$, $R_6$, and $R_7$ are interchangeable;

$R_{10}$ is (a) a leaving group or an electrophilic functional group attached to a leaving group selected from the group consisting of

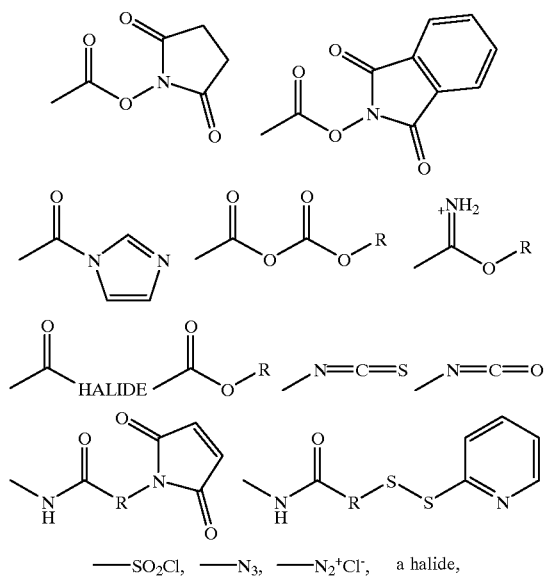

(b) —COOH, Q—R—Nu, —Q—R—$I_n$Nu—, —Q—Nu, —R—Nu and —Nu, wherein n is a number of at least 1, Nu is a nucleophilic group, Q is a functional linkage, I is an ionic or ionizable group;

when X is nitrogen, Y is (1) a branched or straight-chain alkyl group, containing up to 20 carbon atoms and optionally up to 10 heteroatoms or (2) a substituted or non-substituted aryl or heteroaryl group containing up to 20 carbon atoms; Z is —$SO_2$—Y', where Y' is defined the same as Y above (in the case where X is nitrogen); Y and Y' can have either the same or different chemical composition;

wherein said $R_{10}$ is attached to said luminophore, and conjugated to a biological molecule of interest.

56. A chemiluminescent labeled conjugate of the formula (I) or (II):

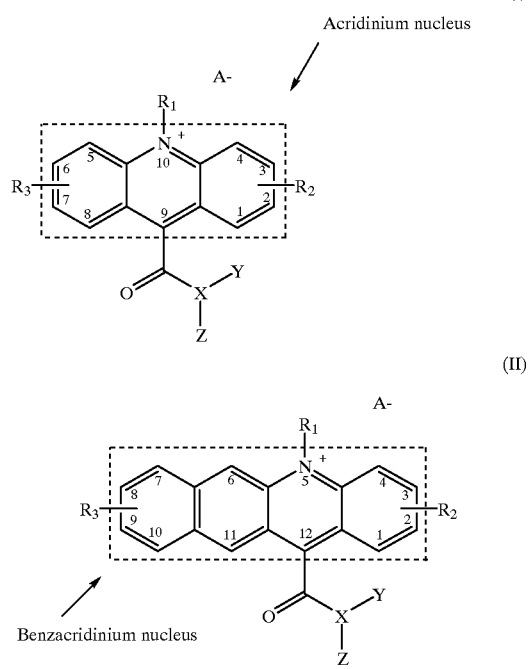

wherein
one of $R_1$, $R_2$, or $R_3$ is a luminophore linked to a first side chain, wherein said side chain is of an appropriate length to allow the excited species generated from the acridinium or benzacridinium moiety to transfer energy to said luminophore, resulting in the emission of light in the spectral region of said luminophore;

and one of $R_1$, $R_2$ or $R_3$ not having said lumiphore is $R_9$—$R_{10}$, said $R_{10}$ being conjugated to a biological molecule of interest and said $R_1$, $R_2$, or $R_3$ not having said lumiphore or said $R_9$—$R_{10}$ is an alkyl, alkenyl, alkynyl or aralkyl, containing optionally up to 20 heteroatoms;

R is selected from the group consisting of alkyl, alkenyl, alkynyl, aryl and aralkyl containing optionally up to 20 heteroatoms;

$A^-$ is a counterion;

X is nitrogen, oxygen or sulfur;

when X is oxygen or sulfur, Z is omitted and Y is a polysubstituted aryl moiety of the formula:

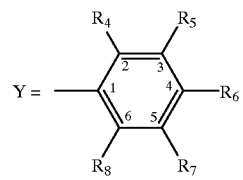

where $R_4$ and $R_8$ are alkyl, alkenyl, alkynyl, alkoxyl (—OR), alkylthiol (—SR), or substituted amino groups that serve to stabilize the —COX— linkage between the acridinium or benzacridinium nucleus and the Y moiety, through steric and/or electronic effect; $R_4$ and $R_8$ can be either the same or different; one of $R_4$ and $R_8$ can be hydrogen;

$R_5$ and $R_7$ are selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

$R_6$ is hydrogen or an alkyl, alkenyl, alkynyl or aralkyl, containing optionally up to 20 heteroatoms, $R_5$, $R_6$, and $R_7$ are interchangeable; and where $R_9$ is a second side chain, not required but optionally can be a branched or straight-chained alkyl, substituted or unsubstituted aryl or aralkyl containing optionally up to 20 heteroatoms, and $R_{10}$ is (a) a leaving group or an electrophilic functional group attached to a leaving group selected from the group consisting of

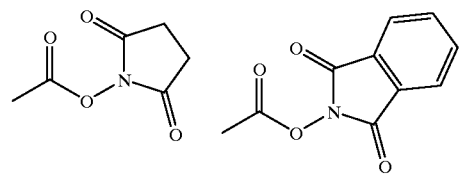

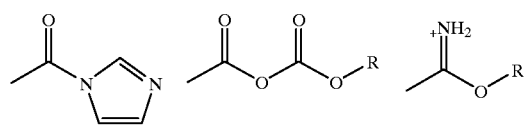

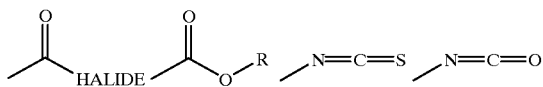

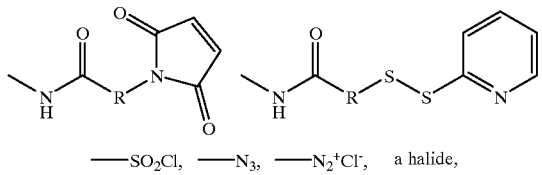

—SO$_2$Cl, —N$_3$, —N$_2^+$Cl$^-$, a halide, (b) —COOH, Q—R—Nu, —Q—R—I$_n$Nu—, —Q—Nu, —R—Nu and —Nu, wherein n is a number of at least 1, Nu is a nucleophilic group, Q is a functional linkage, I is an ionic or ionizable group;

when X is nitrogen, Y is (1) a branched or straight-chain alkyl group, containing up to 20 carbon atoms and optionally up to 10 heteroatoms or (2) a substituted or non-substituted aryl or heteroaryl group containing up to 20 carbon atoms; Z is —SO$_2$—Y', where Y' is defined the same as Y above (in the case where X is nitrogen); Y and Y' can have either the same or different chemical composition.

57. A chemiluminescent labeling agent for conjugation to a biological molecule of interest, said agent having the formula (I) or (II):

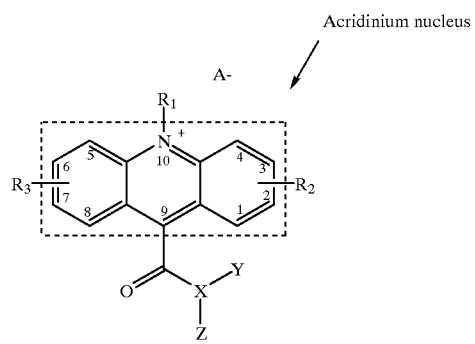

Acridinium nucleus

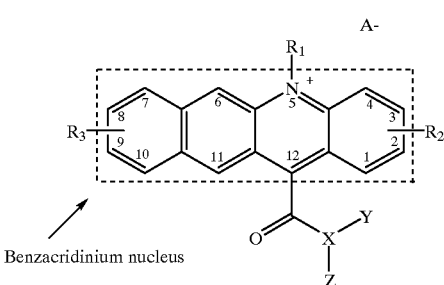

Benzacridinium nucleus wherein one of $R_1$, $R_2$, or $R_3$ is a luminophore linked to a first side chain, wherein said side chain is of an appropriate length to allow the excited species generated from the acridinium or benzacridinium moiety to transfer energy to said luminophore, resulting in the emission of light in the spectral region of said luminophore;

when $R_1$ is not substituted with a luminophore linked to a first side chain, then $R_1$ alternatively, is an alkyl, alkenyl, alkynyl or aralkyl, containing optionally up to 20 heteroatoms;

when $R_2$ or $R_3$ are not substituted with a luminophore linked to a first side chain, then $R_2$ and $R_3$ alternatively, are identical or different, single or multiple groups at $C_{1-4}$ and $C_{5-8}$ for formula (I), and at $C_{1-4}$ and $C_{6-11}$ for formula (II) respectively, selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

R is selected from the group consisting of alkyl, alkenyl, alkynyl, aryl and aralkyl containing optionally up to 20 heteroatoms;

A$^-$ is a counterion;

X is nitrogen, oxygen or sulfur;

when X is oxygen or sulfur, Z is omitted and Y is a polysubstituted aryl moiety of the formula:

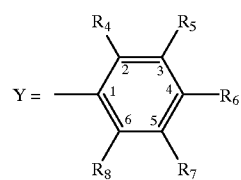

where $R_4$ and $R_8$ are alkyl, alkenyl, alkynyl, alkoxyl (—OR), alkylthiol (—SR), or substituted amino groups that serve to stabilize the —COX— linkage between the acridinium or benzacridinium nucleus and the Y moiety, through steric and/or electronic effect; $R_4$ and $R_8$ can be either the same or different; one of $R_4$ and $R_8$ can be hydrogen;

$R_5$ and $R_7$ are selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

$R_6$ is hydrogen or $R_9$, where $R_9$ is a side chain, not required but optionally can be a branched or straight-chained alkyl, substituted or unsubstituted aryl or aralkyl containing optionally up to 20 heteroatoms, and $R_5$, $R_6$, and $R_7$ are interchangeable;

$R_{10}$ is (a) a leaving group or an electrophilic functional group attached to a leaving group selected from the group consisting of

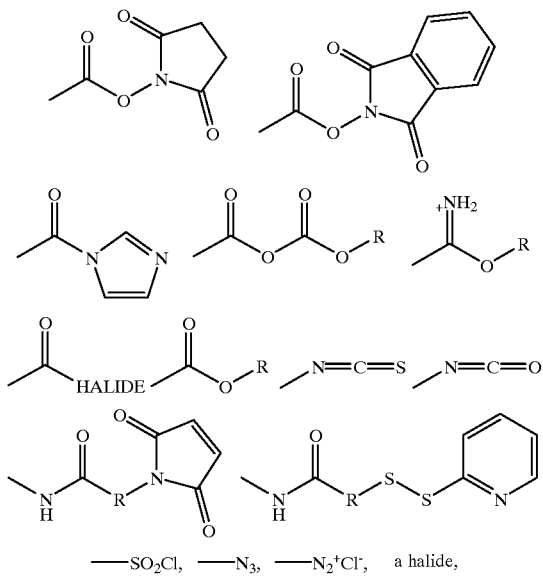

(b) —COOH, Q—R—Nu, —Q—R—$I_n$Nu—, —Q—Nu, —R—Nu and —Nu, wherein n is a number of at least 1, Nu is a nucleophilic group, Q is a functional linkage, I is an ionic or ionizable group;

when X is nitrogen, Y is (1) a branched or straight-chain alkyl group, containing up to 20 carbon atoms and optionally up to 10 heteroatoms or (2) a substituted or non-substituted aryl or heteroaryl group containing up to 20 carbon atoms; Z is —SO$_2$—Y', where Y' is defined the same as Y above (in the case where X is nitrogen); Y and Y' can have either the same or different chemical composition;

wherein $R_{10}$ is attached to said first side chain of said $R_1$, $R_2$ or $R_3$.

58. A chemiluminescent labeling agent for conjugation to a biological molecule of interest, said agent having the formula (I) or (II):

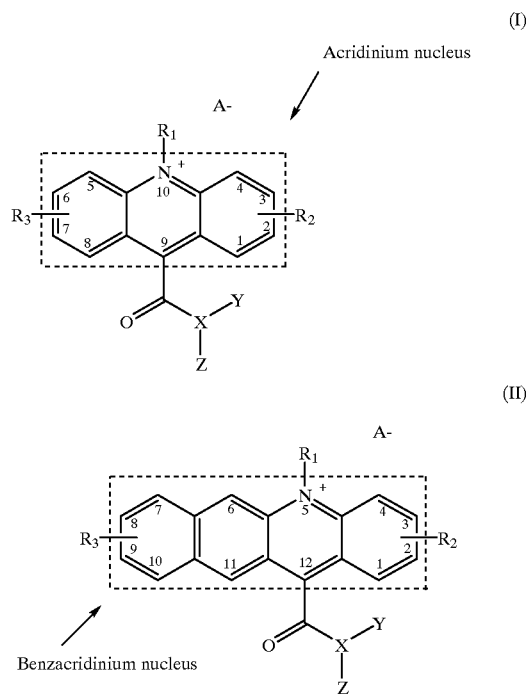

wherein one of $R_1$, $R_2$, or $R_3$ is a luminophore linked to a first side chain, wherein said side chain is of an appropriate length to allow the excited species generated from the acridinium or benzacridinium moiety to transfer energy to said luminophore, resulting in the emission of light in the spectral region of said luminophore;

when $R_1$ is not substituted with a luminophore linked to a first side chain, then $R_1$ alternatively, is an alkyl, alkenyl, alkynyl or aralkyl, containing optionally up to 20 heteroatoms;

when $R_2$ or $R_3$ are not substituted with a luminophore linked to a first side chain, then $R_2$ and $R_3$ alternatively, are identical or different, single or multiple groups at $C_{1-4}$ and $C_{5-8}$ for formula (I), and at $C_{1-4}$ and $C_{6-11}$ for formula (II) respectively, selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

R is selected from the group consisting of alkyl, alkenyl, alkynyl, aryl and aralkyl containing optionally up to 20 heteroatoms;

$A^-$ is a counterion;

X is nitrogen, oxygen or sulfur;

when X is oxygen or sulfur, Z is omitted and Y is a polysubstituted aryl moiety of the formula:

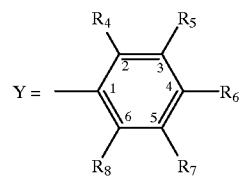

where $R_4$ and $R_8$ are alkyl, alkenyl, alkynyl, alkoxyl (—OR), alkylthiol (—SR), or substituted amino groups that serve to stabilize the —COX— linkage between the acridinium or benzacridinium nucleus and the Y moiety, through steric and/or electronic effect; $R_4$ and $R_8$ can be either the same or different; one of $R_4$ and $R_8$ can be hydrogen;

$R_5$ and $R_7$ are selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

$R_6$ is hydrogen or $R_9$, where $R_9$ is a second side chain, not required but optionally can be a branched or straight-chained alkyl, substituted or unsubstituted aryl or aralkyl containing optionally up to 20 heteroatoms, and $R_5$, $R_6$, and $R_7$ are interchangeable;

$R_{10}$ is (a) a leaving group or an electrophilic functional group attached to a leaving group selected from the group consisting of

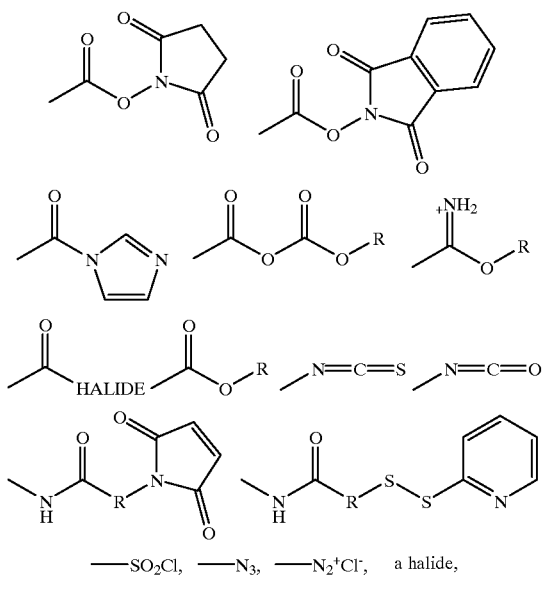

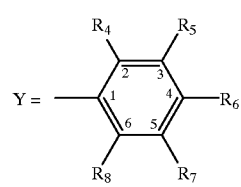

(b) —COOH, Q—R—Nu, —Q—R—$I_n$Nu—, —Q—Nu, —R—Nu and —Nu, wherein n is a number of at least 1, Nu is a nucleophilic group, Q is a functional linkage, I is an ionic or ionizable group;

when X is nitrogen, Y is (1) a branched or straight-chain alkyl group, containing up to 20 carbon atoms and optionally up to 10 heteroatoms or (2) a substituted or non-substituted aryl or heteroaryl group containing up to 20 carbon atoms; Z is —SO$_2$—Y', where Y' is defined the same as Y above (in the case where X is nitrogen); Y and Y' can have either the same or different chemical composition;

wherein said $R_{10}$ is attached to said luminophore.

59. A chemiluminescent labeling agent for conjugation to a biological molecule of interest, said agent having the formula (I) or (II):

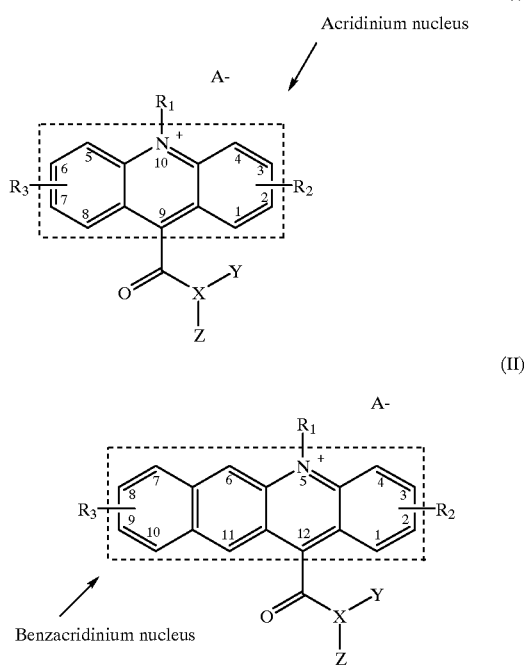

wherein
one of $R_1$, $R_2$, or $R_3$ is a luminophore linked to a first side chain, wherein said side chain is of an appropriate length to allow the excited species generated from the acridinium or benzacridinium moiety to transfer energy to said luminophore, resulting in the emission of light in the spectral region of said luminophore;

and one of $R_1$, $R_2$ or $R_3$ not having said lumiphore is $R_9$—$R_{10}$;

and said $R_1$, $R_2$, or $R_3$ not having said lumiphore or said $R_9$—$R_{10}$ is an alkyl, alkenyl, alkynyl or aralkyl, containing optionally up to 20 heteroatoms;

R is selected from the group consisting of alkyl, alkenyl, alkynyl, aryl and aralkyl containing optionally up to 20 heteroatoms;

A$^-$ is a counterion;

X is nitrogen, oxygen or sulfur;

when X is oxygen or sulfur, Z is omitted and Y is a polysubstituted aryl moiety of the formula:

$$Y = \begin{array}{c}\text{(aryl with } R_4, R_5, R_6, R_7, R_8\text{)}\end{array}$$

where $R_4$ and $R_8$ are alkyl, alkenyl, alkynyl, alkoxyl (—OR), alkylthiol (—SR), or substituted amino groups that serve to stabilize the —COX— linkage between the acridinium or benzacridinium nucleus and the Y moiety, through steric and/or electronic effect; $R_4$ and $R_8$ can be either the same or different; one of $R_4$ and $R_8$ can be hydrogen;

$R_5$ and $R_7$ are selected from the group consisting of hydrogen, substituted or unsubstituted aryl, halide, amino, hydroxyl, nitro, sulfonate, —R, —CN, —COOH, —SCN, —OR, —SR, —SSR, —C(O)R, —C(O)OR, —C(O)NHR, and —NHC(O)R;

$R_6$ is hydrogen or an alkyl, alkenyl, alkynyl or aralkyl, containing optionally up to 20 heteroatoms, $R_5$, $R_6$, and $R_7$ are interchangeable; and where $R_9$ is a second side chain, not required but optionally can be a branched or straight-chained alkyl, substituted or unsubstituted aryl or aralkyl containing optionally up to 20 heteroatoms, and $R_{10}$ is (a) a leaving group or an electrophilic functional group attached to a leaving group selected from the group consisting of

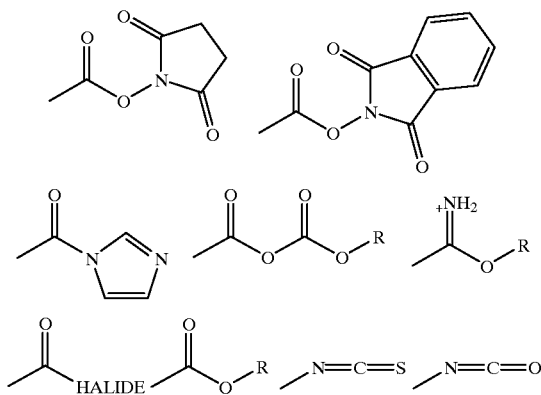

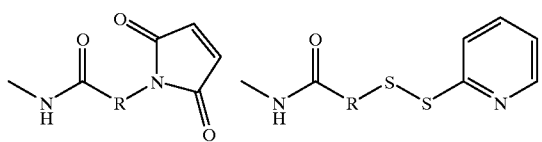

—SO$_2$Cl,  —N$_3$,  —N$_2^+$Cl$^-$,  a halide, (b) —COOH, Q—R—Nu, —Q—R—I$_n$Nu—, —Q—Nu, —R—Nu and —Nu, wherein n is a number of at least 1, Nu is a nucleophilic group, Q is a functional linkage, I is an ionic or ionizable group;

when X is nitrogen, Y is (1) a branched or straight-chain alkyl group, containing up to 20 carbon atoms and optionally up to 10 heteroatoms or (2) a substituted or non-substituted aryl or heteroaryl group containing up to 20 carbon atoms; Z is —SO$_2$—Y', where Y' is defined the same as Y above (in the case where X is nitrogen); Y and Y' can have either the same or different chemical composition.

* * * * *

UNITED STATES PATENT AND TRADEMARK OFFICE
CERTIFICATE OF CORRECTION

PATENT NO. : 6,165,800
DATED : December 26, 2000
INVENTOR(S) : Qingping et al.

It is certified that error appears in the above-identified patent and that said Letters Patent is hereby corrected as shown below:

Column 9,
Line 60, "quartemnerizing" should read -- quarternerizing --;

Column 17,
Line 28, "$CO_2H$" should read -- CO2H --;

Column 18,
Table 2, please replace Table 2 as follows:

| Compound | MW | RLU's/mol | |
|---|---|---|---|
| | | No Filter | OG550 Filter |
| Rhodamine-2-AM-DMAE-Bz | 1135 | 9.8 x E18 | 7.6 x E18 |
| Texas Red-2-AM-DMAE-COOH | 1115 | 7.2 x E18 | 5.2 x E18 |
| Texas Red-X-3-AM-DMAE-β-Alanine | 1300 | 1.8 x E19 | 1.3 x E19 |
| Rhodamine-2-AM-DMAE-Theophylline | 1391 | 1.4 x E19 | 1.2 x E19 |
| Rhodamine-2-AM-DMAE-COOH | 1046 | 6.4 x E18 | 3.7 x E18 |
| DMAE-Bz | 587 | 8.6 x E19 | 3.3 x E17 |

Columns 18 and 19,
Table 3, please replace Table 3 as follows:

Table 3

| Compound | Percent signal released over different lengths of time | | | | | |
|---|---|---|---|---|---|---|
| | 10s | 6s | 4s | 2s | 1s | 0.5s |
| Rhodamine-2-AM-DMAE-Bz | 100 | 94 | 92 | 87 | 65 | 17 |
| Rhodamine-2-AM-DMAE-COOH | 100 | 94 | 93 | 83 | 59 | 13 |
| Texas Red-2-AM-DMAE-COOH | 100 | 98 | 101 | 104 | 107 | 42 |
| CNF-2-AM-DMAE-COOH | 100 | 98 | 93 | 87 | 56 | 11 |
| Texas Red-3-AM-DMAE-COOH | 100 | 97 | 93 | 81 | 50 | 10 |
| Rhodamine-3-AM-DMAE-β-Alanine | 100 | 93 | 87 | 83 | 69 | 29 |
| Texas Red-X-3-AM-DMAE-β-Alanine | 100 | 99 | 98 | 97 | 84 | 41 |
| Texas Red-ED-NCM-DMPAE[1] | 100 | 67 | 51 | 30 | 15 | 4 |
| Texas Red-ED-NSP-DMPAE[2] | 100 | 64 | 47 | 28 | 16 | 6 |
| Rhodamine-2-AM-DMAE-HD-Theophylline | 100 | 100 | 100 | 97 | 94 | 36 |
| Texas Red-3-APO-DMAE-Bz | 100 | 97 | 94 | 91 | 80 | 35 |
| Texas Red-3-ABO-DMAE-Bz | 100 | 94 | 92 | 88 | 74 | 35 |
| DMAE-Bz | 100 | 99 | 96 | 80 | 48 | 10 |

1, 2 : Compounds having a very slow flash kinetics with $t_{1/2}$ much greater than 10 seconds.

UNITED STATES PATENT AND TRADEMARK OFFICE
CERTIFICATE OF CORRECTION

PATENT NO. : 6,165,800
DATED : December 26, 2000
INVENTOR(S) : Qingping et al.

It is certified that error appears in the above-identified patent and that said Letters Patent is hereby corrected as shown below:

Column 27,
Line 35, "10 To" should read -- To --;

Column 40,
Line 50, "arid" should read -- acid --;

Column 41,
Line 60, "dietbyl" should read -- diethyl --;

Column 42,
Line 66, "H2O" should read -- H$_2$O --;

Column 45
Line 35, "1H-" should read -- $^1$H- --;

Column 48,
Line 54, "chloridc;" should read -- chloride; --;
Line 63, "1H-NMR" should read -- $^1$H-NMR --; and Column 53,
Line 19, "Coming" should read -- Corning --.

Signed and Sealed this

Seventeenth Day of August, 2004

JON W. DUDAS
*Acting Director of the United States Patent and Trademark Office*